(12) United States Patent
Kim et al.

(10) Patent No.: US 6,984,462 B2
(45) Date of Patent: Jan. 10, 2006

(54) ORGANIC ELECTROLUMINESCENT DEVICES USING DOUBLE-SPIRO ORGANIC COMPOUNDS

(75) Inventors: Kong Kyeom Kim, Taejeon (KR); Sehwan Son, Taejeon (KR); Seokhee Yoon, Taejeon (KR); Jae soon Bae, Taejeon (KR); Youn-Gu Lee, Seoul (KR); Sung Gap Im, Taejeon (KR); Jieun Kim, Taejeon (KR); Jae Chol Lee, Taejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 10/718,083

(22) Filed: Nov. 19, 2003

(65) Prior Publication Data

US 2004/0170863 A1 Sep. 2, 2004

Related U.S. Application Data

(62) Division of application No. 10/099,781, filed on Mar. 14, 2002.

(30) Foreign Application Priority Data

Apr. 27, 2001 (KR) ............................... 2001-23038
Apr. 27, 2001 (KR) ............................... 2001-23039

(51) Int. Cl.
*H05B 33/14* (2006.01)

(52) U.S. Cl. ................... 428/690; 428/917; 257/102; 257/103; 313/504; 313/506; 427/66

(58) Field of Classification Search ............... 428/690, 428/917; 313/504, 506; 257/102, 103; 252/301.16; 549/29
See application file for complete search history.

(56) References Cited

U.S. PATENT DOCUMENTS

| | | | |
|---|---|---|---|
| 3,869,363 A | 3/1975 | Singh | |
| 5,026,894 A | 6/1991 | Tour et al. | .................... 558/46 |
| 5,840,217 A | 11/1998 | Lupo et al. | ................. 252/583 |
| 6,211,369 B1 * | 4/2001 | Salbeck et al. | ............... 546/18 |
| 2004/0067387 A1 * | 4/2004 | Kim et al. | .................. 428/690 |

FOREIGN PATENT DOCUMENTS

| | | | |
|---|---|---|---|
| CN | 1338499 | * | 3/2002 |
| JP | 11-273863 | | 10/1999 |

OTHER PUBLICATIONS

Smet, et al., A General Synthesis of Disubstituted Rubicenes, 1998, J. Org. Chem., 2769-2773.

(Continued)

*Primary Examiner*—Rena Dye
*Assistant Examiner*—Camie Thompson
(74) *Attorney, Agent, or Firm*—McKenna Long & Aldridge LLP

(57) ABSTRACT

Disclosed are double-spiro organic compounds and an organic electroluminescence (EL) device using the same. The double-spiro organic compounds are configured to have at least three planar and substantially linear moieties, such that one planar moiety is located between two neighboring planar moieties and that the intervening planar moiety shares an atom with each of the two neighboring planar moieties. The double-spiro compounds generally have high melting point above about 300 degree C. and low crystallinity, which provide thermal stability to the organic EL devices. These organic compounds have good sublimability. They also have light-emitting, hole-injecting, hole-transporting, electron injection, electron-transporting properties and characteristics, which are favorable in the organic EL devices.

26 Claims, 6 Drawing Sheets

OTHER PUBLICATIONS

Smet, et al. A Novel Acid-Catalyzed Rearrangement of 9,10-Diaryl-9, 10-Dihydroanthracene-9, 10-Diols Affording 10, 10'-Diaryl-9-Anthrones., 1999, Elsevier Science Ltd., Tetrahedron 55 7859-7874.

Hamada et al., Organic light-emitting diodes using a gallium complex., Apr. 20, 1998, American Institute of Physics, vol. 72, No. 16.

Murata et al., Organic light-emitting devices with saturated red emission using 6, 13-diphenylpentacene., Apr. 16, 2001, American Institute of Physics, vol. 78, No. 16.

Shi et al., Doped organic electroluminescent devices with improved stability., Mar. 31, 1997, American Institute of Physics, vol. 70, No. 13.

Adachi et al., High-efficiency organic electrophosphorescent devices with tris(2-phenylpyridine) iridium doped into electron-transporting materials., Aug. 7, 2000, American Institute of Physics, vol. 77, No. 6.

Adachi et al., High-efficiency red electrophosphorescence devices.. Marhc 12, 2001, American Institute of Physics, vol. 78, No. 11.

Burrows et al., Operating lifetime of phosphorescent organic light emitting devices., May 1, 2000, American Institute of Physics., vol. 76, No. 18.

Baldo et al., Very high-efficiency green organic light-emitting devices based on electrophosphorescence., Jul. 5, 1999, American Institute of Physics., vol. 75, No. 1.

Baldo et al., Improved energy transfer in electrophosphorescent devices., Jan. 18, 1999, American Institute of Physics., vol. 74, No. 3.

Hamada et al., Organic light-emitting diodes using 3- or 5-hyrdoxyflavone-metal compexes., Dec. 8, 1997, American Institute of Physics., vol. 71, No. 23.

Baldo et al., Improved energy transfer in electrophosphorescent devices., Jan. 18, 1999, American Institute of Physics., vol. 74, No. 3.

Gigli et al., High-efficiency oligothiopene-based light-emitting diodes., Jul. 26, 1999, American Institute of Physics., vol. 75, No. 4.

Kido et al., Fabrication of highly efficient organic electroluminescent devices., Nov. 9, 1998, American Institute of Physics., vol. 73, No. 19.

Yang et al., Photoluminescence and electroluminescence properties of dye-doped polymer system.. 1997, Elsevier Science S.A., Sythetic Metals., 335-336.

Watanabe et al. Optimization of emitting efficiency in organic LED cells using Ir complex., 2001, Elsevier Science S.A., Sythetic Metals., 203-207.

Liedenbaum., Low voltage operation of large area polymer LEDs., 1997, Elsevier Science S.A., Sythetic Metals., 109-111.

Hide et al., Conjugated polymers as solid-state laser materials., 1997, Elsevier Science S.A., Sythetic Metals., 35-40.

Muckl et al., Transient electroluminescence measurements on organic heterolayer light emitting diodes., 2000, Elsevier Science S.A., Sythetic Metals., 91-94.

Shoustikov et al., Orange and red organic light-emitting devices using aluminum tris(5-hydrocyquinoxaline), 1997, Elsevier Science S.A., Sythetic Metals., 217-221.

Tokito et al., strongly modified emissio from organic elelctroluminescent device with a microcavity., 1997. Elsevier Science S.A., Sythetic Metals., 49-52.

Wakimoto et al., Stability characteristics of quinacridone and coumarin molecules as guest dopants in the organic LEDs., 1997, Elsevier Science S.A., Sythetic Metals., 15-19.

Ma et al., Bright blue electroluminescent devices utiliaing poly (N—vinylcarbazole) doped with fluorescent dye., 1997, Elsevier Science S.A., Sythetic Metals., 331-332.

Sano et al., Organic electroluminescent devices doped condensed polycyclic aromatic compounds., 1997, Elsevier Science S.A., Sythetic Metals., 27-30.

Mitschke et al., The electroluminescence of organic materials., 2000, The Royal Society of Chemistry, 1471-1507.

Barbarella et al., Modified Oligothiphenes with High Photo and Electroluminescence Efficiencies., 1999, Advanced Materals, 11, No. 16.

Schmitz et al., Polyneric Light-Emitting Diodes Based on Poly($p$-phenylene ethynylene), Poly(triphenyldiamine), and Spiroquinoxaline., 2001, Advanced Functional Materials, 11, No. 1.

Lamansky et al., Synthesis and Characterization of Phosphorescent Cyclometalated Iridium Complexes., 2001, Dept. of Chemistry, University of Southern California, 1704-1711.

Lamansky et al., Highly Phosphorescent Bis-Cyclometalated Iridium Complexes: Synthesis, Photophysical Characterization, and Use in Organic Light Emitting Diodes., 2001, American Chemical Society, 123, 4304-4312.

Tsutsui et al., High Quantum Efficiency in Organic Light-Emitting Devices with Iridium-Complex as a Triplet Emissive Center., 1999, Japanese Journal fo Applied Physics., vol. 38, L1502-L1504.

Naito et al., Molecular Design for Nonpolymeric Organic Dye Glasses with Thermal Stability: Relations between Thermodynamic Parameters and Amorphous Properties., 1993, The Journal of Physical Chemistry, vol. 97, No. 23, 6240-6248.

Bath et al., Electron mobility in tris(8-hydroxy-quinoline) aluminum thin films determined via transient electroluminescence from single- and multilayer organic light-emitting diodes., Apr. 1, 2001, Journal of Applied Physics, vol. 89, No. 7, 3711-3719.

Adachi et al., Organic electroluminescence of silole-incorporated polysilane., 2000, Journal of Luminescence, vol. 87 89, 1174-1176.

Clarkson et al., Sprans with four aromatic radicals on the spiro carbon atom., 1930, The Chemistry Laboratory of the Unoversity of Michigan, vol. 52, 2881-2891.

The Journal of the American Chemical Society vol. LII, "*Spirans With Four Aromatic Radicals on the Spiro Carbon Atom*"; R. G. Clarkson and M. Gomberg (May 1930-Aug. 1930).

Communication from European Patent Office dated Feb. 16, 2005.

* cited by examiner

ORGANIC ELECTROLUMINESCENT DEVICES USING DOUBLE-SPIRO ORGANIC COMPOUNDS

RELATED APPLICATIONS

This application is a divisional application of application Ser. No. 10/099,781, Mar. 14, 2002, the contents of which is hereby incorporated herein by reference in their entirety.

BACKGROUND OF THE INVENTION

1. Field of the Invention

The present invention generally relates to organic electroluminescence. More particularly, the present invention pertains to novel organic compounds having electroluminescent (hereinafter referred to as "EL") characteristics and an organic EL device using the organic EL compounds.

2. Description of the Related Art

Organic electroluminescence is one of the instances in which electric current is converted into visible light by internal processes of certain organic molecules. Organic molecules having either fluorescent or phosphorescent characteristics generate light emission upon the application of electric current, although they differ in their internal processes and response time. Both organic fluorescent and phosphorescent molecules are referred to as organic EL or light-emitting molecules.

The organic EL technology has been used in luminescent displays which produce their own light, unlike liquid crystal displays, which require an independent light source. Various colors can be generated by using an individual color-generating compound or combining compounds generating basic color elements. This technology is advantageous over LCD technology in its low power consumption, faster response time, higher brightness level, unlimited viewing angle and thinner design.

A basic construction of an organic EL device includes two opposing electrodes, i.e., a cathode and an anode, and an intervening layer containing an organic light-emitting material. When applying an electric voltage between the electrodes, electrons and holes are injected from the cathode and anode, respectively, into the intervening layer. The holes and electrons recombine at organic light-emitting molecules in the intervening layer. Recombined pairs of electrons and holes, namely excitons, move around carrying the energy generated by the recombination and transfer the energy to other organic light-emitting molecules, particularly to those having a smaller band gap near the location of their recombination. The transferred energy is used to excite valence electrons of the organic light-emitting molecules, which generates photons when the electrons return to their ground state.

In order to improve energy efficiency, multiple-layered organic EL devices have been suggested. Generally, multiple-layered organic EL devices have one or more layers functioning as vehicles for hole injection, hole transportation, light emission, electron transportation, and electron injection. One or more layers of the multiple-layered constructions may have more than one function. Many organic compounds have been known to have physical properties and characteristics for use in such organic EL devices. However, there exists a need for new organic compounds for use in organic electroluminescence in order to improve various aspects of organic EL devices or the manufacture of such devices.

SUMMARY OF THE INVENTION

One aspect of the present invention provides a chemical compound of Chemical Formula I:

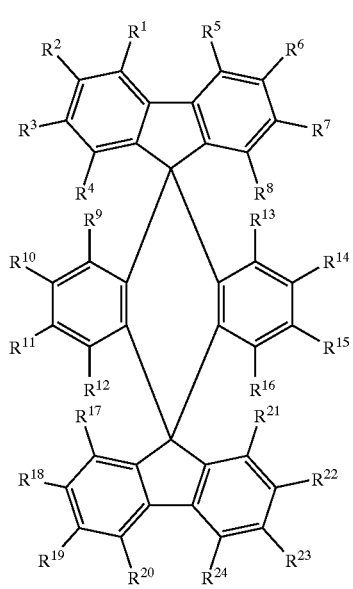

Chemical Formula 1

R1 through R24 are substituent groups, identical or different, but not all of R1 through R24 are hydrogen. Examples of the substituent groups R1–R24 will be described in detail. Among substituent groups available for R1–R24, one or more of R1–R24 are selected from the aryl group consisting of phenyl, biphenyl, terphenyl, benzyl, naphtyl, anthracyl, tetracenyl, pentacenyl, perylenyl, coronenyl, and heteroaryl, which are either substituted or unsubstituted. The aryl groups are further substituted with one or more phenyl, biphenyl, terphenyl, benzyl, naphtyl, anthracyl, tetracenyl, pentacenyl, perylenyl, coronenyl or heteroaryl, which are either substituted or unsubstituted. One or more of the R1–R24 are selected from the heteroaryl group consisting of thiophenyl, thiazolyl, oxazolyl, imidazolyl, and pyrazinyl, either substituted or unsubstituted. One or more of R1–R24 are selected from the group consisting of amines with at least one aryl substituent and aryl including phenyl, biphenyl, terphenyl, benzyl, naphtyl, anthracyl, tetracenyl, pentacenyl, perylenyl, coronenyl and heteroaryl. At least one of R1–R24 is anthracene or heteroaryl. The substituent groups R1 through R24 can be substituted by one or more organic moieties satisfying General Formula I. One or more of the R3, R7, R10, R11, R14, R15, R18, and R22 are substituted with non-hydrogen substituent groups. One or more pairs of R3 and R7; R18 and R22; R10 and R15; and R11 and R14 are substituted with non-hydrogen substituent groups.

The chemical compound of General Formula 1 is selected from the group consisting of Chemical Compounds 1–11, 100–137, 200–222, 300–308, and 400–413 as will be shown later. The compound has a melting point above about 300° C. The compound has a band-gap corresponding to visible light emission. The band-gap for the visible light emission is from about 1.8 eV to about 3.5 eV. The band-gap corresponds to blue, green or red light emission. The compound has a hole-transporting property. Hole mobility in the compound is about $1\times10^{-7}$ cm$^2$/Vs or greater. The compound has an electron-transporting property. Electron mobility in the compound is about $1\times10^{-7}$ cm$^2$/Vs or greater. The compound has a hole-injecting property. The compound has the highest occupied molecular orbital (HOMO) level from about −4.0 eV to about −6.0 eV. The compound has an electron-injecting property. The compound has the lowest unoccupied molecular orbital (LUMO) level from about −2.5 eV to about −4.0 eV.

Another aspect of the present invention provides a light-emitting material comprising one or more of the chemical compounds of General Formula I. The chemical compounds are selected from the group consisting of Chemical Compounds 100–137, 200–222, and 400–413.

Another aspect of the present invention provides a hole-transporting material comprising one or more of the chemical compounds of General Formula I. The chemical compounds are selected from the group consisting of Chemical Compounds 300–308 and 400–413.

Still another aspect of the present invention provides an electron-transporting material comprising one or more of the chemical compounds of General Formula 1. The chemical compounds are selected from the group consisting of Chemical Compounds 200–222.

Further, the present invention provides a solid deposition of one or more chemical compounds for use in organic electroluminescence. The chemical compounds comprise one or more double-spiro compounds, wherein the double-spiro compounds comprise at least three substantially planar organic moieties configured such that one planar moiety is interveningly located between the other two planar moieties and that the at least three planar moieties have substantially no overlap with one another; wherein the intervening planar moiety shares an atom with each of the two neighboring planar moieties; wherein the intervening planar moiety is substantially perpendicular to the two neighboring planar moieties; wherein the at least three planar moieties may be the same or different from each other; and wherein each of the planar moiety may be substituted with one or more non-planar moieties.

In the solid deposition, one or more double-spiro chemical compounds are in an amorphous form. The one or more chemical compounds further comprise one or more non-double-spiro compounds acceptable in organic electroluminescence. The one or more non-double-spiro compounds comprise a light-emitting compound. The non-double-spiro light-emitting compound has the band gap smaller than the band gap of the double-spiro compound. The non-double-spiro light-emitting compound has the band gap greater than the band gap of the double-spiro compound. The non-double-spiro light-emitting compound is either fluorescent or phosphorescent compound. The solid deposition is in the form of a thin film. The solid deposition comprises one or more layers. The double-spiro compound has one or more properties selected from the group consisting of visible light emission, electron transportation, electron injection, hole transportation, and hole injection.

In the double-spiro compounds, the atoms shared with the neighboring planar moieties are apart from each other in the intervening planar moieties. Two or more rings constitute at least one of the substantially planar moieties, and wherein the two or more rings are fused by sharing two or more atoms to form a substantially rigid plane. Each planar moiety is isolated from conjugation with its neighboring planar moieties. One or more of the planar moieties comprises a C3–C7 ring fused with one or more C4–C7 aromatic rings, and wherein one or more carbon atoms in the rings can be replaced by a heteroatom. One or more of the planar moieties comprises a C5–C6 ring fused with one or more C5–C6 aromatic rings, and wherein one or more carbon atoms in the rings can be replaced by a heteroatom. One or more of the planar moieties are selected from the group consisting of the following organic moieties:

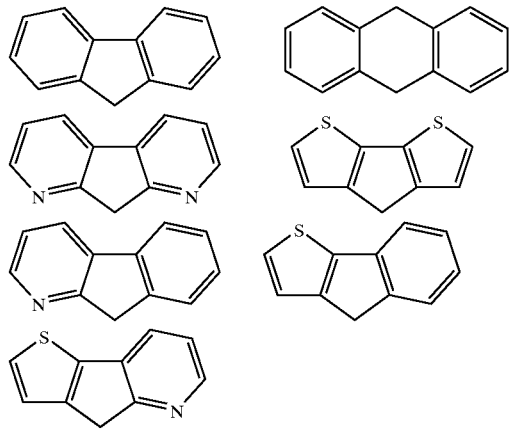

The double-spiro compound has a melting point above about 300° C. The double-spiro compound satisfies Chemical Formula I. In General Formula I, the R1 through R24 are one or more substituents selected from the group consisting of hydrogen atom, halogen atoms, substituted or unsubstituted alkyl groups having 1 to 18 carbon atoms, substituted or unsubstituted aryl groups having 6 to 24 carbon atoms, alkoxyl groups having 1 to 18 carbon atoms, substituted or unsubstituted heterocyclic or heteroaryl groups, substituted vinyl groups, amino group, amine groups, nitrile groups, nitro groups, formyl group, alkanoyl groups, substituted or unsubstituted carbazoles, alkyl sulfide groups, and aryl sulfide groups. The double-spiro compound are selected from the group consisting of Chemical Compounds 1–12, 100–137, 200–222, 300–308, and 400–413.

The one or more double-spiro compounds have a band gap corresponding to visible light emission. The band-gap for the visible light emission is from about 1.8 eV to about 3.5 eV. The band-gap corresponds to blue, green or red light emission. The double-spiro compounds have a hole-transporting property. Hole mobility in the one or more double-spiro compounds is about $1\times10^{-7}$ cm$^2$/Vs or greater. The double-spiro compounds have a electron-transporting property. Electron mobility in the one or more double-spiro compounds is about $1\times10^{-7}$ cm$^2$/Vs or greater. The double-spiro compounds have a hole-injecting property. The double-spiro compounds have the highest occupied molecular orbital (HOMO) level from about −4.0 eV to about 6.0 eV. The double-spiro compounds have a electron-injecting property. The double-spiro compounds has the lowest unoccupied molecular orbital (LUMO) level from about −2.5 eV to about 4.0 eV.

Still another aspect of the present invention provides a method of making the discussed solid deposition. The method comprises providing a support; and depositing one or more chemical compounds comprising one or more of the double-spiro compounds. The deposition of one or more chemical compounds comprises physical vapor deposition. Also, the deposition of one or more chemical compounds comprises forming multiple layers of different compositions of the one or more chemical compounds.

Still another aspect of the present invention provides an organic electroluminescent ("EL") device, which comprises an anode; a cathode; and the solid deposition located between the anode and cathode, wherein the solid deposition comprises one or more layers comprising a light-emitting layer. The light-emitting layer comprises the one or more double-spiro compounds having the band gap corresponding to visible light emission. The band-gap for the visible light emission is from about 1.8 eV to about 3.5 eV. The light-emitting layer comprises one or more fluorescent or phosphorescent materials. The organic EL device is supported by a substrate, and wherein the substrate contacts either the anode or the cathode. The one or more layers comprise at least one material having one or more properties selected from the group consisting of electron injection, electron transportation, light emission, hole transportation, and hole injection. The light-emitting layer comprises one or more selected from the group consisting of Chemical Compounds 100–137, 200–222, and 400–413. The light-emitting layer further comprises one or more non-double-spiro light-emitting compounds. The non-double-spiro light-emitting compound has the band gap smaller than the band gap of the double-spiro compound. The non-double-spiro light-emitting compound has the band gap greater than the band gap of the double-spiro compound. The non-double-spiro light-emitting compound is either fluorescent or phosphorescent compound. The one or more layers comprise at least one of the electron-injecting and electron-transporting layers. The at least one of the electron-injecting and electron-transporting layers comprises Chemical Compounds 200–222. The one or more layers comprise at least one of the hole-injecting and hole-transporting layers. The at least one of the hole-injecting and hole-transporting layers comprises Chemical Compounds 300–308 and 400–413.

A still further aspect of the present invention provides an electronic device comprising a display, wherein the display comprises the organic EL device as discussed.

A still further aspect of the present invention provides a method of generating visible light from the organic EL device as discussed above. The method comprises applying electric power between the anode and cathode of the device; the cathode injecting electrons toward the light-emitting layer; the anode injecting holes toward the light-emitting layer; and allowing recombination of at least part of the injected electrons and holes in the light-emitting layer, thereby generating visible light from the light-emitting layer. The light-emitting layer comprises the one or more double-spiro compounds having a light-emitting property. The light-emitting layer further comprises one or more non-double-spiro light-emitting compounds. The one or more layers comprises the double-spiro compound having one or more properties selected from the group consisting of visible light emission, electron transportation, electron injection, hole transportation, and hole injection.

A still further aspect of the present invention provides a method of manufacturing the organic EL device as discussed above. The method comprises: providing a substrate; forming a first conductive layer; depositing the one or more chemical compounds comprising one or more of the double-spiro compounds so as to form the solid deposition comprising the light-emitting layer; and forming a second conductive layer, wherein either of the first and second conductive layers corresponds to the anode or cathode. The formation of the light-emitting layer comprises depositing one or more of the double-spiro compounds having a light-emitting property. The formation of the light-emitting layer comprises co-depositing one or more non-double-spiro light-emitting compounds. The deposition of the one or more chemical compounds further comprises forming layers having one or more functions selected from the group consisting of visible light emission, electron transportation, electron injection, hole transportation, and hole injection. The formation of the layers having one or more functions comprises depositing one or more of the double-spiro compounds. The formation of the layers having one or more functions comprises depositing one or more non-double-spiro compounds.

DETAILED DESCRIPTION OF THE PREFERRED EMBODIMENT

Figure 1:
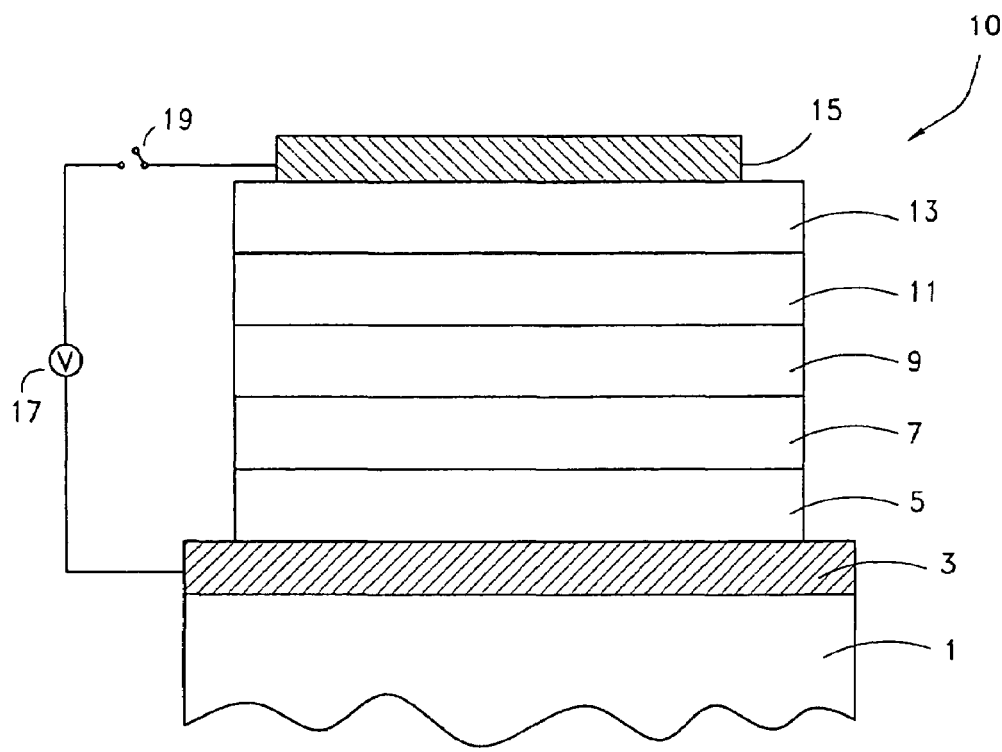
FIGS. 1–6 illustrate simplified cross-sectional views of various exemplary constructions of organic EL devices in accordance with the present invention.

Now the various aspects of the present invention will be discussed in more detail. It is to be understood at the outset of the description, which follows that persons of skill in the appropriate arts may modify the invention here described while still achieving the favorable results of this invention. Accordingly, the following description is to be understood as being a broad, teaching disclosure directed to persons of skill in the appropriate arts, and not as limiting upon the present invention.

Considerations for New Organic EL Materials

The present inventors have invented a group of new organic EL compounds. In the course of the research for new organic EL compounds, the inventors considered various factors relating to the applicability of chemical compounds to the manufacturing of organic EL devices. These factors include, among other things, electroluminescence of candidate chemical compounds, sublimability of the compounds under given manufacturing conditions, thermal stability of thin film made of the compounds, etc.

The electroluminescence of compounds is preferred although it is not always necessary for compounds to be used in organic EL devices. In order for an organic compound to generate visible light or to host another light-emitting compound, however, the organic compound needs to have its own electroluminescence. Although certain organic EL compounds have common functional groups or structural similarities, there is not a general rule as to what structures or elements of organic compounds would secure electroluminescence. Thus, it is difficult to find completely new structured organic EL compounds.

Not only must the compounds electroluminesce, but their colors of emission and efficiency of electroluminescence are also important. The colors and efficiency are considered with other properties of the compounds in determining what functions the organic EL compound can do in organic EL devices. For example, a compound emitting blue color alone may form a layer emitting blue light. Also, the blue light-emitting compound can be used as a blue light-emitting dopant or as a host material for hosting various light-emitting dopants in a full color display. Also, efficiency of electroluminescence may be relevant to the consideration of whether the compound is to be used as a host or a dopant.

Thermal stability of organic EL devices is a very important consideration. Quality of organic EL devices may deteriorate, as they happen to be subject to a high temperature, for example in a car heated by sunlight. Generally, organic EL devices have organic compounds in the form of amorphous thin films. The amorphous form of the compounds may crystallize when the temperature goes up above the glass transition temperature of the compounds. Even partial crystallization of the compounds may cause an electrical short between electrodes and result in the loss of electroluminescence. Crystallization in the amorphous films may also occur during the manufacturing process because it involves a high temperature. If crystallization occurs during the manufacturing, the very new products may have defects in the electroluminescence.

In order to avoid thermal crystallization of organic compounds, the glass transition temperature of the compounds must be higher than a temperature to which the deposited thin film can possibly be subjected. Generally, organic EL compounds having a glass transition temperature of about 120° C. or above are sufficient for use in organic EL devices. As glass transition temperature of a compound has good correlation with the melting point thereof, melting point is often used as a reference instead of glass transition temperature. The relationship between melting point and glass transition temperature is set forth in *Molecular Design for Nonpolymeric Organic Dye Glasses with Thermal Stability*, J. Phys. Chem. 97, 6240–6248 (1993), which is hereby incorporated herein by reference.

Also, crystallinity of the organic compounds is relevant to the crystallization of organic EL compounds in thin films and therefore the stability of the organic EL devices. The crystallinity of a compound may be defined as the degree of crystallization or its tendency to crystallize. When an organic compound has high crystallinity, it is more likely to crystallize under a given condition than others having low crystallinity. Accordingly, organic compounds having low crystallinity are preferred. It has been found that organic molecules having high planarity and rigidity tend to crystallize, regardless of their melting points or substrate temperature, when thin-films thereof are formed on a substrate either by solution processing or physical vapor deposition.

Further, organic EL compounds need to have good sublimability in view of the use of physical vapor deposition (PVD) in the formation of amorphous thin films. However, organic EL compounds with a high melting point generally have a large molecular weight and a poor sublimability. In fact, what is sought are organic EL compounds having high sublimability while having a sufficiently high melting point. Flat structures such as aromatic rings or hetero-rings may introduce too much pi-orbital overlap, which can be the source of traps impeding carrier transportation and quenching sites, thus reducing quantum efficiency of electroluminescence, by interaction of molecular orbitals, etc.

Further considerations include other characteristics of organic compounds such as hole injection, hole transportation, emission, electron transportation and electron injection functions and the like. For example, organic EL compounds for hole injection require compatibility with the material used for the anode. Also, consideration must be give to whether certain organic EL compounds can be used for more than one function. Multi-functional organic EL compounds enable the construction of a single layer performing multi-functions in organic EL device, and therefore can reduce processing costs, which otherwise would incur to produce additional layers.

Double-Spiro Compounds

With the considerations discussed above, the present inventors discovered organic compounds having a double-spiro structure that possess properties and characteristics favorable for use in organic EL devices. The term "spiro" refers to a configuration or structure in an organic molecule in which two planar moieties share an atom and are configured substantially perpendicular to each other. Here, the term "double-spiro" refers to a configuration of at least three substantially planar moieties, in which one planar moiety is interveningly located between two neighboring planar moieties and the intervening planar moiety shares an atom with each of the two neighboring planar moieties. The intervening planar moiety is substantially perpendicular to the two neighboring planar moieties. The two atoms shared with the neighboring planar moieties are preferably apart from each other in the intervening planar moieties.

The planar moieties in one organic compound can be the same or different from each other. Advantageously, each planar moiety in the double-spiro structure comprises at least one planar cyclic ring, whether substituted or not. The planar cyclic rings advantageously have conjugated double bonds, which provides the planar rigidity in the planar moieties. Two or more rings may constitute a planar moiety, in which they are advantageously fused by sharing two or more atoms to form a substantially rigid plane. Further, each planar moiety is advantageously isolated from conjugation with its neighboring planar moieties. Preferably, the planar moieties are composed of a C3–C7 ring fused with one or more C4–C7 aromatic rings. More preferably, the planar moieties are composed of a C5 or C6 cyclic ring fused with two C5–C6 aromatic rings. The carbon atoms in the planar moieties can be replaced by a heteroatom such as nitrogen, sulfur, and oxygen. The carbon and heteroatoms of each planar moiety can be substituted with various substituent groups. Some examples of planar moieties are shown as follows:

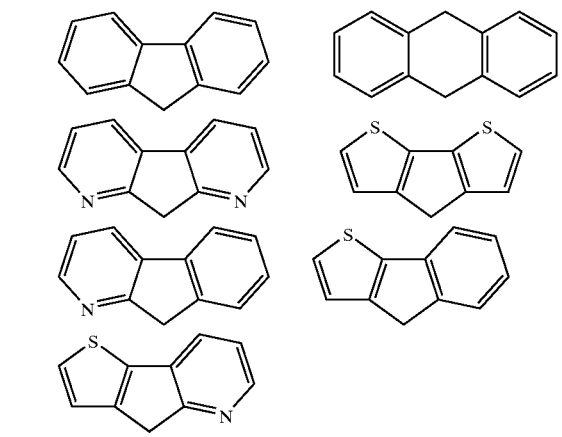

The double-spiro organic compounds generally meet the requirements of a high melting point, high sublimability and low crystallinity. The planar moieties with cyclic rings raise the molecular weight of these organic compounds. The high molecular weight generally increases the melting point and glass transition temperature. Also, the rigidity of the conjugated double bond ring structures and their aromaticity will enhance the sublimability of these compounds. Further, the substantially perpendicular configuration of neighboring planar moieties provides steric hindrance effect among the molecules. The steric hindrance will inhibit tight packing of the compounds in an orderly manner, whereby the crystallinity of these compounds is decreased.

Many of double-spiro structured organic compounds can emit visible light and have other properties including hole-injection, hole-transportation, electron-injection, and electron-transportation. These various properties can be provided in the double-spiro organic compounds by introducing appropriate functional groups on one or more of the planar moieties. For example, in one planar moiety a hole-transporting functional group is substituted, and in another planar moiety an electron-transporting functional group can be substituted. In the same way, bi- or multi-functional double-spiro organic EL materials can be prepared. This scheme is feasible particularly because each planar moiety is isolated from conjugation with its neighboring planar moieties and therefore the functional groups introduced in each of the planar moieties would not likely interfere with each other.

General Formula 1

Among various double-spiro structures, the organic compounds for use in the organic electroluminescence in accordance with the present invention satisfy General Formula 1 defined below.

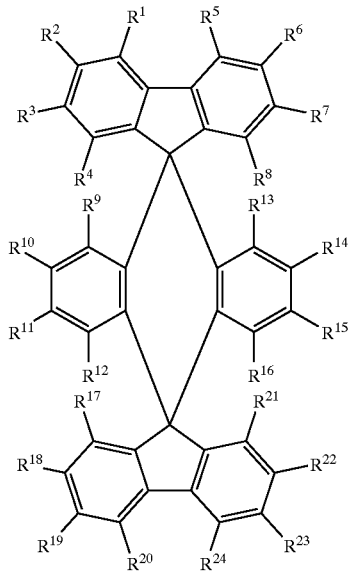

General Formula 1

R1 through R24 are identical or different substituent groups, namely hydrogen; halogen; cyano; hydroxyl; mercapto; C1–C18 alkyl which can be monosubstituted or polysubstituted by hydroxyl, carboxyl, C1–C6 alkyloxycarbonyl, formyl or C1–C6 alkylcarbonyl, the carbonyl groups of which can also be present in ketalized form, carbamoyl, N-hydroxycarbamoyl, sulfo, C1–C6 alkyloxy, hydroxy-C1–C6 alkyloxy, C1–C6 alkylthio, C1–C6 alkylsulfinyl, C1–C6 alkylsulfonyl, C2–C6 alkenyloxy, C 2–C6 alkenylthio, C2–C6 alkenylsulfinyl or C2–C6 alkenylsulfonyl, and of which 2 alkyl groups can also be linked to form an optionally substituted di- to deca-methylene ring in which a C atom can be replaced by a heteroatom and which can additionally contain one or two double bonds; cyano-C1–C3 alkyl, epoxy-C2–C6 alkyl, trifluoromethyl, hydroxyiminomethyl or C1–C4 alkoxyiminomethyl, pentafluoroethyl; C2–C6 alkynyl; C1–C18 alkoxy, which can also be substituted by hydroxyl, carboxyl or C1–C6 alkyloxycarbonyl; epoxy-C2–C6 alkoxy; C2–C6 alkenyloxy or C2–C6 alkynyloxy; C3–C7–Cycloalkyl or C3–C7–Cycloalkylmethyl, in which the ring can also be substituted by hydroxyl, halogen, carboxyl, C1–C6 alkyloxycarbonyl or cyano, and in which a C atom can be replaced by an oxygen, nitrogen or sulfur atom; C2–C6 alkenyl which can also be substituted by hydroxyl, hydrogen or C1–C6 alkyl; C4–C7–Cycloalkenyl; formyl or ketalized formyl; C1–C6 alkylcarbonyl which can also be substituted by hydroxyl and can also be present in ketalized form; arylcarbonyl or C1–C6 alkylcarbonylamino; carboxyl or C1–C6 alkoxycarbonyl; C1–C6 alkylthio, C1–C6 alkylsulfinyl or C1–C6 alkylsulfonyl, all of which can also be substituted by hydroxyl in the alkyl part; methylthio, methylsulfinyl or methylsulfonyl, all of which are substituted in the methyl part by carboxyl or C1–C6 alkyloxycarbonyl; C2–C6 alkenylthio, C2–C6 alkenylsulfinyl or C2–C6 alkenylsulfonyl; carbamoyl which can be monosubstituted on the nitrogen by C1–C6 alkyl, hydroxy-C1–C6 alkyl, C1–C6 alkyloxycarbonyl, C1–C6 alkylcarbonyl, carboxymethyl, C1–C6 alkyloxycarbonylmethyl, aminocarbonylmethyl, C1–C6 alkylaminocarbonyl, carbamoyl, hydroxyl or pyridyl, or which can be disubstituted on the nitrogen by C1–C6 alkyl; carbazoyl which can be substituted by C1–C4 alkyl or N-carbamoylcarbazoyl; sulfamoyl which can be monosubstituted on the nitrogen by C1–C6 alkylaminocarbonyl; pyridyl or 4-pyridon-1-yl; amino, C1–C6 alkyl amines, aryl amines, or arylalkyl amines, all of which can also be substituted; nitrile or nitro; C1–C6 alkyl sulfide; and phenyl, biphenyl, terphenyl, benzyl, naphtyl, anthracyl, tetracenyl, pentacenyl, perylenyl, coronenyl or heteroaryl, all of which can also be substituted with any of the substituent groups listed here.

One or more of these substituent groups can also be substituted by one or more organic moieties having a spiro or double-spiro configuration, preferably organic moieties of General Formula I. Preferably, the substituent group of phenyl, biphenyl, terphenyl, benzyl, naphtyl, anthracyl, tetracenyl, pentacenyl, perylenyl, coronenyl or heteroaryl are further substituted with one or more phenyl, biphenyl, terphenyl, benzyl, naphtyl, anthracyl, tetracenyl, pentacenyl, perylenyl, coronenyl or heteroaryl. Preferably, heteroaryl is a five- or six-membered aromatic rings where one or more C atoms are replaced by an oxygen, nitrogen or sulfur atom. More preferably, heteroaryl includes thiophenyl, thiazolyl, oxazolyl, imidazolyl, or pyrazinyl, either substituted or unsubstituted. The aryl group of the aryl amines or arylalkyl amines are identical or different and preferably selected from the group consisting of phenyl, biphenyl, terphenyl, benzyl, naphtyl, anthracyl, tetracenyl, pentacenyl, perylenyl, coronenyl and heteroaryl. Preferably, one or more of R1–R24 are selected from the group consisting of amines with at least one aryl substituent and aryl including phenyl, biphenyl, terphenyl, benzyl, naphtyl, anthracyl, tetracenyl, pentacenyl, perylenyl, coronenyl and heteroaryl. More preferably, at least one of R1–R24 is anthracene or heteroaryl.

In one embodiment, R3, R7, R10, R11, R14, R15, R18, R22 are substituted with non-hydrogen substituent groups. In another embodiment, the pairs of R3 and R7; R18 and R22; R10 and R15; and R11 and R14 are substituted with non-hydrogen substituent groups.

Compounds 100–137, 200–222, 300–308, and 400–413 are examples of the organic EL compounds having the double-spiro structure according to the present invention, the scope of which is not limited thereto.

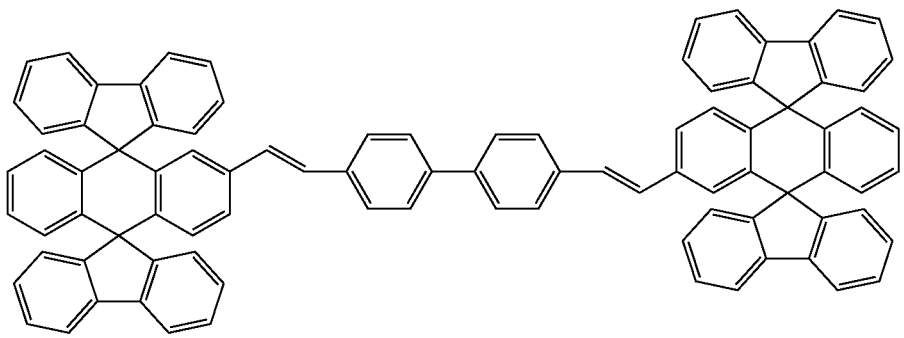
Chemical Compound 100
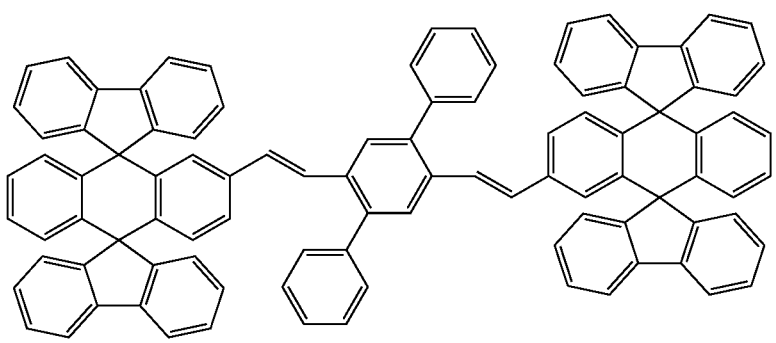
Chemical Compound 101
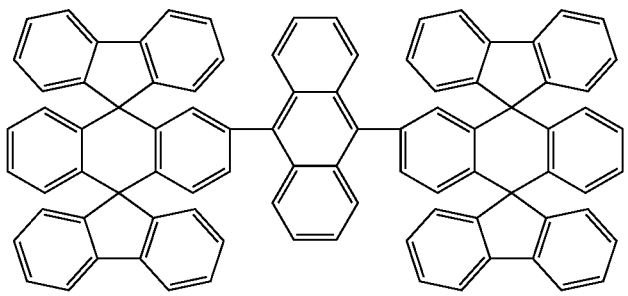
Chemical Compound 102
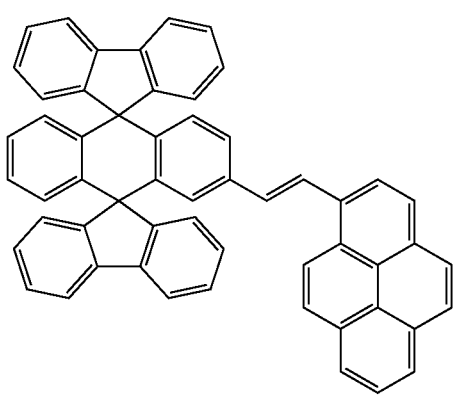
Chemical Compound 103
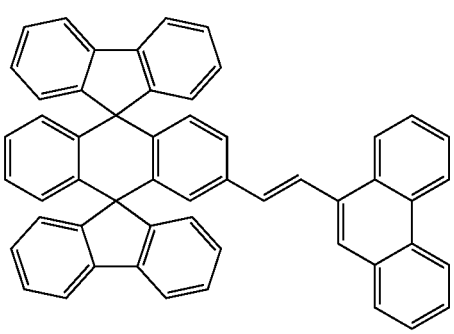
Chemical Compound 104
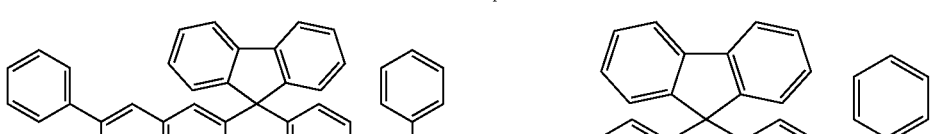
Chemical Compound 105    Chemical Compound 106

Double-spiro organic compounds satisfying General Formula 1 have light-emitting, hole-injecting, hole-transporting, electron injection, electron-transporting properties and characteristics, facilitating their use in the organic EL devices. Also, many of these compounds have more than one property so that they can be used to form a multifunctional layer in organic EL devices.

Compounds for use in Light Emission

Many double-spiro compounds, particularly those satisfying General Formula (I), have the property of emitting visible light when appropriate energy is applied. These double-spiro compounds have their band gaps corresponding to the visible light emission. Advantageously, the band gaps of the present double-spiro compounds range from about 1.8 eV to about 3.5 eV. The double-spiro light emitting compounds generate blue, green or red light although not limited thereto. The double-spiro light emitting compounds according to the invention include, for example, Chemical Compounds 100–137, 200–222, and 400–413. The double-spiro light emitting compounds can be used to form a light-emitting layer of organic EL devices alone or in combination with other light-emitting materials, as will be discussed later. Advantageously, these light-emitting double-spiro compounds can be used to host other EL compounds having higher quantum efficiency than their own. Also, these light-emitting compounds can be used as a light-emitting dopant in a light-emitting layer with another host material or in other layers of organic EL devices.

Compounds for use in Transportation and/or Injection of Electrons

The double-spiro compounds of the instant invention have good electron mobility. Such compounds are candidates for use in electron transportation because good mobility of electrons in those compounds will reduce the driving voltage of the organic EL devices using the compounds. In other words, free electrons in the compounds having high electron mobility are prone to move at a low electric potential difference. Advantageously, the compounds having electron mobility of about $1\times10^{-7}$ cm$^2$/Vs or greater can be used for electron transportation. A general discussion on carrier mobility can be found in *Electron Mobility in Tris (8-hydroxy-quinoline)aluminum Thin Films Determined via Transient Electroluminescence From Single- and Multiple-Layer Organic Light-Emitting Diodes*, J. Appl. Phys., Vol 89, 3712 (2001); *Transient Electroluminescence Measurements on Organic Heterolayer Light Emitting Diodes*, Synthetic Metals 111–112, 91 (2000); and *Organic Electroluminescence of Silole-Incorporated Polysilane*, Journal of Luminescence 87–89, 1174 (2000), which are hereby incorporated herein by reference.

Also, among the compounds with good electron mobility is a group having their lowest unoccupied molecular orbital (LUMO) level relatively close to the work function of cathode materials. This group of compounds is especially suited for electron injection. This is also relevant to the driving voltage of the device because the compounds for electron injection reduce the electric potential barrier in the electron injection. Advantageously, the LUMO level of the instant compounds used for electron injection ranges from about −2.5 eV to about −4.0 eV. For example, Chemical Compounds 200–222 can be used for electron injection or transportation, or both. The double-spiro compounds with the properties of electron injection and/or transportation can be used to form an electron-injecting layer, an electron-transporting layer, or a layer having both electron injection and transportation functions in organic EL devices.

Compounds for use in Transportation and/or Injection of Holes

Various double-spiro compounds of the present invention have good hole mobility. Such compounds are candidates for use in hole transportation because the good mobility of holes in those compounds will reduce the driving voltage of an organic EL device using the compounds. Holes in the compounds having high hole mobility are prone to move at a low electric potential difference. Advantageously, double-spiro compounds having hole mobility of about $1\times10^{-7}$ cm$^2$/Vs or greater can be used for hole transportation. Also, among the compounds with good electron mobility is a group having their highest occupied molecular orbital (HOMO) level relatively close to the work function of anode materials. This group of compounds is especially suited for hole injection. This is relevant to the driving voltage as well because the compounds for hole injection primarily reduce the electric potential barrier in the hole injection. Advantageously, the HOMO level of the instant compounds used or hole injection ranges from about −4.0 eV to about −6.0 eV. For example, Chemical Compounds 300–308 and 400–413 can be used for hole injection or transportation, or both. The double-spiro compounds with the properties of hole injection and/or transportation can be used to form an hole-injecting layer, an hole-transporting layer, or a layer having both hole injection and transportation functions in organic EL devices.

Melting Points & Emission Color of Compounds of General Formula 1

Table 1 lists melting points and color of light emission of some exemplary double-spiro compounds of General Formula I.

TABLE 1

| Chemical Compound Nos. | Melting Point (° C.) | Color of Light Emission |
|---|---|---|
| 100 | >500 | Blue |
| 102 | >500 | Blue |
| 103 | 430 | Blue |
| 107 | 365.2 | Blue |
| 109 | 448 | Blue |
| 110 | 424.8 | Blue |
| 111 | 475.5 | Blue |
| 113 | 430.3 | Blue |
| 117 | 462.6 | Blue |
| 118 | 409.8 | Blue |
| 134 | 395.2 | Blue |
| 135 | >500 | Green |
| 200 | 462.9 | Blue |
| 305 | 353 | Blue |
| 307 | 315.9 | Blue |
| 308 | 329.2 | Blue |
| 301 | 370.4 | Blue |
| 303 | 326.0 | Blue |
| 400 | 358.7 | Blue |
| 401 | 489.5 | Blue |
| 403 | 413.0 | Blue |

As summarized in Table 1, the organic compounds of General Formula I have melting points sufficient to use in organic EL devices. The high melting point can be attributed, among other things, to the double-spiro structure with the fused six aromatic rings. Advantageously, these organic compounds have a melting point above about 300° C. and glass transition temperature above about 120° C. Preferably, the melting point is above about 400° C. Given the high melting point and high glass transition temperature, morphology changes or crystallization in the thin films of these organic compounds will be less likely. Therefore, the production yield and product stability of the organic EL devices will be substantially enhanced.

Sublimability of Compounds of General Formula 1

The double-spiro organic compounds of General Formula 1 show good sublimability while at the same time the melting points thereof are sufficiently high. The sublimability of these compounds can be attributed to the structural rigidity as discussed above. On one hand, each planar moiety in the compounds holds the two dimensional rigidity with its two fused phenyl rings; on the other hand, the whole double-spiro structure has the three dimensional rigidity by balancing the spatial location of the planar moieties. The aromatic phenyl units in the compounds can also add the sublimability as well.

Steric Hindrance Effects of Compounds of General Formula 1

Further, the steric hindrance effect of the substantially perpendicular configuration of each planar moiety makes the crystallinity of the compounds substantially lower than other compounds having the same or a similar number of conjugated double bond rings. If the steric hindrance effect of a compound is high, the melting point of the compound is generally low. In the compounds of General Formula 1, however, even if the steric hindrance effect exists, the high molecular weight keeps the melting point of the compounds sufficiently high, which prevents crystallization at a relatively low temperature.

Crystallinity of Compounds of General Formula 1

Also, the double-spiro compounds of General Formula 1 have relatively low crystallinity while having high aromaticity owing to the existence of six fused phenyl rings. Generally, compounds having high aromaticity are of high crystallinity and easy to crystallize. But, in the compounds of General Formula I, the conjugation of double bonds in each of the six phenyl rings does not overlap with other phenyl rings in the double-spiro structure. More particularly, the conjugations in the two phenyl groups fused with the pentagonal or hexagonal ring in each planar moiety do not overlap with each other in that planar moiety. Further, the conjugation in either of the phenyl groups of each planar moiety does not overlap with conjugation in another planer moiety of the double-spiro structure. This means that even if each planar moiety is substituted with groups forming extended conjugation with its phenyl groups, the pi-orbital overlap in the conjugation would not extend over another planar moiety and accordingly the whole molecule either. The lack of overlap of conjugation explains the relatively low crystallinity of these compounds.

Synthesis of Double-Spiro Compounds

Double-spiro compounds of General Formula 1 can be synthesized in various ways. For example, certain basic double-spiro compounds are first synthesized, and then they are modified to produce more complicated double-spiro compounds. For instance, the basic double-spiro compounds have one or more reactive atoms and/or functional groups as substituents in a double-spiro skeleton. Preferably, the reactive atoms and/or functional groups are halogen atoms and any acidic leaving groups. More preferably, they are selected from the group of chlorine, bromine, iodine, p-toluenesulfonic acid, and trifluoroacetic acid. Some exemplary basic double-spiro molecules are listed below as Chemical Compounds 1–11. In these compounds, "Br" may be substituted with any other reactive atoms or functional groups.

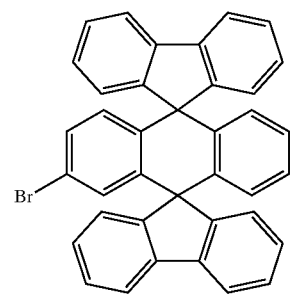

Chemical Compound 1

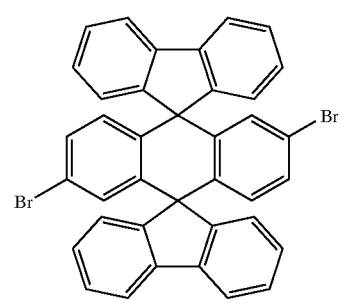

Chemical Compound 2

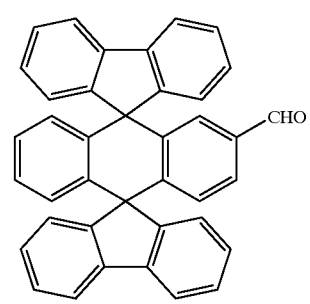

Chemical Compound 3

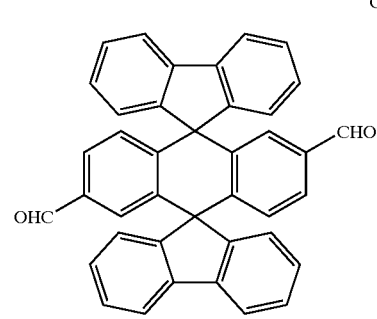

Chemical Compound 4

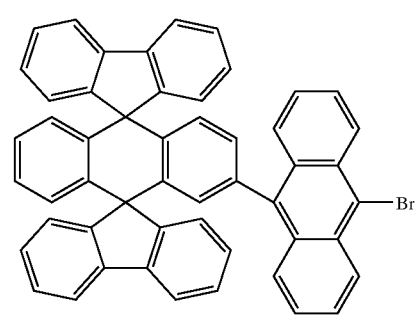

Chemical Compound 5

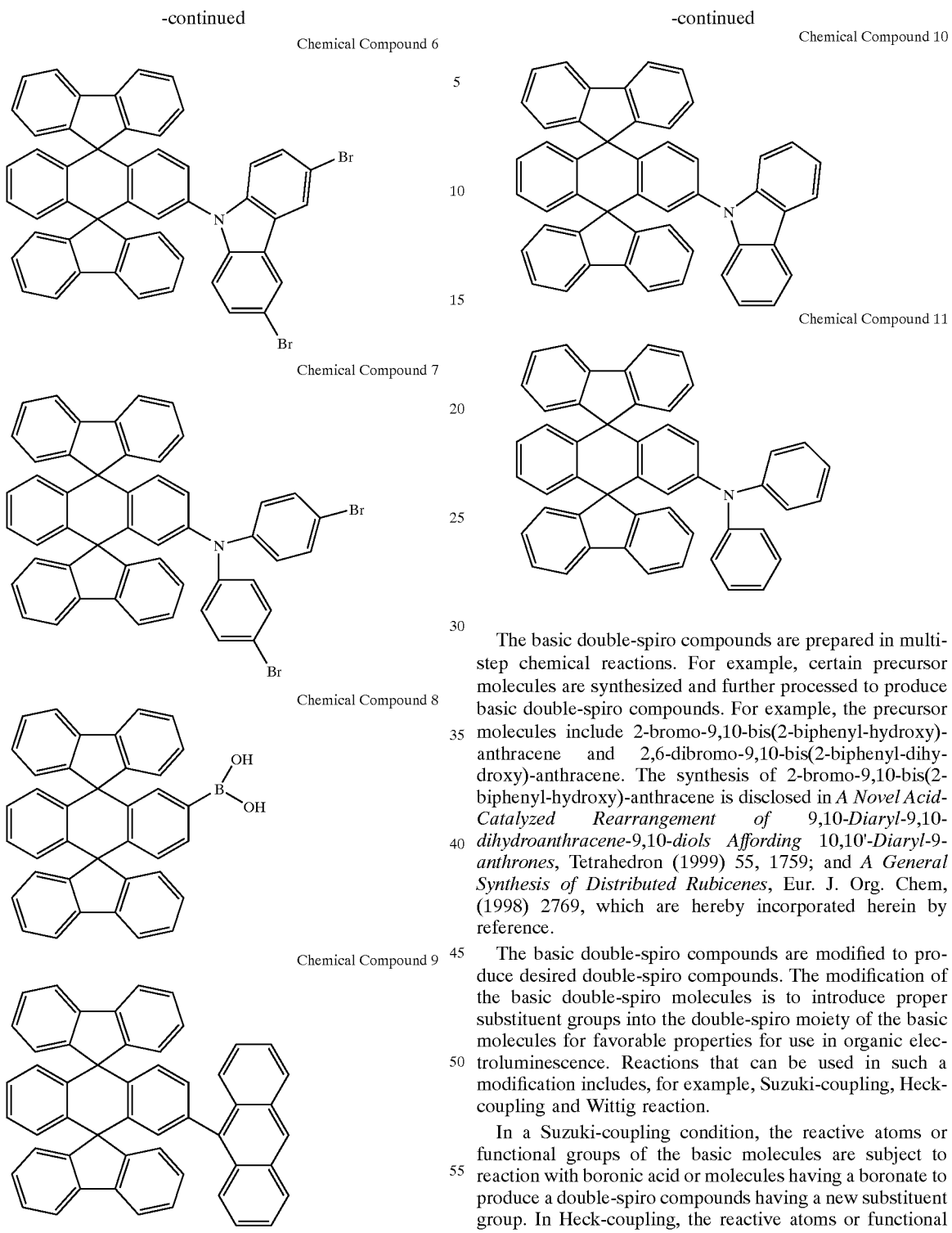

The basic double-spiro compounds are prepared in multi-step chemical reactions. For example, certain precursor molecules are synthesized and further processed to produce basic double-spiro compounds. For example, the precursor molecules include 2-bromo-9,10-bis(2-biphenyl-hydroxy)-anthracene and 2,6-dibromo-9,10-bis(2-biphenyl-dihydroxy)-anthracene. The synthesis of 2-bromo-9,10-bis(2-biphenyl-hydroxy)-anthracene is disclosed in *A Novel Acid-Catalyzed Rearrangement of 9,10-Diaryl-9,10-dihydroanthracene-9,10-diols Affording 10,10'-Diaryl-9-anthrones*, Tetrahedron (1999) 55, 1759; and *A General Synthesis of Distributed Rubicenes*, Eur. J. Org. Chem, (1998) 2769, which are hereby incorporated herein by reference.

The basic double-spiro compounds are modified to produce desired double-spiro compounds. The modification of the basic double-spiro molecules is to introduce proper substituent groups into the double-spiro moiety of the basic molecules for favorable properties for use in organic electroluminescence. Reactions that can be used in such a modification includes, for example, Suzuki-coupling, Heck-coupling and Wittig reaction.

In a Suzuki-coupling condition, the reactive atoms or functional groups of the basic molecules are subject to reaction with boronic acid or molecules having a boronate to produce a double-spiro compounds having a new substituent group. In Heck-coupling, the reactive atoms or functional groups are reacted with compounds containing atoms for nucleophilic substitution, such as nitrogen and sulfur, to produce double-spiro compounds having substituent groups linked by a non-carbon atom. Also, under a Heck-coupling condition, basic double-spiro molecules can be reacted with compounds containing vinyl groups to obtain double-spiro molecules substituted with olefinic groups. Alternatively, double-spiro molecules having olefinic substituent groups can be produced by reacting basic double-spiro molecules with compounds containing a carbonyl group such as an aldehyde under a Wittig reaction condition. The synthesis of various double-spiro organic compounds will be further discussed in Examples 1–33.

Organic EL Devices

The present inventors have developed organic EL devices using organic compounds having one or more double-spiro structures. As discussed above, many double-spiro organic compounds have light-emitting property and other properties favorable for use in organic EL devices, including hole injection, hole transportation, electron transportation and electron injection. Various organic EL devices can be constructed with the double-spiro organic compounds of the present invention in combination with any other compounds having characteristics and properties for use in the organic EL devices. Further, some of the double-spiro organic compounds of the present invention have more than one function in the process of organic electroluminescence. With these multi-functional organic EL compounds, further various constructions of organic EL devices can be available.

General Construction of Organic EL Devices

Now constructions for organic EL devices of the present invention will be discussed with reference to the accompanying drawings. FIGS. 1–6 illustrate various examples of organic EL device constructions composed of a plurality of layers. In these drawings, the same reference numbers are used to indicate like components between the embodiments. The term "layer" in these illustrations refers to a thin film deposit of one or more compounds. These exemplary constructions are not exhaustive variants of the organic EL devices in accordance of the present invention.

The constructions of the organic EL device of the present invention include a substrate 1, an anode 3, a cathode 15 and one or more layers located between the anode 3 and the cathode 15, as illustrated in FIGS. 1–6 although not limited thereto. Advantageously, the one or more intervening layers contain at least one of the instant double-spiro organic compound. Preferably, the double-spiro compounds contained in the one or more intervening layers satisfy General Formula 1. The one or more intervening layers include a hole-injecting layer 5, a hole-transporting layer 7, a light-emitting layer 9, an electron-transporting layer 11, an electron-injecting layer 13 and combinations of more than one of these layers.

The substrate 1 (FIGS. 1–6) supports the laminated structure of the organic EL device 10. The anode 3 (FIGS. 1–6) and cathode 15 (FIGS. 1–6) are electrically connected to an electric power source 17 (FIGS. 1–6) via a switch 19 (FIGS. 1–6), which is controlled by a controller (not shown). The hole-injecting layer 5 (FIGS. 1–3) facilitates the injection of holes from the anode 3 into the hole-transporting layer 7 (FIGS. 1–5). Similarly, the electron-injecting layer 13 (FIGS. 1 and 4) facilitates the injection of electrons from the cathode 15 into the electron-transporting layer 13. The hole-transporting layer 7 accelerates the movement of holes away from the anode 3 or hole-injecting layer 5 into, for example, the light-emitting layer 9 (FIGS. 1–6). The electron-transporting layer 11 (FIGS. 1, 2, 4 and 5) accelerates the movement of electrons away from the cathode 15 or the electron-injecting layer 13 into, for example, the light-emitting layer 9 (FIGS. 1–6).

The transferred holes and electrons recombine and form excitons at light emitting molecules in the light-emitting layer 9. The excitons transfer the energy of the recombination to the light-emitting molecules or to other light-emitting molecules, which release the transferred energy in the form of visible light. The one or more intervening layers, although not further indicated or discussed, may be multi-functional. A multi-functional layer has functions of, for example, hole injection and transportation; electron injection and transportation; hole transportation and light emission; electron transportation and light emission; hole injection, hole transportation and light emission; electron injection, electron transportation and light emission; and so forth. Such multi-functional layers can be made of a material having multi-functional properties with or without doping of other functional materials. In the alternative such layers are made of a mixture of more than one material having different functional properties still with or without doping of other functional materials.

Substrate

As mentioned above, the substrate 1 provides a support on which the laminated construction of the organic EL device can be build. Also, the substrate 1 functions as a protective layer for the construction of the organic EL device once manufactured. Thus, materials for the substrate 1 are selected from those which can stand the conditions of manufacturing processes and usage of the organic EL devices. In some organic EL device constructions of the present invention, the light emitted from the one or more intervening layers 5, 7, 9, 11 and 13 pass through the substrate 1. In such constructions, the substrate 1 is advantageously made of a transparent material to allow the visible light emitted from the light-emitting layer 9 to pass through. Transparent materials, which can be used for the substrate 1, for example, include glass, quartz and any other appropriate artificial materials such as transparent plastics. Preferably, glass is used for the substrate 1. In other constructions of organic EL devices of the present invention, the light can be emitted through the cathode 15 or any directions other than through the substrate 1. In such constructions, the substrate 1 is advantageously made of highly reflective material satisfying thermodynamic and mechanical requirements for depositing the anode 3 thereon. For example, semiconductor wafers, metal oxide, ceramic materials, and non-transparent plastics can be used as the substrate 1. A transparent substrate coated with a reflective material can also be used.

Anode

The anode 3 is a conductive electrode electrically connected to an electric power source. The anode 3 requires a relatively large work function, advantageously greater than 4 eV. For example, conductive materials, which can be used for the anode 3, include carbon; aluminum, vanadium, chromium, copper, zinc, silver, gold, similar metals, and alloys of the foregoing metals; zinc oxide, indium oxide, induim tin oxide (hereinafter referred to as "ITO"), indium zinc oxide and similar tin oxide or tin oxide indium-based complex compounds; mixtures of oxides and metals, such as ZnO:Al, $SnO_2$:Sb; and conductive polymers, such as poly (3-methylthiophene), poly[3,4-(ethylene-1,2-dioxy) thiophene], polypyrrole and polyaniline. Either transparent or non-transparent materials can be selected for the anode 3, depending upon the construction of the light passage in the organic EL device as discussed above in connection with the materials for the substrate 1. Preferably, the anode 3 is made of ITO. Although not illustrated, the anode 3 may be constructed in multiple layers of materials. The thickness of the anode 3 may vary depending on the materials used and its layered structures. However, the anode 3 is advantageously from about 10 nm to about 1000 nm, preferably from about 10 nm to about 500 nm.

Cathode

The cathode 15 requires a relatively small work function, advantageously smaller than 4 eV. For example, conductive materials, which can be used for the cathode 15, include magnesium, calcium, sodium, potassium, titanium, indium, yttrium, lithium, gadolinium, aluminum, silver, tin, lead, similar metals, and alloys of foregoing metals. Although not illustrated, the cathode 15 may be constructed in multiple layers of materials, such as LiF/Al and $Li_2O/Al$. Preferably, the cathode 15 is made of aluminum-lithium alloy, LiF/Al or $Li_2O/Al$. Either transparent or non-transparent materials may be used for the cathode 3, depending upon the construction of the light passage in the organic EL device as discussed above. The thickness of the cathode 15 may vary depending on the materials used and its layered structures. However, the cathode 15 is laminated advantageously from about 1 nm to about 10,000 nm, preferably from about 5 nm to about 5,000 nm.

Hole-Injecting Layer

The hole-injecting layer 5 has the function of enabling a large number of holes to be injected from the anode 3 at a low electric field applied to the device. The hole-injecting layer 5 advantageously is formed in the cases either where the interfacial strength between anode layer 3 and hole-transporting layer 7 is not strong enough or where the work function of the anode material is significantly different from the highest occupied molecular orbital (HOMO) level of the material of its neighboring layer 7, 9, 11 or 13. The HOMO level of the hole-injecting material is advantageously located between the work function of the anode 3 and the HOMO level of the other neighboring layer 9, 11 or 13, preferably near the middle of the two. Also, the hole-injecting material is preferred to be transparent when the construction of the organic EL device allows the light emission through the substrate 1. In otherwise constructions, the hole-injecting material is advantageously non-transparent.

In accordance with the organic EL devices of the present invention, the hole-injecting layer 5 can be made of one or more of the double-spiro structured compounds. Preferably, the double-spiro compounds are of General Formula 1. More preferably, the hole-injecting layer 5 includes one or more of the Chemical Compounds 300–308 and 400–413, most preferably, Chemical Compounds 300–308. In accordance with the organic EL devices of the present invention, one or more non-double-spiro hole-injecting materials may be added. Also, the hole-injecting layer 5 can be formed with one or more non-double-spiro hole-injecting materials as long as at least one double-spiro compound is used in the organic EL device. The non-double-spiro hole-injecting materials include, for example, metal porphyrine (U.S. Pat. Nos. 4,720,432 and 4,356,429); oligothiophene (U.S. Pat. No. 5,540,999); arylamines and derivatives thereof (U.S. Pat. Nos. 5,256,945, 5,609,970, and 6,074,734, and Japanese Unexamined Patent Publications 1999–219788 and 1996–269445); hexanitrile hexaazatriphenylene; conductive polymers such as derivatives of polyaniline, polythiophene with or without acid dopant; derivatives of quinacridone; derivatives of perylene (U.S. Pat. No. 5,998,803); and anthraquinone (Japanese Unexamined Patent Publication 2000–058267.) The referenced U.S. patents and Japanese publications are hereby incorporated herein by reference.

Hole-Transporting Layer

The hole-transporting layer 7 has the function to smoothly transfer the holes from the hole-injecting layer 5 or from anode 3 (in the absence of the hole-injecting layer 5) toward the light-emitting layer 9 or toward an area where light-emitting materials are doped. Materials good for use in the hole-transporting layer 7 are those having high hole mobility therein. This hole-transporting layer 7 also has the function of blocking electrons from its neighboring layer 9, 11, or 13 on the side of the cathode 15. Further, the hole-transporting layer 7 functions for both the hole injection and hole transportation in the constructions which do not have a separate hole-injecting layer.

In accordance with the organic EL devices of the present invention, the hole-transporting layer 7 can be made of one or more of the double-spiro structured compounds. The double-spiro compounds are preferably of General Formula 1. More preferably, the hole-transporting layer 7 includes one or more of the Chemical Compounds 300–308 and 400–413. In accordance with the organic EL devices of the present invention, one or more non-double-spiro hole-transporting materials may be added. Also, the hole-transporting layer 7 can be formed with one or more non-double-spiro hole-transporting materials as long as at least one double-spiro compound is used in the organic EL device. The non-double-spiro hole-transporting materials include, for example, arylamine derivatives, conjugated poylmers, block co-polymers with conjugated and non-conjugated repeating units, and the like. Advantageously, derivatives of the arylamine, 4,4'-bis[N-(1-naphthyl)-N-phenylamino] biphenyl (NPB) is used for the hole-transporting layer 7.

Electron-Transporting Layer

The electron-transporting layer 11 contains an electron transfer material to transfer the electron injected from the electron injecting layer 13 or from the cathode 15 (in the absence of the electron-injecting layer 13) to the light-emitting layer 9 or to an area where a light-emitting material is doped. Compounds having high electron mobility is used as an electron-transporting material. The electron-transporting layer 11 may also have the function of blocking holes to move thereinto. In the construction without a separate electron-injecting layer, the electron-transporting material is selected from those which can enable a large number of electron to be injected from the cathode 15 at a low electric field applied across the device.

In accordance with the organic EL devices of the present invention, the electron-transporting layer 11 can be made of one or more of the double-spiro structured compounds. Preferably, the double-spiro compounds are of General Formula 1. More preferably, the electron-transporting layer 11 includes one or more of the Chemical Compounds 200–222. In accordance with the organic EL devices of the present invention, one or more non-double-spiro electron-transporting materials may be added. Also, according to the organic EL devices of the present invention, the electron-transporting layer 11 can be formed with one or more non-double-spiro electron-transporting materials as long as at least one double-spiro compound is used in the organic EL device. The non-double-spiro electron-transporting materials include, for example, aluminum complexes of 8-hydroxyquinoline; organometallic complex compounds including Alq3 (U.S. Pat. No. 5,061,569 and U.S. patent application Ser. No. 09/540837); organic radical compounds (U.S. Pat. No. 5,811,833); hydroxyflavon-metal complexes (U.S. Pat.

Nos. 5,817,431 and 5,516,577, Japanese Unexamined Patent Publications 2001-076879, 2001-123157 and 1998-017860, and *Organic Light-emitting Diodes using 3- or 5-hydroxyflavone-metal Complexes*, Appl. Phys. Lett. 71 (23), 3338 (1997).) The referenced documents are hereby incorporated herein by reference.

Electron-Injecting Layer

The electron-injecting layer 13 is generally to faciliate injection of a large number of electrons from the cathode 15 at a low electric field applied across the device. The electron-injecting layer 13 is provided when the work function of the cathode 15 significantly differs from the lowest unoccupied molecular orbital (LUMO) level of the other neighboring layer 5, 7, 9 or 11. The electron-injecting layer 13 may be introduced to prevent excitons generated in the neighboring layer 5, 7, 9 or 11 from moving toward the cathode layer 15. In the alternative or in addition, the electron-injecting layer 13 may be provided to avoid damaging the neighboring layer 5, 7, 9 or 11 in the course of the deposition of the cathode layer 15. The LUMO level of the electron-injecting material is advantageously located between the work function of the cathode material and the LUMO level of the other neighboring layer 5, 7, 9 or 11, preferably near the middle of the two. Further, the electron-injecting layer 13 is required to have strong interface with the cathode layer 15.

In accordance with the organic EL devices of the present invention, the electron-injecting layer 13 can be made of one or more of the double-spiro structured compounds. Preferably, the double-spiro compounds are of General Formula 1. More preferably, the electron-injecting layer 13 includes one or more of the Chemical Compounds 200–222. In accordance with the organic EL devices of the present invention, one or more non-double-spiro electron-injecting materials may be added. Also, according to the organic EL devices of the present invention, the electron-injecting layer 13 can be formed with one or more non-double-spiro electron-injecting materials as long as at least one double-spiro compound is used in the organic EL device. The non-double-spiro electron-injecting materials include, for example, aluminum complexes of 8-hydroxyquinoline, organometallic complex compounds including Alq3, organic radical compounds (U.S. Pat. No. 5,811,833); 3- or 5-hydroxyflavone-metal complexes (*Organic Light-emitting Diodes using 3- or 5-hydroxyflavone-metal Complexes*, Appl. Phys. Lett. 71 (23), 3338 (1997)); the electron-injecting compounds disclosed in Japanese Unexamined Patent Publications 2001-076879, 2001-123157 and 1998-017860; poly(p-phenyleneethylene), poly(triphenyldiamine), and spiroquinoxaline (*Polymeric Light-Emitting Diodes Based on Poly(p-phenyleneethylene), Poly(triphenyldiamine), and Spiroquinoxaline*, Adv. Funct. Mater. 11, 41, (2001)); the electron-injecting compounds disclosed in *High-efficiency oligothiophene-based light-emitting diodes*, Appl. Phys. Lett. 75, 439 (1999); the electron-injecting compounds disclosed in *Modifiede Oligothiophenes with High Photo-and Electroluminescence Efficiencies*, Adv. Mater. 11, 1375 (1999). The referenced documents are hereby incorporated herein by reference.

Light-Emitting Layer

The light-emitting layer 9 is a layer particularly dedicated to the emission of visible light by the process of recombination of electrons and holes therein although it may have other functions as well. Advantageously, the light-emitting layer 9 of the organic EL devices is composed of one light-emitting material alone or a mixture of two or more light-emitting materials without doping. In an alternative construction, the light-emitting layer 9 is composed of one or more light-emitting host materials and a small amount of one or more dopants, as will be discussed below.

In accordance with the organic EL devices of the present invention, the light-emitting layer 9 can include one or more of the instant double-spiro structured compounds. Preferably, the double-spiro compounds are of General Formula 1 as a light-emitting material. More preferably, the light-emitting layer 9 includes one or more of the Chemical Compounds 100–137, 200–222, and 400–413. In accordance with the organic EL devices of the present invention, these double-spiro compounds can be used as a host or as a dopant. In either case, one or more non-double-spiro light-emitting materials may be added as either another host material or another dopant. Advantageously, the double-spiro compounds are used as a host material, with or without another host material, for hosting one or more fluorescent or phosphorescent dopants. Also, according to the organic EL devices of the present invention, the light-emitting layer 9 may include one or more non-double-spiro light-emitting materials as long as at least one double-spiro compound is used in the organic EL device. The non-double-spiro light-emitting materials include, for example, 8-hydroxyquinoline metal complexes including Alq3; carbazole compounds and derivatives thereof; dimerized styryl compounds (U.S. Pat. No. 5,366,811); BAlq (U.S. Pat. No 5,150,006); 10-hydroxybenzo[h]quinoline-metal complexes (U.S. Pat. No. 5,529,853); 2-( 2'-hydroxy-5'methylphenyl)benzotriazole metal complexes (U.S. Pat. No. 5,486,406); benzoxazole, benzthiazole, benzimidazole and derivatives thereof (U.S. Pat. No. 5,645,948); poly(p-phenylene vinylene) and derivatives thereof (*Conjugated Polymers as Solid-State Laser Materials*, Synthetic Metals 91, 35 (1997); and *Low Voltage Operation of Large Area Polymer LEDs*, Synthetic Metals 91, 109 (1997)); spiro compounds (U.S. Pat. No. 5,840,217); polyfluorene, rubrene or the like. The referenced documents are hereby incorporated herein by reference.

Doping

According to the organic EL devices of the present invention, the light-emitting layer 9 may be constructed with or without a dopant. Dopants are introduced to improve the light-emission efficiency, to tune the color of the emission, and/or to simply emit light from a layer having a non-fluorescent host. Dopants can be added to the light-emitting layer 9 and one or more of the other layers 5, 7, 11 and 13. More than one light-emitting material can be doped together in these layers for various purposes. Also, in some constructions of the organic EL devices according to the present invention, the light-emitting layer 9 may be absent. In such constructions, one or more light-emitting dopants are necessarily put in one or more of the layers 5, 7, 11 or 13 to generate visible light therefrom.

Generally, dopants are selected from fluorescent or phosphorescent materials having higher quantum efficiency than the host material. Preferably, the dopants have a quantum yield close to "1" in a dilute system. This means that most of the energy received from excitons contributes to the light emission rather than releasing it in other forms such as generating heat. Also, dopants are selected such that they match energetically with the host material. In other words, excitons are known to have a tendency to transfer their energy to a material having a smaller band gap among materials near the recombination location; thus, dopants are advantageously selected from the light-emitting materials having a band gap slightly smaller than that of the host materials. Depending upon the matching of the dopants and host materials, recombination may occur in the host molecules, and the energy of the generated excitons is transferred to the dopants. In this case, visible light is emitted from the dopant molecules. Also, the energy of the excitons may be transferred to another dopant, where the light is emitted. In the alternative, the recombination and light emission may occur in one light-emitting material.

Advantageously, the double-spiro light-emitting compounds can be used as a dopant in various layers. Preferably, these dopants have the double-spiro structure of General Formula 1. For example, Chemical Compounds 100–137, 200–222 and 400–413 can be used as a dopant light-emitting material. One or more double-spiro dopants can be used with or without other dopants. Whether or not a separate light-emitting layer is provided, quantum efficiency and lifetime of the organic EL device can be enhanced by selecting an appropriate host materials, one or more matching dopants and their concentrations.

Other light-emitting (phosphorescent or fluorescent) materials for doping in the organic EL devices of the present invention include, for example, perylene, rubrene, coumarine, quinacridone, nile red, DCM, and the following organometallic complexes.

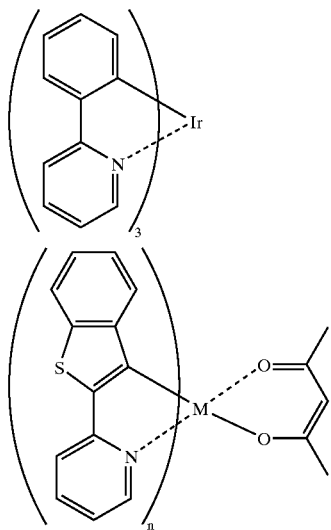

Some of the exemplified and additional materials for use as dopants, either fluorescent or phosphorescent, are disclosed in *Organic Light-Emitting Devices With Saturated Red Emission Using 6,13-Diphenylpentacene*, Appl. Phys. Lett. 78, 2378 (2001); *Photoluminescence and Electroluminescence Properties of Dye-Doped Polymer System*, Synthetic Metals 91, 335 (1997); *Fabrication of Highly Efficient Organic Electroluminescent Devices*, Appl. Phys. Lett. 73, 2721 (1998); *Organic Electroluminescent Devices Doped With Condensed Polycyclic Aromatic Compounds*, Synthetic Metals 91, 27 (1997); *Bright Blue Electroluminescent Devices Utilizing Poly (N-Vinylcarbazole) Doped With Fluorescent Dye*, Synthetic Metals 91, 331 (1997); *Doped Organic Electroluminescent Devices With Improved Stability*, Appl. Phys. Lett. 70, 1665 (1997); *Stability Characteristics Of Quinacridone and Coumarine Molecules as Guest Dopnats in The Organic Leds*, Synthetic Metals 91, 15 (1997); *Strongly Modified Emission From Organic Electroluminescent Device With a Microcavity*, Synthetic Metals 91, 49 (1997); *Organic Light-Emitting Diodes Using a Gallium Complex*, Appl. Phys. Lett. 72, 1939 (1998); *Orange and Red Orgnanic Light-Emitting Devices Using Aluminum Tris (5-Hydroxyquinoxaline)*, Synthetic Metals 91, 217 (1997); *Synthesis and Characterization of Phosphorescent Cyclometalated Iridium Complexes*, Inorg. Chem. 40, 1704 (2001); *Highly Phosphorescent Bis-Cyclometalated Iridium Complexes*, J. Am. Chem. Soc. 123, 4304, (2001); *High Quantum Efficiency in Organic Light-Emitting Devices with Iridium-Complex as Triplet Emissive Center*, Jpn. J. Appl. Phys. 38, L1502 (1999); *Optimization of Emitting Efficiency in Organic LED Cells Using Ir Complex*, Synthetic Metals 122, 203 (2001); *Operating lifetime of phosphorescent organic light emitting devices*, Appl. Phys. Lett. 76, 2493 (2000); *High-Efficiency Red Electrophosphorescence Devices*, Appl. Phys. Lett. 78, 1622 (2001); *Very High-Efficiency Green Organic Light-Emitting Devices Based on Electrophosphorescence*, Appl. Phys. Lett. 75, 4 (1999); *Highly-Efficient Organic Electrophosphorescent Devices With Tris( 2-Phenylpyridine)Iridium Doped Into Electron-Transporting Materials*, Appl. Phys. Lett. 77, 904 (2000); and *Improved Energy Transfer In Electrophosphorescent Devices*, Appl. Phys. Lett. 74, 442 (1999), all of which are hereby incorporated herein by reference.

Other various aspects and features of the double-spiro compounds and organic EL devices in accordance with the present invention will be further discussed in terms of the following examples, which are intended to illustrate the present invention but not limit the scope.

EXAMPLES OF SYNTHESIS

Example 1

Synthesis of Chemical Compound 1

To a solution of 2-bromobiphenyl (9.00 ml, 52.0 mmol) in THF (100 ml) was added dropwise t-BuLi (40 ml of a 1.7 M solution in pentane) at −78° C. under nitrogen. After the mixture had been stirred for 40 min, 2-bromoanthraquinone (5.00 g, 17.0 mmol) was added at −78° C. The cooling bath was removed and the mixture was stirred for 3 hours at room temperature. The reaction mixture was poured into diethyl ether (150 ml) and 2 N HCl (150 ml), and stirred for 40 min at room temperature. The precipitate was filtered off with suction, washed with water and ethyl ether, and then dried to obtain 2-bromo-9,10-bis( 2-biphenyl-hydroxy)-anthracene (9.50 g, 92%).

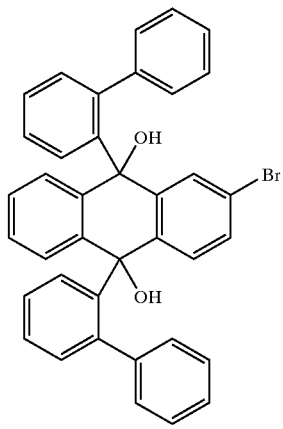

2-bromo-9,10-bis(2-biphenyl-dihydroxy)-anthracene 9.50 g (16.0 mmol) of 2-bromo-9,10-bis(2-biphenyl-hydroxy)-anthracene synthesized as above was suspended in acetic acid (150 ml), and conc. $H_2SO_4$ (20 drops) was added thereto. After the reaction mixture had been stirred at reflux for about 3 hours, it was cooled to room temperature. The precipitate was filtered off with suction, washed with acetic acid, water, and ethanol. Purification by sublimation afforded Chemical Compound 2 (8.0 g, 89%) as white solid: mp 419.7° C.; $^1$H NMR (500 MHz, DMSO-$d_6$) δ 8.12 (dd, J=7.4, 7.3 Hz, 4H), 7.53–7.47 (m, 4H), 7.39–7.34(m, 4H), 7.25 (t, J=8.0 Hz, 4H), 7.06 (dd, J=2.3, 8.7 Hz, 1H), 6.86–6.81 (m, 2H), 6.29 (d, J=2.3 Hz, 1H), 6.26–6.21 m, 2H), 6.20 (d, J=8.7 Hz, 1H); MS (M+) calculated for $C_{38}H_{23}Br$ 558, found 558; analysis calculated for $C_{38}H_{233}Br$: C, 81.58; H, 4.14; Br, 14.28. Found: C, 82.00; H, 4.14; Br, 13.86.

Example 2

Synthesis of Chemical Compound 2

To a solution of 2-bromobiphenyl (8.83 ml, 51.2 mmol) in THF (200 ml) was added dropwise t-BuLi (60 ml of a 1.7 M solution in pentane) at −78° C. under nitrogen. After the mixture had been stirred for 40 min, 2,6-dibromoanthraquinone (7.50 g, 20.5 mmol) was added at −78° C. The cooling bath was removed and the mixture was stirred for 15 hours at room temperature. The reaction mixture was poured into diethyl ether (200 ml) and 2 N HCl (200 ml), and stirred for 40 min at room temperature. The precipitate was filtered off with suction, washed with water and ethyl ether. After drying, 2,6-dibromo-9,10-bis(2-biphenyl-dihydroxy)-anthracene (11.8 g, 85%) was obtained.

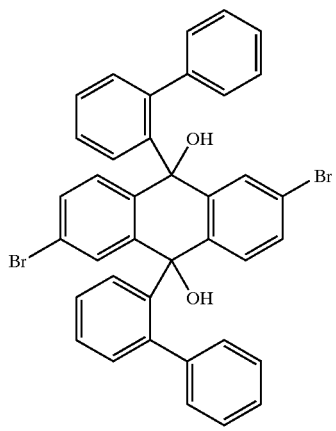

2,6-dibromo-9,10-bis(2-biphenyl-dihydroxy)-anthracene 10.5 g (15.57 mmol) of 2,6-dibromo-9,10-bis(2-biphenyl-hydroxy)-anthracene synthesized as above was suspended in acetic acid (150 ml), and conc. $H_2SO_4$ (20 drops) was added thereto. After the reaction mixture had been stirred while refluxing for about 15 hours, it was cooled to room temperature. The precipitate was filtered off with suction, washed with acetic acid, water, and ethanol. Purification by sublimation afforded Chemical Compound 2 (9.0 g, 90%) as white solid: mp 478.1° C.; $^1$H NMR (300 MHz, CDCl$_3$) δ 7.92 (d, J=7.6 Hz, 4H), 7.46 (t, J=8.0 Hz, 4H), 7.33 (t, J=7.4 Hz, 4H), 7.21 (d, J=7.6 Hz, 4H), 6.88 (dd, J=2.1, 8.6 Hz, 2H), 6.47 (d, J=2.1 Hz, 2H), 6.22 (d, J=8.6 Hz, 2H); MS (M+) calculated for $C_{38}H_{22}Br_2$ 636, found 636; analysis calculated for $C_{38}H_{22}Br_2$: C, 71.50; H, 3.47; Br, 25.03. Found: C, 71.90; H, 3.40; Br, 25.7.

Example 3

Synthesis of Chemical Compound 3

To a solution of 2-methylanthraquinone (16.0 g, 72.0 mmol) in a mixture of acetic acid (400 ml) and acetic anhydride (400 ml) was added concentrated sulfuric acid (16 ml) at 5° C. Chromium trioxide (18.0 g, 0.18 mmol) was added over a period of 1 hour at 5° C. The reaction mixture was then stirred at 5° C. for 4 hours, poured into ice water, and extracted with chloroform. The organic extract was dried over MgSO$_4$ and concentrated under vacuum to give anthraquinone-2-aldehyde diacetate (16.0 g, 65%.) To a solution of the anthraquinone-2-aldehyde diacetate (16.0 g, 47.3 mmol) in acetic acid (400 ml) was added dropwise 35% aqueous hydrochloric acid (170 ml) at room temperature. The reaction mixture had been stirred while refluxing for 15 min, cooled to room temperature, filtered off with suction, and washed with water. After drying, anthraquinone-2-aldehyde (10.0 g, 89%) was obtained.

A mixture of anthraquinone-2-aldehyde (12.0 g), 1,3-propanediol (10 ml), and p-toluenesulfonic acid (20 mg) in toluene (300 ml) was heated under reflux with a removal of water formed from the condensation of anthraquinone aldehyde and 1,3-propane diol for 4 hours. The mixture was then cooled to room temperature, filtered off with suction, washed with water and diethyl ether, and dried under vacuum to afford anthraquinone-2-propaneacetal (12.5 g, 84%).

To a solution of 2-bromobiphenyl (9.3 ml, 54.0 mmol) in THF (80 ml) was added dropwise t-BuLi (45 ml of a 1.7 M solution in pentane) at −78° C. under nitrogen. After the mixture had been stirred for 1 hour, anthraquinone-2-propaneacetal (6.60 g, 22.4 mmol) was added at −78° C. The cooling bath was removed and the mixture was stirred for 1 h at room temperature. The mixture was poured into 1 N HCl and diethyl ether, and then stirred for 1 hour, precipitate formed was filtered off with suction, washed with diethyl ether, and dried under vacuum to give anthraquinol-2-propaneacetal (13.0 g, 93%).

To a solution of anthraquinol-2-propaneacetal (13.0 g, 21.5 mmol) in acetic acid (300 ml) was added concentrated sulfuric acid (5 drops). The reaction mixture had been stirred while refluxing for 3 hours, it was cooled to room temperature. The precipitate was filtered off with suction, washed with water, ethanol, and diethyl ether, and dried under vacuum to afford Chemical Compound 3 (10.0 g, 91%) as white solid: mp 428.5° C.; $^1$H NMR (300 MHz, CDCl$_3$) δ 9.53 (s, 1H), 8.15–8.13 (m, 4H), 7.52–7.23 (m, 13H), 6.85–6.82 (m, 2H), 6.79 (s, 1H), 6.45 (d, J=8.2 Hz, 1H), 6.26–6.22 (m, 2H).

Example 4

Synthesis of Chemical Compound 8

For the coupling of the halogen containing precursor molecules to prepare appropriately substituted double-spiro compounds, the halogen of Chemical Compound 1 was converted into a boronic acid group as in Chemical Compound 8.

To a solution of Chemical Compound 1 (10.0 g, 17.9 mmol), in dry THF (150 ml) was added dropwise t-BuLi (31.5 ml of a 1.7 M solution in pentane) at −78° C. under nitrogen. After the mixture had been stirred for 1 hour, trimethylborate (8.00 ml, 71.5 mmol) was added dropwise at −78° C. The cooling bath was removed and the mixture was stirred for 3 hours at room temperature. The mixture was quenched with 2 N HCl (100 ml) and stirred for 1 hour at room temperature. The precipitate was filtered with suction and washed with water. The crude product was slurried in diethyl ether, stirred while refluxing , filtered off with suction, and dried under vacuum at 50° C. After drying, double-spiro boronic acid of Chemical Compound 8 (7.60 g, 81%) was obtained, and used for the Suzuki-coupling reaction without further purification Example 5

Synthesis of Chemical Compound 100

To a solution of Chemical Compound 3 (1.34 g, 2.6 mmol) and 4,4'-bis(diethylphosphorylmethyl)biphenyl (0.50 g, 1.3 mmol) in DMF (80 ml) was added dropwise lithium ethoxide (2.8 ml of a 1.0 M solution in ethanol) at room temperature under nitrogen. After the reaction mixture had been stirred at room temperature for 12 hours, it was filtered off with suction, washed with ethanol and dried under vacuum. Purification by sublimation afforded Chemical Compound 100 (1.00 g, 66%) as white solid: mp >500° C.; $^1$H NMR is not listed because of insolubility of Chemical Compound 100 in common solvents. MS (M+) calculated for $C_{90}H_{56}$ 1136, found 1136; analysis calculated for $C_{90}H_{56}$: C, 95.04; H, 4.96. Found: C, 94.88; H, 5.12.

Example 6

Synthesis of Chemical Compound 102

To a suspension of 9,10-dibromoanthracene (60 mg 0.19 mmol), Chemical Compound 8 (0.20 g, 0.38 mmol), and potassium phosphate (0.16 g, 0.76 mmol) in DMF (10 ml) was added tetrakis(triphenylphosphine)palladium (12 mg, 0.01 mmol) under nitrogen. After the reaction mixture had been stirred at 60° C. for 18 hours, it was cooled to room temperature and ethanol (20 ml) was added. After addition, the reaction mixture was further stirred at room temperature for 30 minutes. The precipitate was filtered off with suction, washed with water, ethanol, and acetone, and dried under vacuum. Then it was dissolved in N-methyl pyrrolidine (50 ml) and filtered through a short column packed with silica gel. After removal of solvent, the crude product was purified by crystallizing from ethanol to give Chemical Compound 102 (0.16 g, 41%): mp >500° C.; $^1$H NMR is not listed because of insolubility of 100 in common solvents. MS (M+) calculated for $C_{90}H_{54}$ 1134, found 1134; analysis calculated for $C_{90}H_{54}$: C, 95.21; H, 4.79. Found: C, 94.90; H, 4.70.

Example 7

Synthesis of Chemical Compound 103

To a suspension of Chemical Compound 1 (0.50 g, 0.89 mmol), 1-vinylpyrene (0.25 g, 1.07 mmol), and triethylamine (1.5 ml, 10.8 mmol)) in DMF (8 ml) were added Pd(OAc)2 (11 mg, 0.05 mmol) and tri-o-tolylphosphine (70 mg, 0.23 mmol). After the reaction mixture had been stirred while refluxing for 15 hours, it was cooled to room temperature, quenched with water (40 ml), and extracted with dichloromethane (3×40 ml). The combined organic extracts were dried over $MgSO_4$ and concentrated under vacuum. Purification by column chromatography (1:2 dichloromethane-hexane) and recrystillization from THF and ethanol afforded Chemical Compound 103 (0.2 g, 32%) as yellow solid: mp 430.0° C.; $^1$H NMR (300 MHz, $CDCl_3$) δ 8.18–7.70 (m, 14H), 7.47–7.25 (m, 14H), 6.90–6.78 (m, 2H), 6.52–6.41 (m, 4H); MS (M+) calculated for $C_{56}H_{34}$ 706, found 706; analysis calculated for $C_{56}H_{34}$: C, 95.15; H, 4.85. Found: C, 95.10; H, 4.66.

Example 8

Synthesis of Chemical Compound 105

To a solution of 1,1'-diphenylethylene (7.80 g, 43.3 mmol) in carbon tetrachloride (250 ml) in dark atmosphere was added dropwise bromine (2.45 ml) in carbon tetrachloride (5 ml) at −15° C. The reaction mixture was stirred at room temperature for 1 hour and silica gel (SiO2, 1.0 g), which was activated at 140° C. for 15 h, was added. After the mixture had been stirred while refluxing for 1 hour, it was cooled to room temperature. After removal of the solvent, the residue was dissolved with n-hexane and filtered through a short column packed with silica gel. Recrystallization from n-hexane afforded 2,2'-diphenylvinyl-1-bromide (10.6 g, 95%) as ivory crystal.

To a solution of 2,2'-diphenylvinyl-1-magnesium bromide, which was freshly prepared from 2,2'-diphenyl-1-bromide (2.00 g, 7.72 mmol) in THF (30 ml) and magnesium (0.23 g, 9.24 mmol) with iodomethane (3 drops) as an initiator, was added dropwise trimethylborate (2.63 ml, 23.16 mmol) in THF (6 ml) at −78° C. under nitrogen. After the mixture had been stirred at room temperature for 3 hours, it was poured into a mixture of 2 N HCl (40 ml) and diethyl ether (200 ml). The organic layer was separated, dried over $MgSO_4$, and concentrated under vacuum. Chemical Compound 2 (0.36 g, 0.75 mmol), 2,2'-diphenylvinyl-1-boronic acid, and tetrakis(triphenylphosphine)palladium (86 mg, 0.075 mmol) were slurried in a mixture of toluene (20 ml) and aqueous potassium carbonate solution (10 ml, 2 M). With vigorous stirring, the mixture was boiled under reflux for 10 hours. After cooling to room temperature, the organic layer was separated, washed with water, dried over $MgSO_4$, and concentrated under vacuum. Recrystallization from chloroform and ethanol afforded Chemical Compound 105 (0.42 g, 67%) as white solid: mp 387.7° C.; $^1$H NMR (300 MHz, $CDCl_3$) δ 7.44 (d, J=7.4 Hz, 4H), 7.37 (t, J=7.4 Hz, 4H), 7.23 (t, J=8.8 Hz, 4H), 7.14–6.98 (m, 20H), 6.81 (d, J= 8.0 Hz, 4H), 6.43 (s, 2H), 6.34 (d, J= 8.4 Hz, 2H), 6.10 (s, 2H), 6.01 (d, J=8.4 Hz, 2H); MS (M+) calculated for $C_{66}H_{44}$ 836, found 836; analysis calculated for $C_{66}H_{44}$: C, 94.70; H, 5.30. Found: C, 94.30; H, 5.40.

Example 9

Synthesis of Chemical Compound 107

To a solution of Chemical Compound 1 (1.20 g, 2.14 mmol), 4-( 2,2-diphenylvinyl)-phenylboronic acid (0.64 g, 2.14 mmol), and sodium carbonate (0.68 g, 6.42 mmol) in a mixture of toluene (30 ml), ethanol (6 ml), and water (15 ml) was added tetrakis(triphenylphosphine)palladium (50 mg, 0.04 mmol). The reaction mixture was stirred while refluxing for 12 hours. Then it was cooled to room temperature and water (50 ml) was added. The organic layer was separated and the aqueous layer was extracted with dichloromethane (3×50 ml). The combined organic extracts were dried over $MgSO_4$ and concentrated under vacuum. Recrystllization from chloroform and ethanol afforded Chemical Compound 107 (0.98 g, 62%) as colorless solid: mp 365.2° C.; $^1$H NMR ( 500 MHz, $CDCl_3$) δ 7.92 (dd, J=4.6, 7.4 Hz, 4H), 7.45–7.39 (m, 4H), 7.32–7.22 (m, 17H), 7.15–7.13 (m, 2H), 6.96 (dd, J=2.0, 8.5 Hz, 1H), 6.89 (s, 3H), 6.84 (s, 1H), 6.79–6.75 (m, 2H), 6.55 (d, J=2.0 Hz, 1H), 6.43–6.36 (m, 3H); MS (M+) calculated for $C_{58}H_{38}$ 734, found 734; analysis calculated for $C_{58}H_{38}$: C, 94.79; H, 5.21. Found: C, 94.98; H, 5.05.

Example 10

Synthesis of Chemical Compound 109

To a suspension of 9-bromo-10-phenylanthracene (0.3 g, 1.00 mmol), Chemical Compound 8 (0.52 g, 1.00 mmol), and potassium phosphate (0.42 g, 2.00 mmol)) in DMF (10 ml) was added tetrakis(triphenylphosphine)palladium (35 mg, 0.03 mmol) under nitrogen. After the reaction mixture had been stirred at 60° C. for 12 hours, it was cooled to room temperature. Ethanol (20 ml) was added to the mixture, and then the mixture was stirred for 30 minutes at room temperature. The precipitate was filtered off with suction, washed with water, ethanol, and acetone, and dried under vacuum. Then it was dissolved in chloroform (150 ml) and filtered through a short column packed with silica gel. After removal of solvent, the crude product was purified by crystallizing from ethanol to give Chemical Compound 109 (0.26 g, 35%): mp 448° C.; $^1$H NMR (400 MHz, N-methylpyrrolidine-$d_9$) δ 8.26 (d, J=7 Hz, 2H), 8.00 (dd, J=3.0, 7.0 Hz, 2H), 7.62–7.54 (m, 9H), 7.48–7.38 (m, 9H), 7.35–7.29 (m, 5H), 7.20–7.16 (m, 2H), 7.10 (dd, J=2.0, 8.0 Hz, 1H), 6.95–6.90 (m, 2H), 6.66 (d, J=8.0 Hz, 1H), 6.49 (d, J= 2.0 Hz, 1H), 6.42–6.39 (m, 2H); MS (M+) calculated for $C_{58}H_{36}$ 732, found 732; analysis calculated for $C_{58}H_{36}$: C, 95.05; H, 4.95. Found: C, 95.07; H, 4.88.

Example 11

Synthesis of Chemical Compound 110

To a suspension of 9-bromo-10-(2-naphtyl)-anthracene (1.00 g, 2.60 mmol), Chemical Compound 8 (1.36 g, 2.60 mmol), and potassium phosphate (1.10 g, 5.20 mmol)) in DMF (60 ml) was added tetrakis(triphenylphosphine)palladium (90 mg, 0.08 mmol) under nitrogen. After the reaction mixture was stirred at 70° C. for 12 hours, it was cooled to room temperature and ethanol (60 ml) was added. After addition, the reaction mixture was stirred at room temperature for 30 minutes. The precipitate was filtered off with suction, washed with water, ethanol, and acetone, and dried under vacuum. Then, it was dissolved in chloroform (450 ml) and filtered through a short column of silica gel. After removal of solvent, the crude product was purified by crystallizing from ethanol to give of Chemical Compound 110 (1.20 g, 58%): mp 423° C.; 1H NMR (400 MHz, CDCl 3) δ 8.00–7.96 (m, 4H), 7.84–7.81 (m, 2H), 7.76–7.71 (m, 2H), 7.58–7.33 (m, 19H), 7.18–7.06 (m, 4H), 6.97 (ddd, J=2.0, 4.0, 8.0 Hz, 1H), 6.85–6.80 (m, 2H), 6.65 (d, J= 8.0 Hz, 1H), 6.57 (dd, J= 2.0, 5.0 Hz, 1H), 6.50–6.45 (m, 2H); MS (M+) Calculated for $C_{62}H_{38}$ 782, found 782; analysis calculated for $C_{62}H_{38}$: C, 95.11; H, 4.89. Found: C, 95.20; H, 4.80.

Example 12

Synthesis of Chemical Compound 111

To a suspension of 9-bromo-10-(2-biphenyl) anthracene (0.4 g, 1.00 mmol), Chemical Compound 8 (0.52 g, 1.00 mmol), and potassium phosphate (0.42 g, 2.00 mmol)) in DMF (10 ml) was added tetrakis(triphenylphosphine)palladium (35 mg, 0.03 mmol) under nitrogen. After the reaction mixture had been stirred at 60° C. for 12 hours, it was cooled to room temperature and ethanol (20 ml) was added. After addition, the reaction mixture was stirred at room temperature for 30 minutes. The precipitate was filtered off with suction, washed with water, ethanol, and acetone, and dried under vacuum. Then, it was dissolved in chloroform (150 ml) and filtered through a short column of silica gel. After removal of solvent, the crude product was purified by sublimation to give Chemical Compound 111 (0.26 g, 35%): mp 475.5° C.; $^1$H NMR (400 MHz, $CDCl_3$) δ 7.97 (d, J=7.0 Hz, 2H), 7.81 (d, J=7.0 Hz, 1H), 7.74–7.70 (m, 2H), 7.56–7.20 (m, 18H), 7.14–7.10 (m, 2H), 7.00–6.70 (m, 11H), 6.58 (d, J=8.0 Hz, 1H), 6.53–6.42 (m, 3H); MS (M+) Calculated for $C_{64}H_{40}$ 808, found 808; analysis calculated for $C_{64}H_{40}$: C, 95.02; H, 4.98. Found: C, 95.14; H, 4.86.

Example 13

Synthesis of Chemical Compound 113

To a suspension of 9-bromo-10-(3,5-terphenyl)-anthracene (0.78 g, 1.50 mmol), Chemical Compound 8 (0.79 g, 1.50 mmol), and potassium phosphate (0.63 g, 3.00 mmol)) in DMF (25 ml) was added tetrakis(triphenylphosphine)palladium (52 mg, 0.05 mmol) under nitrogen. After the reaction mixture had been stirred at 70° C. for 12 hours, it was cooled to room temperature and ethanol (30 ml) was added. After the addition, the reaction mixture was stirred at room temperature for 30 minutes. The precipitate was filtered off with suction, washed with water, ethanol, and acetone, and dried under vacuum. Then, it was dissolved in chloroform (50 ml) and filtered through a short column of silica gel. After removal of the solvent, the crude product was purified by crystallizing from ethanol to give Chemical Compound 113 (0.75 g, 57%): mp 430.3° C.; $^1$H NMR (400 MHz, CDCl 3) δ 7.99–7.96 (m, 3H), 7.75–7.66 (m, 8H), 7.59 (dt, J=2.0, 10.0 Hz, 2H), 7.51–7.30 (m, 20H), 7.24–7.19 (m, 2H), 7.11–7.07 (m, 2H), 6.96 (dd, J=2.0, 8.0 Hz, 1H), 6.85–6.80 (m, 2H), 6.65 (d, J= 8.0 Hz, 1H), 6.57 (d, J=2.0 Hz, 1H), 6.50–6.45 (m, 2H); MS (M+) Calculated for $C_{70}H_{44}$ 884, found 884; analysis calculated for $C_{70}H_{44}$: C, 94.99; H, 5.01. Found: C, 95.03; H, 4.93.

Example 14

Synthesis of Chemical Compound 114

To a suspension of Chemical Compound 2 (0.33 g, 0.51 mmol), 10-phenyl-anthracene-9-boronic acid (0.53 g, 1.79 mmol), potassium phosphate (0.43 g, 2.00 mmol), and 2,6-di-t-butyl-4-methylphenol (80 mg, 0.36 mmol) in DMF (10 ml) was added tetrakis(triphenylphosphine)palladium (24 mg, 0.02 mmol) under nitrogen. The mixture was degassed with nitrogen for 1 hour. After the reaction mixture had been stirred at 65° C. for 17 hours, it was cooled to room temperature and ethanol (50 ml) was added. After addition, the reaction mixture was stirred at room temperature for 30 minutes. The precipitate was filtered off with suction, washed with water and ethanol, and dried under vacuum. Purification by sublimation afforded Chemical Compound 114 (60 mg, 12%) as white solid: mp >500° C.; $^1$H NMR is not listed because of insolubility of Chemical Compound 114 in common solvents. MS (M+) Calculated for $C_{78}H_{48}$ 984, found, 984; analysis calculated for $C_{78}H_{48}$: C, 95.09; H, 4.91. Found: C, 95.15; H, 4.85.

Example 15

Synthesis of Chemical Compound 116

To a suspension of 2-bromo-9,10-diphenylanthracene (0.41 g, 1.00 mmol), Chemical Compound 8 (0.79 g, 1.50 mmol), and potassium phosphate (0.64 g, 3.00 mmol)) in DMF (15 ml) was added tetrakis(triphenylphosphine)palladium (35 mg, 0.03 mmol) under nitrogen. The mixture was degassed with nitrogen for 30 minutes. After the reaction mixture had been stirred at 90° C. for 60 hours, it was cooled to room temperature and ethanol (60 ml) was added. After addition, the reaction mixture was stirred at room temperature for 30 minutes. The precipitate was filtered off with suction, washed with water and ethanol, and dried under vacuum. Purification by sublimation afforded Chemical Compound 116 (0.32 g, 40%) as white solid: mp 399.06° C.; $^1$H NMR (500 MHz, CDCl$_3$) δ 7.90 (dd, J=7.0, 13.0 Hz, 4H), 7.62–7.37 (m, 19H), 7.31–7.22 (m, 9H), 7.05 (dd, J= 2.0, 8.0 Hz, 1H), 696 (dd, J=2.0, 8.0 Hz, 1H), 6.79–6.75 (m, 2H), 6.56 (d, J= 2.0 Hz, 1H), 6.41–6.36 (m, 3H); MS (M+) Calculated for $C_{64}H_{40}$ 808, found 808; analysis calculated for $C_{64}H_{40}$: C, 95.02; H, 4.98. Found: C, 95.10; H, 4.90.

Example 16

Synthesis of Chemical Compound 117

To a solution of 2-bromonaphthalene (6.49 g, 31.3 mmol) in dry THF (50 ml) was added dropwise t-BuLi (18.4 ml of a 1.7 M solution in pentane) at −78° C. under nitrogen. After the mixture had been stirred for 30 min, 2-bromoanthraquinone (3.00 g, 10.4 mmol) was added at −78° C. The cooling bath was removed and the mixture was stirred for 2 hours at room temperature. The mixture was quenched with saturated aqueous ammonium chloride solution (50 ml) and extracted with ethyl ether (3×50 ml). The combined organic extracts were dried over MgSO$_4$ and concentrated under vacuum. The crude product was slurried in petroleum ether, filtered off with suction, and washed with petroleum ether. After drying, the 2-bromo-9,10-di-naphthalene-2-yl-9,10-dihydro-anthracene-9,10-diol (5.30 g, 93%) was obtained.

A mixture of the diol (5.43 g, 10 mmol) obtained above, potassium iodide (15 g), and sodium hypophosphite hydrate (15 g) in acetic acid (100 ml) was stirred while refluxing for 1 hour under nitrogen. After cooling the mixture to room temperature, the precipitate was filtered off with suction and washed with water and methanol. After drying, 2-bromo-9,10-(di-2-naphtyl)-anthracene (4.00 g, 79%) was obtained.

To a solution of 2-bromo-9,10-(di-2-naphtyl)-anthracene (0.60 g, 1.18 mmol), Chemical Compound 8 (0.62 g, 1.18 mmol), and sodium carbonate (0.38 g, 3.54 mmol) in a mixture of toluene (30 ml), ethanol (6 ml), and water (10 ml), tetrakis(triphenylphosphine)palladium (27 mg, 0.02 mmol) was added. The reaction mixture was stirred while refluxing for 24 hours and quenched with conc. HCl (1 ml). Then it was cooled to room temperature and extracted with dichlomethane (3×30 ml). The combined organic extracts were dried over MgSO$_4$ and concentrated under vacuum.

The residue was dissolved in chloroform, filtered through a short column of silica gel, and concentrated under vacuum. Recrystallization from chloroform and ethanol afforded Chemical Compound 117 (0.70 g, 65%) as pale yellow solid: mp 462.6° C.; $^1$H NMR ( 500 MHz, DMSO-d$_6$) δ 8.36 (d, J= 8.3 Hz, 1H), 8.18–7.97 (m, 8H), 7.88–7.74 (m, 4H), 7.64–7.51 (m, 6H), 7.48–7.40 (m, 4H), 7.37–7.02 (m, 15H), 6.82–6.77 (m, 2H), 6.30–6.15 (m, 4H); MS (M+) Calculated for $C_{72}H_{44}$ 908, found 908; analysis calculated for $C_{72}H_{44}$: C, 95.12; H, 4.88. Found: C, 95.36; H, 4.64.

Example 17

Synthesis of Chemical Compound 118

To a suspension of 2-bromo-9,10-bis(2-biphenyl) (0.56 g, 1.00 mmol), Chemical formula 8 (0.79 g, 1.50 mmol), and potassium phosphate (0.64 g, 3.00 mmol)) in DMF (10 ml) was added tetrakis(triphenylphosphine)palladium (35 mg, 0.03 mmol) under nitrogen. The mixture was degassed with nitrogen for 30 min. After the reaction mixture had been stirred at 90° C. for 18 hours, it was cooled to room temperature and ethanol (50 ml) was added. After addition, the reaction mixture was stirred at room temperature for 30 minutes. The precipitate was filtered off with suction, washed with water and ethanol, and dried under vacuum. Then it was dissolved in chloroform (500 ml), filtered through a short column of silica gel, and concentrated under vacuum. Purification by sublimation afforded Chemical Compound 118 (0.63 g, 66%) as white solid: mp 409.8° C.; $^1$H NMR (500 MHz, CDCl$_3$) δ 7.96 (d, J=7.4 Hz, 2H), 7.91 (dd, J=4.6, 7.4 Hz, 2H), 7.59–7.12 (m, 26H), 6.97 (ddd, J=2.3, 8.7, 14.2 Hz, 2H), 6.87–6.73 (m, 8H), 6.68–6.63 (m, 4H), 6.60 (d, J=1.9 Hz, 1H), 6.41 (d, J=8.7 Hz, 1H), 6.40–6.36 (m, 2H); MS (M+) Calculated for $C_{76}H_{48}$ 960, found 960; analysis calculated for $C_{76}H_{48}$: C, 94.79; H, 5.03. Found: C, 95.10; H, 4.89.

Example 18

Synthesis of Chemical Compound 119

To a solution of 1,3,5-tribromobenzene (10.0 g, 31.8 mmol), phenylboronic acid (9.68 g, 79.4 mmol), and sodium carbonate (25.3 g, 0.24 mol) in a mixture of toluene (150 ml), ethanol (30 ml), and water (75 ml), tetrakis(triphenylphosphine)palladium (1.84 g, 5 mol%) was added. The reaction mixture was stirred while refluxing for 24 hours and quenched with conc. HCl (20 ml). Then it was cooled to room temperature and extracted with ethyl ether (3×50 ml). The combined organic extracts were dried over MgSO$_4$ and concentrated under vacuum. Purification by column chromatography (n-hexane) afforded 3,5-(diphenyl)bromobenzene (9.82 g, 51%)

To a solution of 3,5-(diphenyl)bromobenzene (5.00 g, 16.2 mmol) in dry THF (50 ml) was added dropwise t-BuLi (9.53 ml of a 1.7 M solution in pentane) at −78° C. under nitrogen. After the mixture had been stirred for 30 min, 2-bromoanthraquinone (1.55 g, 5.39 mmol) was added at −78° C. The cooling bath was removed and the mixture was stirred for 2 hours at room temperature. The mixture was quenched with saturated aqueous ammonium chloride solution (50 ml) and extracted with ethyl ether (3×50 ml). The combined organic extracts were dried over MgSO$_4$ and concentrated under vacuum. The crude product was slurried in petroleum ether, filtered off with suction, and washed with petroleum ether. After drying, 2-bromo-9,10-[1,1',3',1"]terphenyl-5'-yl-9,10-dihydro-anthracene-9,10-diol (3.00 g, 74%) was obtained.

A mixture of the diol obtained above (2.24 g, 3.0 mmol), potassium iodide (2.25 g, 13.6 mmol), and sodium hypophosphite hydrate (2.25 g, 25.6 mmol) in acetic acid (30 ml) was stirred while refluxing for 1 hour under nitrogen. After cooling to room temperature, the precipitate was filtered off with suction, and washed with water and methanol. After drying, 2-bromo-9,10-[1,1',3',1"]terphenyl-5'-yl -anthracene (1.75 g, 82%) was obtained.

To a solution of 2-bromo-9,10-[1,1',3',1"]terphenyl-5'-yl-anthracene (0.5 g, 0.70 mmol), Chemical Compound 8 (0.55 g, 1.05 mmol), and sodium carbonate (0.22 g, 2.1 mmol) dissolved in a mixture of toluene (30 ml), ethanol (6 ml), and water (10 ml), tetrakis(triphenylphosphine)palladium (16 mg, 2 mol%) was added. The reaction mixture was stirred while refluxing for 24 hours and quenched with conc. HCl (1 ml). Then, it was cooled to room temperature and extracted with dichlomethane (3×30 ml). The combined organic extracts were dried over $MgSO_4$ and concentrated under vacuum. The residue was dissolved in chloroform, filtered through a short column of silica gel, and concentrated under vacuum. Recrystallization from chloroform and ethanol afforded Chemical Compound 119 (0.45 g, 58%) as pale yellow solid: mp 512.8° C.; $^1$H NMR ( 500 MHz, DMSO-$d_6$) δ 8.38 (s, 1H), 8.15–7.82 (m, 11H), 7.75–7.38 (m, 20H), 7.32–7.05 (m, 16H), 6.82–6.75 (m, 3H), 6.38–6.10 (m, 5H); MS (M+) Calculated for $C_{88}H_{56}$ 1112, found 1112; analysis calculated for $C_{88}H_{56}$: C, 94.93; H, 5.07. Found: C, 95.18; H, 4.82.

Example 19

Synthesis of Chemical Compound 136

To a suspension of 2-bromo-9,10-di[2-(2'-phenyl)biphenyl]-anthracene (0.40 g, 0.56 mmol), Chemical Compound 8 (0.63 g, 1.12 mmol), and potassium phosphate (0.36 g, 1.68 mmol)) in DMF (40 ml) was added tetrakis(triphenylphosphine)palladium (65 mg, 0.06 mmol) under nitrogen. After the reaction mixture had been stirred at 80° C. for 24 hours, it was cooled to room temperature. The precipitate was filtered off with suction, washed with water, ethanol, and acetone, and dried under vacuum. Then it was dissolved in chloroform (50 ml) and filtered through a short column of silica gel. After removal of solvent, the crude product was purified by crystallizing from ethanol to Chemical Compound 136 (0.11 g, 18%): mp 385.4° C.; $^1$H NMR is not listed because of insolubility of Chemical Compound 136 in common solvents. MS (M+) calculated for $C_{88}H_{56}$ 1112, found 1112.

Example 20

Synthesis of Chemical Compound 301

To a suspension of Chemical Compound 1 (1.50 g, 2.68 mmol), N-phenyl-1-naphtylamine (0.59 g, 2.68 mmol), and sodium t-butoxide (0.31 g, 3.22 mmol) in o-xylene (20 ml), $Pd(OAc)_2$ (0.2 mg, 0.007 mmol) and $P(t-Bu)_3$ (0.50 mg, 0.003 mmol) were added. After the reaction mixture had been stirred at 130° C. for 3 hours, it was cooled to room temperature, quenched with water (40 ml), and extracted with dichloromethane (3×40 ml). The combined organic extracts were dried over $MgSO_4$ and concentrated under vacuum. Purification by recrystallization from chloroform and ethanol afforded Chemical Compound 301 (1.50 g, 80%) as white solid: mp 370.4° C.; $^1$H NMR (500 MHz, DMSO-$d_6$) δ 8.03 (d, J= 7.3 Hz, 2H), 7.88 (dd, J=7.8, 8.5 Hz, 3H), 7.76 (d, J=8.3 Hz, 1H), 7.44–7.32 (m, 11H), 7.26 (m, 4H), 7.19 (dt, J=1.0, 8.3 Hz, 1H), 7.03 (dd, J=1.0, 7.3 Hz, 1H), 6.86–6.80 (m, 4H), 6.71 (t, J=7.3 Hz, 1H), 6.38 (d, J=7.8 Hz, 2H), 6.24–6.21 (m, 2H), 6.16 (dd, J=2.8, 8.7 Hz, 1H), 6.13 (d, J=2.3 Hz, 1H), 6.06 (d, J=8.7 Hz, 1H); MS (M+) calculated for $C_{54}H_{35}N$ 697, found 696; analysis calculated for $C_{54}H_{35}N$: C, 92.94; H, 5.06; N, 2.01. Found: C, 93.05; H, 4.91; N, 2.04.

Example 21

Synthesis of Chemical Compound 303

To a solution of Chemical Compound 1 (2.00 g, 3.56 mmol), 4-(dimethylamino)-phenylboronic acid (1.24 g, 4.27 mmol), and sodium carbonate (1.13 g, 10.7 mmol) in a mixture of toluene (40 ml), ethanol (6 ml), and water (20 ml), tetrakis(triphenylphosphine)palladium (130 mg, 3 mol%) was added. The reaction mixture was stirred while refluxing for 12 hours. Then, it was cooled to room temperature and water (50 ml) was added. The organic layer was separated and the aqueous layer was extracted with ethyl acetate (3×50 ml). The combined organic extracts were dried over $MgSO_4$ and concentrated under vacuum. Purification by column chromatography (1:2 THF-hexane) and recrystallization from THF and ethanol afforded Chemical Compound 303. (0.70 g, 27%) as white solid: mp 326.0° C.; $^1$H NMR (300 MHz, $CDCl_3$) δ 7.91 (dd, J= 4.9, 7.5 Hz, 4H), 7.44–7.30 (m, 4H), 7.30–7.15 (m, 13H), 7.01–6.85 (m, 11H), 6.79–6.72 (m, 2H), 6.56 (d, J=1.9 Hz, 1H), 6.44–6.39 (m, 3H); MS (M+) calculated for $C_{56}H_{37}N$ 723, found 723; analysis calculated for $C_{56}H_{37}N$: C, 92.91; H, 5.15; N, 1.93. Found: C, 92.70; H, 5.07; N, 2.12.

Example 22

Synthesis of Chemical Compound 400

To a suspension of Chemical Compound 1 (3.00 g, 5.34 mmol), N,N-diphenyl-4-(vinylphenyl)amine (1.74 g, 6.41 mmol), and triethylamine (6 ml, 43.0 mmol)) in DMF (20 ml), $Pd(OAc)_2$ (40 mg, 0.18 mmol) and tri-o-tolylphosphine (270 mg, 0.90 mmol) were added. After the reaction mixture had been stirred while refluxing for 15 hours, it was cooled to room temperature, quenched with water (40 ml), and extracted with chloroform (3×40 ml). The combined organic extracts were dried over $MgSO_4$ and concentrated under vacuum. Purification by column chromatography (1:2 dichloromethane-hexane) and recrystallization from chloroform and ethanol afforded Chemical Compound 400 (3.1 g, 77%) as ivory solid: mp 358.7° C.; $^1$H NMR (300 MHz, $CDCl_3$) δ 7.92 (dd, J= 4.0, 7.6 Hz, 4H), 7.44–7.40 (m, 3H), 7.32–7.12 (m, 15H), 7.04–6.89 (m, 9H), 6.76 (dd, J= 3.4, 6.1 Hz, 2H), 6.56 (dd, J=12.0, 21.0 Hz, 2H), 6.40–6.36 (m, 4H); MS (M+) calculated for $C_{58}H_{39}N$ 749, found 749; analysis calculated for $C_{58}H_{39}N$: C, 92.89; H, 5.24; N, 1.87. Found: C, 93.12; H, 5.26; N, 1.65.

Example 23

Synthesis of Chemical Compound 307

To a suspension of Chemical Compound 1 (0.34 g, 0.60 mmol), diphenylbenzidine (0.40 g, 1.20 mmol), and sodium t-butoxide (0.10 g, 1.10 mmol) in o-xylene (10 ml), Pd(OAc)$_2$ (8.0 mg, 0.04 mmol) and P(t-Bu)$_3$ (29 mg, 0.14 mmol) were added. After the reaction mixture had been stirred while refluxing for 2 hours, iodobenzene (1.0 ml, 8.94 mmol) was added. After the resulting reaction mixture had been stirred while refluxing for 21 hours, it was cooled to room temperature and quenched with water. The organic layer was separated and the aqueous layer was extracted with toluene. The combined organic extracts were dried over MgSO$_4$, filtered through a short column of silica gel, and concentrated under vacuum. Purification by column chromatography (1:4 THF-hexane) and sublimation afforded Chemical Compound 307 (0.20 g, 37%) as ivory solid: mp 315.9° C.; $^1$H NMR (300 MHz, DMSO-d$_6$) δ 8.06 (d, J=7.4 Hz, 2H), 7.91 (d, J=7.4 Hz, 2H), 7.48–7.40 (m, 20H), 7.08–6.98 (m, 9H), 6.91 (d, J=7.5 Hz, 2H), 6.83–6.79 (m, 2H), 6.66(d, J=7.6 Hz, 2H), 6.61 (d, J=8.6 Hz, 2H), 6.40–6.36 (m, 1H), 6.26–6.20 (m, 2H), 6.12 (d, J=9.3Hz, 1H), 6.05–6.01 (m, 1H); MS (M+) calculated for C$_{68}$H$_{46}$N$_2$ 890, found 890; analysis calculated for C$_{68}$H$_{46}$N$_2$: C, 91.65; H, 5.20; N, 3.14. Found: C, 91.95; H, 5.20; N, 2.85.

Example 24

Synthesis of Chemical Compound 305

To a solution of 2-bromo-4,4'-bis(diphenylamino)biphenyl (0.57 g, 1.00 mmol) and Chemical Compound 8 (0.79 g, 1.50 mmol in a mixture of toluene (30 ml) and 2 N potassium carbonate solution (10 ml), tetrakis(triphenylphosphine)palladium (35 mg, 0.03 mmol) was added. The reaction mixture was stirred at 80° C. for 24 hours. Then it was cooled to room temperature and water (50 ml) was added. The organic layer was separated, and the aqueous layer was extracted with toluene. The combined organic extracts were dried over MgSO$_4$ and concentrated under vacuum. Purification by column chromatography (1:19 ethyl acetate-hexane) afforded Chemical Compound 305 (0.36 g, 37%) as ivory solid: mp 353° C.; $^1$H NMR (300 MHz, DMSO-d$_6$) δ 8.04–7.99 (m, 4H), 7.42–6.70 (m, 38H), 6.55–5.98 (m, 8H); MS (M+) calculated for C$_{74}$H$_{50}$N$_2$ 966, found 966.

Example 25

Synthesis of Chemical Compound 9

To a suspension of Chemical Compound 8 (0.52 g, 1.00 mmol), 9-bromoanthracene (0.25 g, 1.00 mmol), and potassium phosphate (0.42 g, 2.00 mmol) in DMF (10 ml) tetrakis(triphenylphosphine)palladium (35 mg, 0.03 mmol) was added under nitrogen. After the reaction mixture had been stirred at 80° C. for 12 hours, it was cooled to room temperature and ethanol (15 ml) was added. After addition, the reaction mixture had been stirred at room temperature for 10 minutes. The precipitate was filtered off with suction, washed with water, ethanol, and acetone. Purification by sublimation afforded Chemical Compound 9 (0.40 g, 60%): MS (M+) calculated for C$_{52}$H$_{32}$ 656, found 656.

Example 26

Synthesis of Chemical Compound 5

To a solution of Chemical Compound 9 (0.35 g, 0.53 mmol) in dry CCl$_4$ (80 ml), bromine (27 mL, 0.53 mmol) was added dropwise at room temperature. After the reaction mixture had been stirred for 5 hours at room temperature, it was quenched with saturated aqueous sodium bicarbonate solution. The organic layer was dried over MgSO$_4$ and concentrated in vacuum. Purification by column chromatography (1:4 THF-hexane) afforded Chemical Compound 5 (0.28 g, 72%): MS (M+) calcd for C$_{52}$H$_{31}$Br 734, found 734.

Example 27

Synthesis of Chemical Compound 401

To a suspension of Chemical Compound 5 (1.60 g, 2.20 mmol), 4-diphenylaminophenylboronic acid (0.63 g, 2.20 mmol), and potassium phosphate (0.93 g, 4.40 mmol) in DMF (80 ml) was added tetrakis(triphenylphosphine)palladium (81 mg, 0.07 mmol) under nitrogen. After the reaction mixture had been stirred at 80° C. for 12 hours, it was cooled to room temperature and ethanol (80 ml) was added. After addition, the reaction mixture was stirred at room temperature for 10 minutes. The precipitate was filtered off with suction, washed with water, ethanol, and acetone. Purification by sublimation afforded Chemical Compound 401 (0.80 g, 41%): mp 489.5° C.; $^1$H NMR (300 MHz, CDCl$_3$) δ 8.00 (d, J=7.5 Hz, 2H), 7.78–7.73 (m, 2H), 7.67 (d, J=8.6 Hz, 2H), 7.54–7.00 (m, 31H), 6.92 (d, J= 10.8 Hz, 1H), 6.83–6.80 (m, 3H), 6.62 (d, J=7.5 Hz, 1H), 6.48–6.40 (m, 3H), MS (M+) calculated for C$_{70}$H$_{45}$N 899, found 899; analysis calculated for C$_{70}$H$_{45}$N: C, 93.40; H, 5.04; N, 1.56. Found: C, 93.30; H, 4.95; N, 1.95.

Example 28

Synthesis of Chemical Compound 10

To a suspension of Chemical Compound 1 (2.00 g, 3.56 mmol), carbazole (0.89 g, 5.34 mmol), and potassium carbonate (0.59 g, 4.27 mmol) in xylene (60 ml), palladium acetate (0.02 g, 0.11 mmol) and tri-tert-butylphosphine (80 mg, 0.43 mmol) were added. After the reaction mixture had been stirred while refluxing for 24 hours, it was cooled to room temperature, quenched with water, and extracted with ethyl acetate. The organic extract was dried over MgSO$_4$ and concentrated under vacuum. Purification by column chromatography (1:2 chloroform-hexane) afforded Chemical Compound 10 (1.69 g, 74%): MS (M+) calculated for C$_{50}$H$_{31}$N 645, found 645.

Example 29

Synthesis of Chemical Compound 6

To a solution of Chemical Compound 10 (0.50 g, 0.77 mmol) in a mixture of chloroform (20 ml) and acetic acid (20 ml), bromine (0.08 ml, 1.55 mmol) in acetic acid (0.1 ml) was added dropwise at 0° C. After the reaction mixture had been stirred for 2 hours at room temperature, it was quenched with water and extracted with chloroform. The organic layer was dried over MgSO$_4$ and concentrated in vacuum. Purification by recrystallization from ethanol afforded Chemical Compound 6 (0.53 g, 85%): MS (M+) calculated for C$_{50}$H$_{29}$Br$_2$N 801, found 801.

Example 30

Synthesis of Chemical Compound 403

To a suspension of Chemical Compound 6 (0.70 g, 0.87 mmol), N-phenyl-1-naphtylamine (0.57 g, 2.61 mmol), and sodium tert-butoxide (0.5 g, 5.22 mmol)) in xylene (30 ml) were added palladium acetate (0.01 g, 0.05 mmol) and tri-tert-butylphosphine (50 mg, 0.05 mmol). After the reaction mixture had been stirred while refluxing for 24 hours, it was cooled to room temperature, quenched with water, and extracted with ethyl acetate. The organic extract was dried over $MgSO_4$ and concentrated under vacuum. Purification by column chromatography (1:2 chloroform-hexane) afforded Chemical Compound 403 (0.39 g, 45%): mp 413.0° C.; $^1$H NMR (300 MHz, $CDCl_3$) δ 7.93 (dd, J= 4.3, 7.5 Hz, 3H), 7.82 (t, J= 8.1 Hz, 3H), 7.67 (d, J=8.0 Hz, 2H), 7.56 (s, 2H), 7.43–7.13 (m, 22H), 7.07 (t, J=7.9 Hz, 4H), 6.94 (dd, J=2.2, 8.8 Hz, 3H), 6.88–6.65 (m, 10H), 6.58–6.40 (m, 3H); MS (M+) calculated for $C_{82}H_{53}N_3$ 1079, found 1079.

Example 31

Synthesis of Chemical Compound 11

To a suspension of Chemical Compound 1 (1.12 g, 2.00 mmol), diphenylamine (0.51 g, 3.00 mmol), and sodium tert-butoxide (0.23 g, 2.40 mmol)) in xylene (15 ml) were added palladium acetate (0.01 g, 0.04 mmol) and tri-tert-butylphosphine (33 mg, 0.16 mmol). After the reaction mixture had been stirred while refluxing for 15 hours, it was cooled to room temperature, quenched with water, and extracted with chloroform. The organic extract was dried over $MgSO_4$ and concentrated under vacuum. Purification by recrystallization from chloroform and ethanol afforded Chemical Compound 11 (1.22 g, 94%): MS (M+) calculated for $C_{50}H_{33}N$ 647, found 647.

Example 32

Synthesis of Chemical Compound 7

To a solution of Chemical Compound 11 (1.09 g, 1.68 mmol) and benzoyl peroxide (10 mg) in dry $CCl_4$ (70 ml) was added N-bromosuccinimide (0.64 g, 3.60 mmol) over a period of 10 minutes at room temperature. After the reaction mixture had been stirred for 36 hours at room temperature, it was quenched with saturated aqueous sodium bicarbonate solution and extracted with chloroform. The organic layer was dried over $MgSO_4$ and concentrated in vacuum. Purification by recrystallization from chloroform and ethanol afforded Chemical Compound 7 (0.99 g, 73%): MS (M+) calculated for $C_{50}H_{31}Br_2N$ 803, found 803.

Example 33

Synthesis of Chemical Compound 308

Chemical Compound 7 (0.97 g, 1.20 mmol) was prepared by reacting Chemical Compound 11 and N-bromosuccinimide in carbon tetrachloride, diphenylamine (0.61 g, 3.60 mmol), and sodium tert-butoxide (0.28 g, 2.40 mmol). To a suspension of Chemical Compound 7 in xylene (20 ml), palladium acetate (12 mg, 0.05 mmol) and tri-tert-butylphosphine (39 mg, 0.20 mmol) were added. After the reaction mixture was stirred while refluxing for 24 hours, it was cooled to room temperature, quenched with water, and extracted with ethyl acetate (3×50 ml). The combined organic extracts were dried over $MgSO_4$ and concentrated under vacuum. Purification by recrystallization from ethanol and ethyl acetate afforded Chemical Compound 308 (0.84 g, 71%): mp 329.2° C.; $^1$H NMR (300 MHz, $CDCl_3$) δ 7.89 (d, J=7.3 Hz, 8H), 7.77 (d, J=6.5 Hz, 8H), 7.41–7.20 (m, 19H), 6.78–6.60 (m, 8H), 6.40–6.32 (m, 8H); MS (M+) calculated for $C_{74}H_{51}N_3$ 981, found 981.

EXAMPLES OF ORGANIC EL DEVICES

Example 34

Organic EL Device Using Chemical Compound

Figure 2:
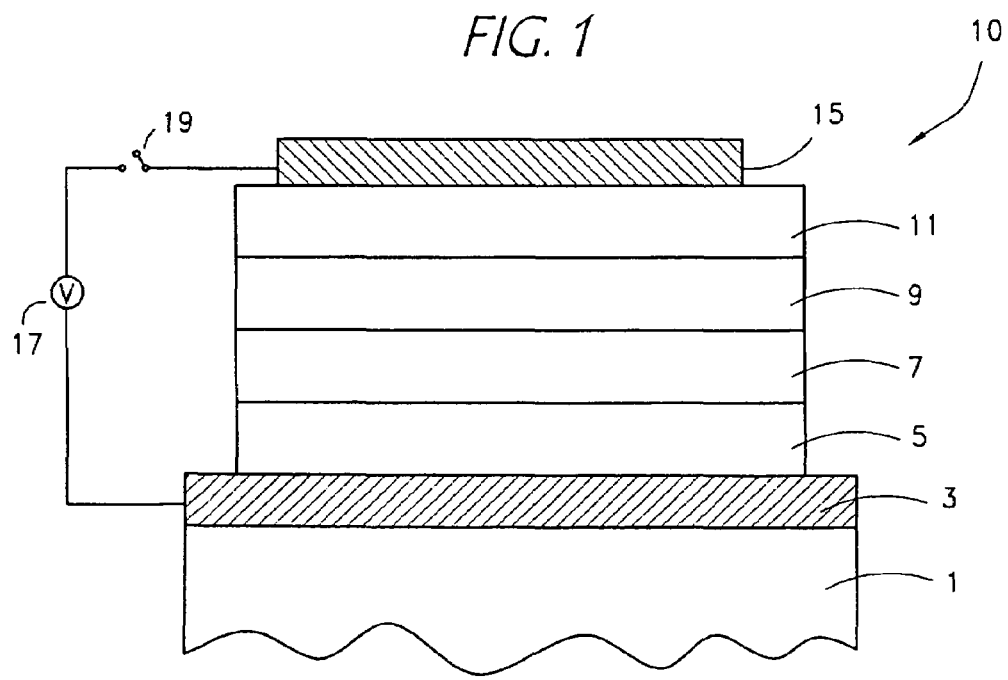

An organic light-emitting device having the construction as illustrated in FIG. 2 was fabricated with Chemical Compound 12 in the light-emitting layer 9. The preparation of Chemical Compound 12 is disclosed in the article by Clarkson and Gomberg titled *Spirans With Four Aromatic Radicals on the Spiro Carbon Atoms* (J. Am. Chem. Soc. 52, 2881 (1930),) which is hereby incorporated herein by reference.

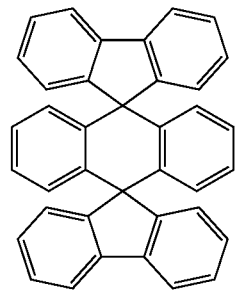

Chemical Compound 12

A glass substrate coated with a thin film of ITO (indium tin oxide) having thickness of about 1500 Å was ultrasonically cleaned in a solution of a cleaning agent, dried, and transferred into a plasma cleaning device. The substrate was cleaned with oxygen plasma for 5 minutes, and transferred to a thermal vapor deposition chamber. A hole-injecting layer having thickness of about 500 Å was formed by thermal vacuum deposition of the hexanitrile hexaazatriphenylene, a stable hole-injecting material, over the ITO (anode).

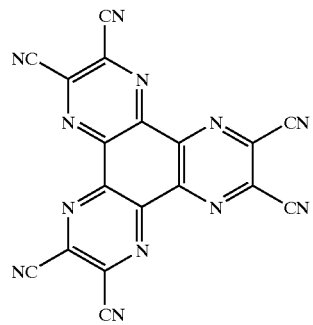

Hexanitrile hexaazatriphenylene

A hole-transporting layer having thickness of about 600 Å was formed by thermal vacuum deposition of NPB, a hole-transporting material, over the hole-injecting layer. An emitting layer having thickness of about 150 Å was formed by thermally vacuum depositing Chemical Compound 12 over the hole-transporting layer. On top of the light-emitting layer, 8-hydroxyquinoline Aluminum salt (Alq3), an n-type organic semiconductor, was deposited with thickness of about 300 Å to form an electron-transporting layer. Then, a cathode electrode was formed by depositing 5 Å of LiF and about 2500 Å of aluminum on the electron-transporting layer. In the process, the deposition speed was controlled to maintain 1 Å/sec for organic material, 0.2 Å/sec for lithium fluoride, and 3–7 Å/sec for aluminum.

When forward bias was applied across the light-emitting device, blue light emission centered at the wavelength of 476 nm was observed. The efficiency of the light-emitting device was 0.6 cd/A at a current density of 10 mA/cm$^2$.

Example 35

Organic EL Device Using Chemical Compound 109

An organic light-emitting device was produced in the same manner as in Example 34 except that Chemical Compound 109 was used as the light-emitting material with thickness of about 400 Å instead of Chemical Compound 12. When forward bias was applied across the light-emitting device, blue light emission centered at the wavelength of 452 nm was observed. The efficiency of the light-emitting device was 2.0 cd/A at a current density of 10 mA/cm$^2$.

Example 36

Organic EL Device Using Chemical Compound 102

An organic light-emitting device was produced in the same manner as in Example 34 except that Chemical Compound 102 was used as the light-emitting material with thickness of about 400 Å instead of Chemical Compound 12. When forward bias was applied across the light-emitting device, blue light emission centered at the wavelength of 464 nm was observed. The efficiency of the light-emitting device was 2.5 cd/A at a current density of 10 mA/cm$^2$.

Example 37

Organic EL Device Using Chemical Compound 118

An organic light-emitting device was produced in the same manner as in Example 34 except that Chemical Compound 118 was used as the light-emitting material with thickness of 300 Å instead of Chemical Compound 12. When forward bias was applied across the light-emitting device, blue light emission centered at the wavelength of 464 nm was observed. The efficiency of the light-emitting device was 2.1 cd/A at a current density of 10 mA/cm$^2$.

Example 38

Organic EL Device Using Chemical Compound 100

An organic light-emitting device was produced in the same manner as in Example 34 except that Chemical Compound 100 was used as the light-emitting material with thickness of about 300 Å instead of Chemical Compound 12. When forward bias was applied across the light-emitting device, blue light emission centered at the wavelength of 444 nm was observed. The efficiency of the light-emitting device was 0.64 cd/A at a current density of 10 mA/cm$^2$.

Example 39

Organic EL Device Using Chemical Compound 117

An organic light-emitting device was produced in the same manner as in Example 34 except that Chemical Compound 117 was used as the light-emitting material with thickness of about 150 Å instead of Chemical Compound 12. When forward bias was applied across the light-emitting device, blue light emission centered at the wavelength of 484 nm was observed. The efficiency of the light-emitting device was 2.4 cd/A at a current density of 10 mA/cm$^2$.

Example 40

Organic EL Device Using Chemical Compound 113

An organic light-emitting device was produced in the same manner as in Example 34 except that Chemical Compound 113 was used as the light-emitting material with thickness of about 150 Å instead of Chemical Compound 12. When forward bias was applied across the light-emitting device, blue light emission centered at the wavelength of 452 nm from the compound having a structure of Chemical Compound 113 was observed. The efficiency of the light-emitting device was 1.6 cd/A at a current density of 10 mA/cm$^2$.

Example 41

Organic EL Device Using Chemical Compound 111

An organic light-emitting device was produced in the same manner as in Example 34 except that Chemical Compound 111 was used as the light-emitting material with thickness of 150 Å instead of Chemical Compound 12. When forward bias was applied across the light-emitting device, blue light emission centered at the wavelength of 452 nm was observed. The efficiency of the light-emitting device was 2.1 cd/A at a current density of 10 mA/cm$^2$.

Example 42

Organic EL Device Using Chemical Compound 110

Figure 7:
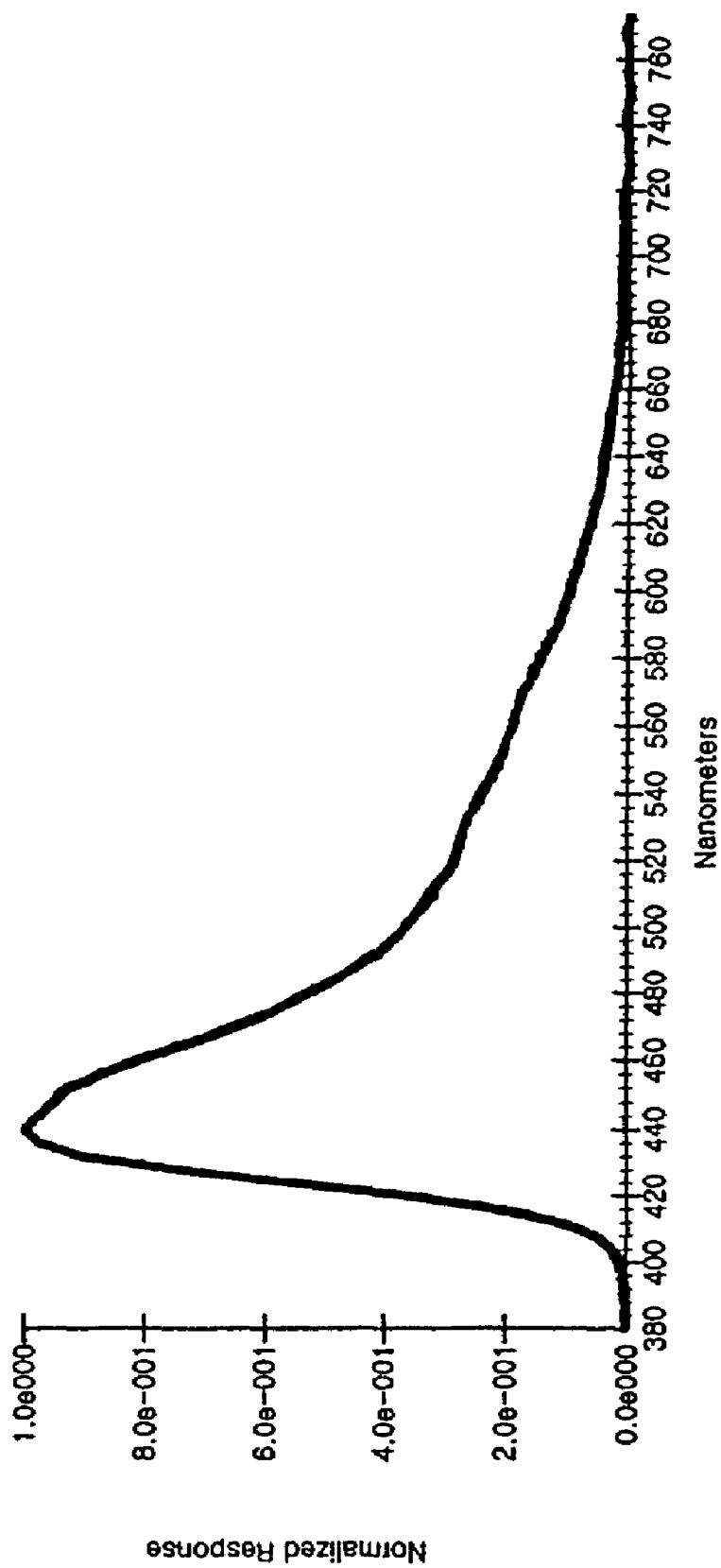
FIG. 7 is a spectrum of light emission from the organic EL device manufactured in Example 42.

An organic light-emitting device was produced in the same manner as in Example 34 except that Chemical Compound 110 was used as the light-emitting material with thickness of 150 Å instead of Chemical Compound 12. When forward bias was applied across the light-emitting device, blue light emission centered at the wavelength of 440 nm was observed. The efficiency of the light-emitting device was 1.9 cd/A at a current density of 10 mA/cm$^2$. FIG. 7 shows the spectrum of light emission of this device.

Example 43

Organic EL Device Using Chemical Compound 134

An organic light-emitting device was produced in the same manner as in Example 34 except that Chemical Compound 134 was used as the light-emitting material with thickness of 300 Å instead of Chemical Compound 12. When forward bias was applied across the light-emitting device, green light emission centered at the wavelength of 508 nm was observed. The efficiency of the light-emitting device was 1.3 cd/A at a current density of 10 mA/cm$^2$.

Example 44

Organic EL Device Using Chemical Compound 200

An organic light-emitting device having the construction as illustrated in FIG. 2 was manufactured, in which Chemical Compound 200 was used as an electron-transporting material.

A glass substrate coated with a thin film of ITO (indium tin oxide) having thickness of about 1500 Å was ultrasonically cleaned in a solution of a cleaning agent, dried, and transferred into a plasma cleaning device. The substrate was cleaned with oxygen plasma for 5 minutes, and transferred to a thermal vapor deposition chamber. A hole-injecting layer having thickness of about 500 Å was formed by thermal vacuum deposition of hexanitrile hexaazatriphenylene over the ITO coating (anode). A hole-transporting layer having thickness of about 600 Å was formed by thermal vacuum deposition of NPB over the hole-injecting layer. An emitting layer having thickness of about 150 Å was formed by thermal vacuum deposition of Chemical Compound 117. On top of the light-emitting layer, Chemical Compound 200 was deposited under vacuum with thickness of about 300 Å to form an electron-transporting layer. Then, an cathode electrode was formed by depositing 5 Å of LiF and about 2500 Å of aluminum on the electron-transporting layer. In the process, the deposing speed was controlled to maintain 1 Å/sec for organic material, 0.2 Å/sec for lithium fluoride, and 3–7 Å/sec for aluminum.

When forward bias was applied across the light-emitting device, blue light emission centered at the wavelength of 464 nm was observed. The efficiency of the light-emitting device was 3.8 cd/A at a current density of 10 mA/cm$^2$.

Example 45

Organic EL Device Using Chemical Compound 110

An organic light-emitting device having the construction as illustrated in FIG. 2 was manufactured, using Chemical Compound 110 as a host light-emitting molecule and tetra t-butyl perylene as a dopant molecule.

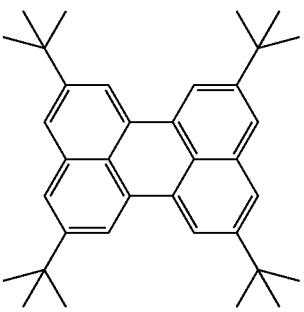

Tetra t-butyl perylene

A glass substrate coated with a thin film of ITO (indium tin oxide) having thickness of about 1500 Å was ultrasonically cleaned in a solution of a cleaning agent, dried, and transferred into a plasma cleaning device. The substrate was cleaned with oxygen plasma for 5 minutes, and transferred to a thermal vapor deposition chamber. A hole-injecting layer having thickness of about 500 Å was formed by thermal vacuum deposition of hexanitrile hexaazatriphenylene over the ITO (anode). A hole-transporting layer having thickness of about 600 Å was formed by thermal vacuum deposition of NPB over the hole-injecting layer. An emitting layer having thickness of about 150 Å was formed by co-deposition of Chemical Compound 110 and 1 wt% of tetra t-butyl perylene. On top of the light-emitting layer, 8-hydroxyquinoline Aluminum salt (Alq3) was deposited with a thickness of about 300 Å to form an electron-transporting layer. Then, a cathode electrode was formed by depositing 5 Å of LiF and about 2500 Å of aluminum on the electron-transporting layer. In the process, the deposing speed was controlled to maintain 3 Å/sec for the host material and 0.2 Å/sec for lithium fluoride, and 3–7 Å/sec for aluminum.

Figure 8:
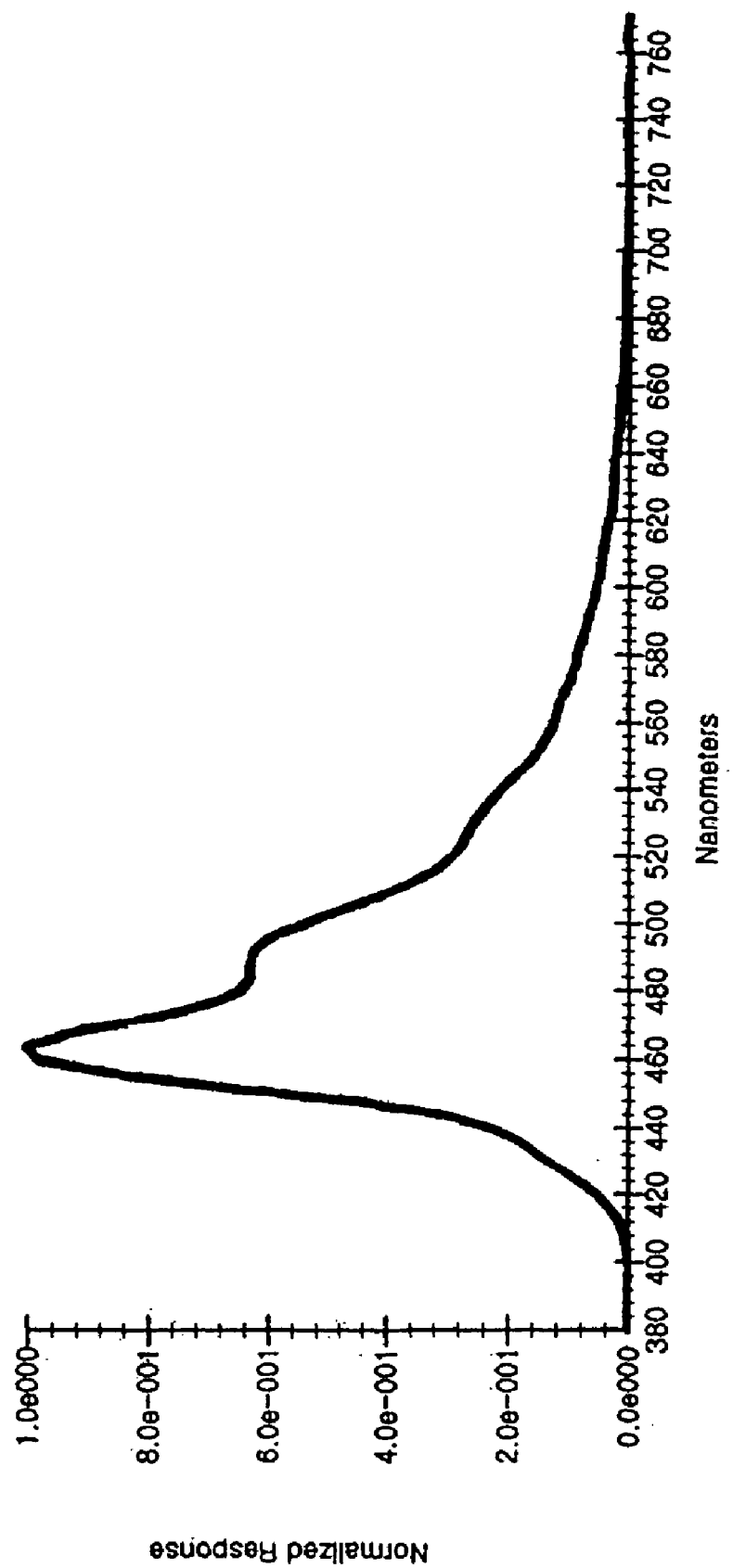
FIG. 8 is a spectrum of light emission from the organic EL device manufactured in Example 45.

When forward bias was applied across the light-emitting device, blue light emission centered at the wavelength of 464 nm was observed. The efficiency of the light-emitting device was 3.0 cd/A at a current density of 10 mA/cm$^2$. FIG. 8 shows the light-emission spectrum of this device. The center wavelength (464 nm) of this spectrum is longer than that in the spectrum of FIG. 7 (440 nm) where Chemical compound 110 was used as the only light-emitting material. This explains that most of the light emission was made in the dopant molecules rather than in the host molecule Chemical compound 110.

Example 46

Organic EL Device Using Chemical Compound 110

An organic light-emitting device having the construction as illustrated in FIG. 2 was manufactured, using Chemical Compound 110 as a host light-emitting molecule and DSA amine as a dopant molecule.

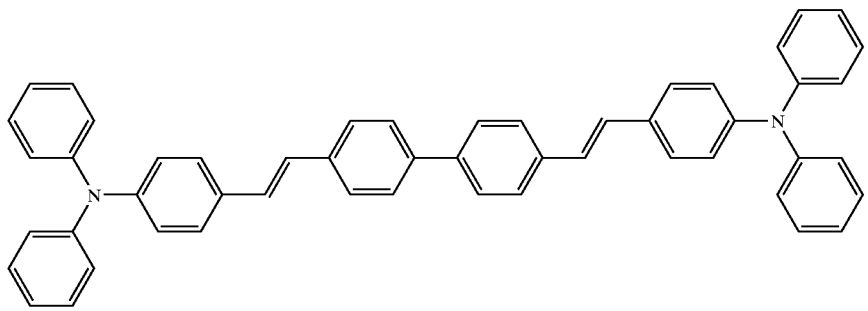

DSA Amine

The organic light-emitting device was obtained in the same manner as in Example 45 except that the thickness of the emitting layer was about 300 Å and DSA amine was used codeposited with Chemical Compound 110 as a dopant material instead of tetra t-butyl perylene. When forward bias was applied across the light-emitting device, blue light emission centered at the wavelength of 460 nm was observed. The efficiency of the light-emitting device was 4.6 cd/A at a current density of 10 mA/cm$^2$.

Example 47

Organic EL Device Using Chemical Compound 301

Figure 3:
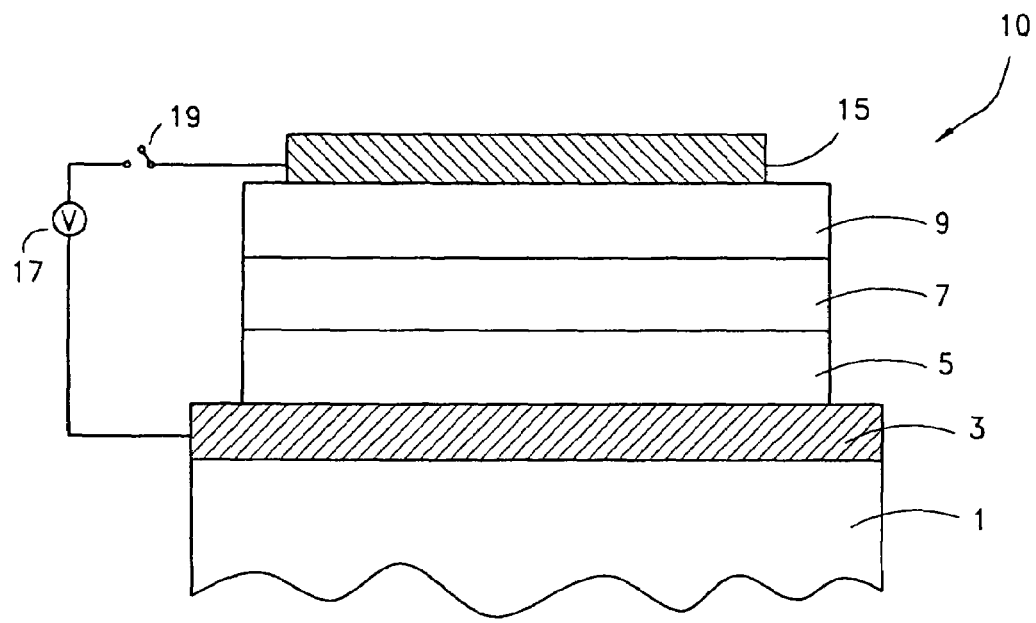
Figure 4:
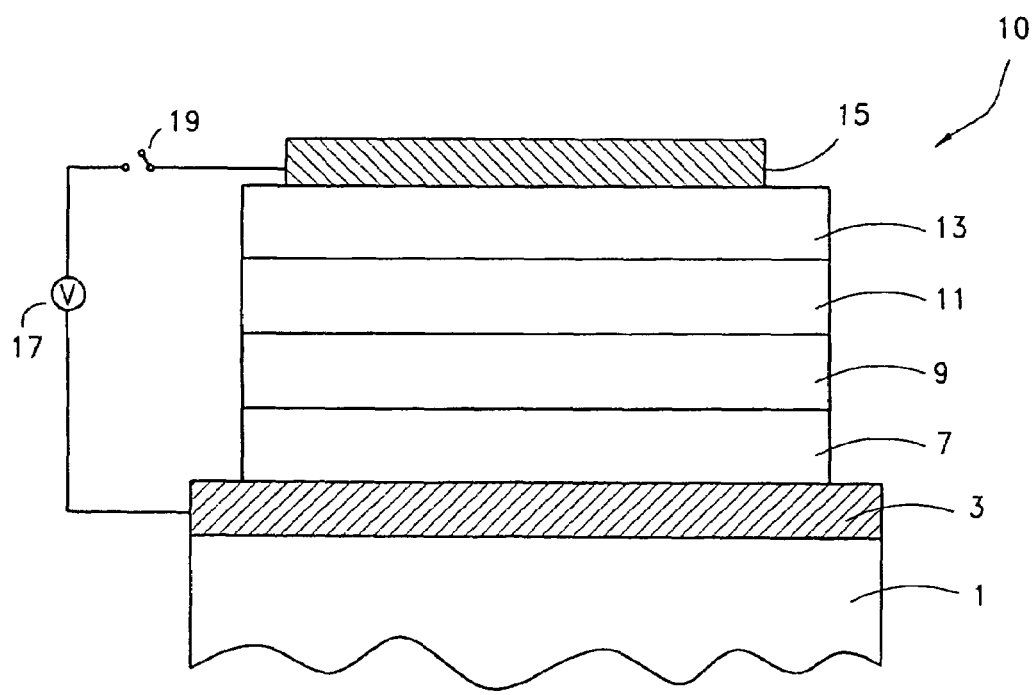
Figure 5:
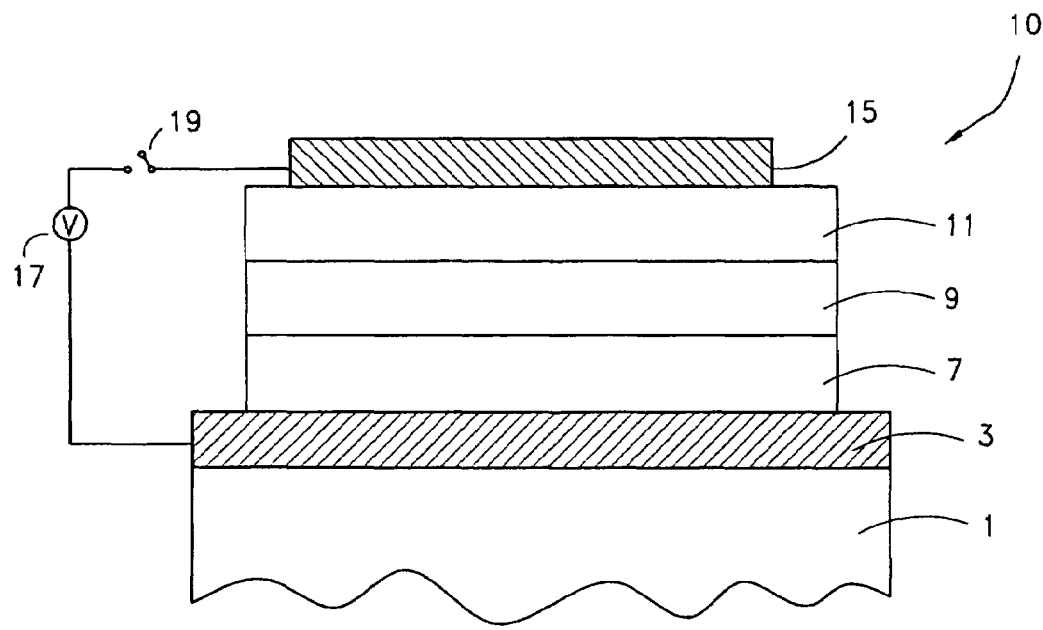
Figure 6:
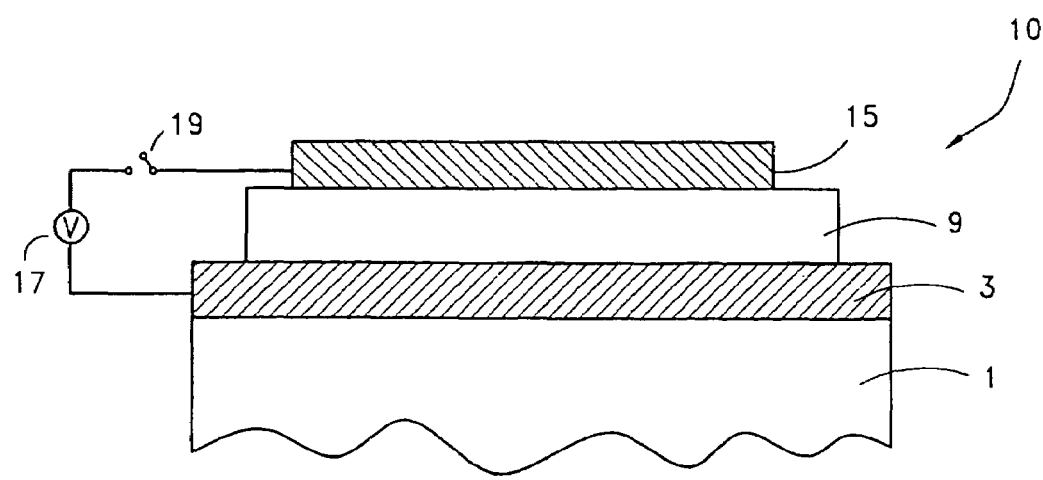

An organic light-emitting device having the construction shown in FIG. 3 was manufactured, using Chemical Compound 301 as a hole-transporting material.

A glass substrate coated with a thin film of ITO (indium tin oxide) having thickness of about 1500 Å was ultrasonically cleaned in a solution of a cleaning agent, dried, and transferred into a plasma cleaning device. The substrate was cleaned with oxygen plasma for 5 minutes, and transferred to a thermal vapor deposition chamber. A hole-injecting layer having thickness of about 500 Å was formed by thermal vacuum deposition of hexanitrile hexaazatriphenylene over the ITO coating (anode). A hole-transporting layer having thickness of about 400 Å was formed by thermal vacuum deposition of Chemical Compound 301 over the hole-injecting layer. On top of the hole-transporting layer, about 600 Å of 8-hydroxyquinoline Aluminum salt (Alq3) was deposited to form an emitting layer having electron-transporting properties as well. Then, an cathode electrode was formed by depositing 5 Å of LiF and about 2500 Å of aluminum on the electron-transporting layer. In the process, the deposing speed was controlled to maintain 1 Å/sec for organic material, 0.2 Å/sec for lithium fluoride, and 3–7 Å/sec for aluminum.

When forward bias was applied across the light-emitting device, green light emission from the Alq3 centered at the wavelength of 512 nm was observed. The efficiency of the light-emitting device was 4.6 cd/A at a current density of 10 mA/cm$^2$.

Example 48

Organic EL Device Using Chemical Compound 400

An organic light-emitting device was obtained in the same manner as in Example 47 except that Chemical Compound 400 was used as a hole-transporting material instead of Chemical Compound 301. When forward bias was applied across the light-emitting device, green light emission from the Alq3 centered at the wavelength of 536 nm was observed. The efficiency of the light-emitting device was 3.4 cd/A at a current density of 10 mA/cm$^2$.

Example 49

Organic EL Device Using Chemical Compound 303

An organic light-emitting device was obtained in the same manner as in Example 47 except that Chemical Compound 303 was used as a hole-transporting material instead of Chemical Compound 301. When forward bias was applied across the light-emitting device, green light emission from the Alq3 centered at the wavelength of 536 nm was observed. The efficiency of the light-emitting device was 4.3 cd/A at a current density of 10 mA/cm$^2$.

Example 50

Organic EL Device Using Chemical Compound 403

An organic light-emitting device was obtained in the same manner as in Example 47 except that Chemical Compound 403 was used as a hole-transporting material instead of Chemical Compound 301. When forward bias was applied across the light-emitting device, green light emission from the Alq3 centered at the wavelength of 540 nm was observed. The efficiency of the light-emitting device was 3.7 cd/A at a current density of 10 mA/cm$^2$.

Example 51

Organic EL Device Using Chemical Compound 305

Figure 9:
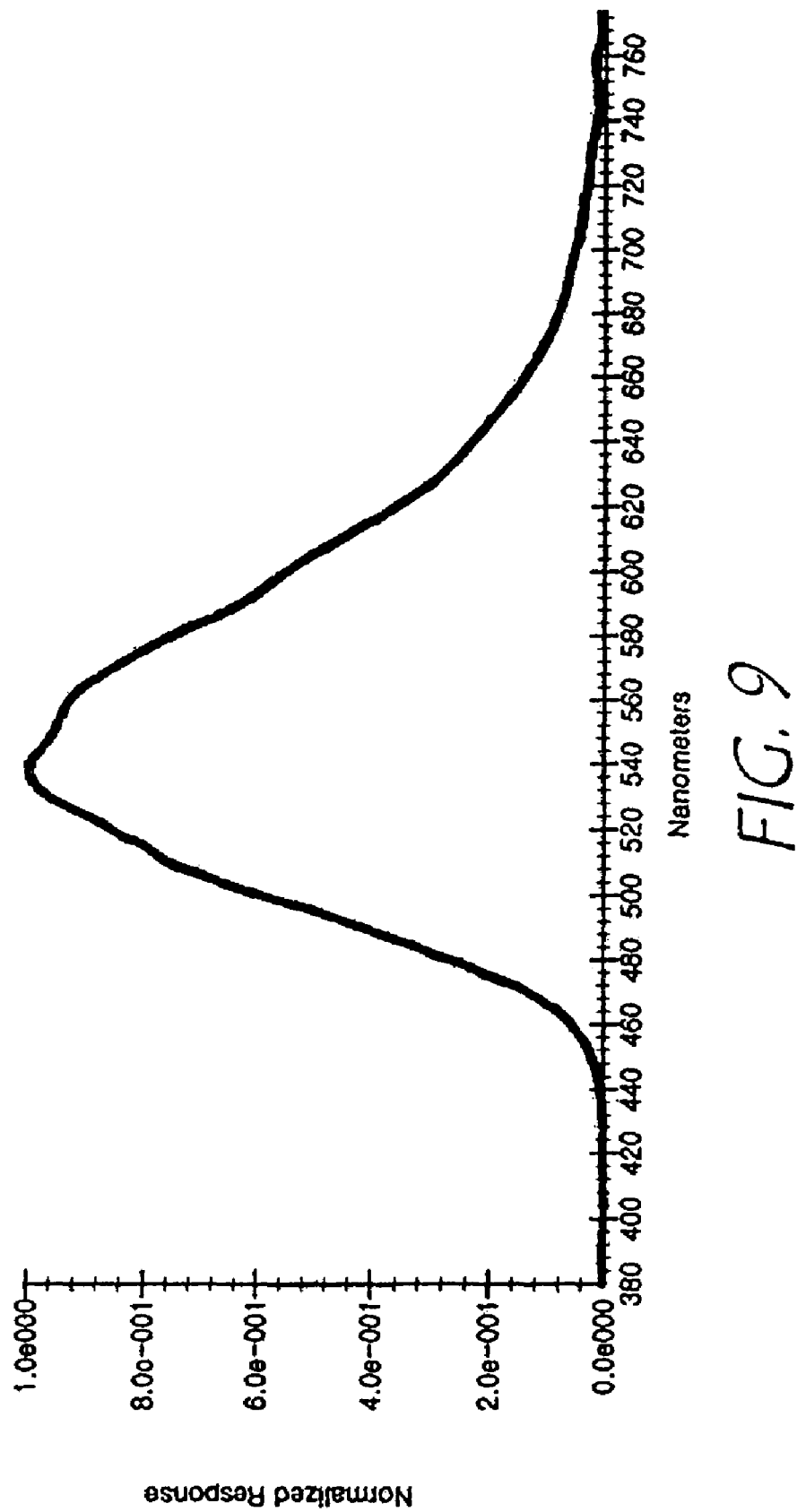
FIG. 9 is a spectrum of light emission from the organic EL device manufactured in Example 51.

An organic light-emitting device was obtained in the same manner as in Example 47 except that Chemical Compound 305 was used as a hole-transporting material instead of Chemical Compound 301. When forward bias was applied across the light-emitting device, green light emission from the Alq3 centered at the wavelength of 540 nm was observed. The efficiency of the light-emitting device was 4.8 cd/A at a current density of 10 mA/cm$^2$. FIG. 9 illustrates the light-emission spectrum of this device. Chemical Compound 305 used in the hole-transporting layer 7 has the band gap corresponding to blue light emission. Because the emitted light is green, not blue, Chemical Compound 305 is assumed to transport holes from the hole-injecting layer 5 to the light-emitting layer 9, rather than emitting light from itself.

Example 52

Organic EL Device Using Chemical Compound 308

An organic light-emitting device was obtained in the same manner as in Example 47 except that Chemical Compound 308 was used as a hole-transporting material instead of Chemical Compound 301. When forward bias was applied across the light-emitting device, green light emission from the Alq3 centered at the wavelength of 540 nm was observed. The efficiency of the light-emitting device was 2.3 cd/A at a current density of 10 mA/cm$^2$.

What is claimed is:

1. An organic electroluminescent ("EL") device comprising:

an anode; a cathode; and at least one layer located between the anode and the cathode, wherein the at least one layer comprises a light-emitting layer having a double-spiro compound of the Chemical Formula I:

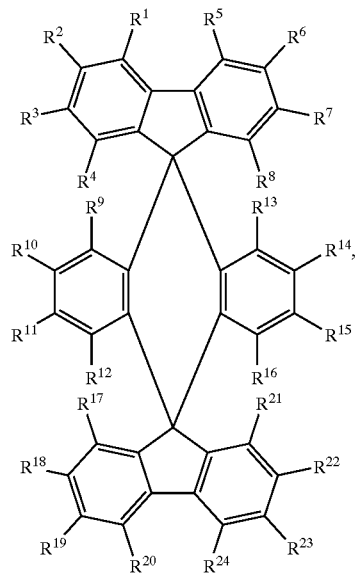

Chemical Formula I wherein R1 through R24 are substituent groups, identical or different, and wherein not all of R1 through R24 are hydrogen.

2. The organic EL device of claim 1, wherein the light-emitting layer comprises the double-spiro compound having a band gap corresponding to visible light emission.

3. The organic EL device of claim 2, wherein the band-gap for the visible light emission is from about 1.8 eV to about 3.5 eV.

4. The organic EL device of claim 1, wherein the light-emitting layer comprises a fluorescent or phosphorescent material.

5. The organic EL device of claim 1, further comprising a substrate, wherein the substrate contacts either the anode or the cathode.

6. The organic EL device of claim 1, wherein the at least one layer comprises the double-spiro compound having one or more properties selected from the group consisting of electron injection, electron transportation, light emission, hole transportation, and hole injection.

7. The organic EL device of claim 1, wherein the light-emitting layer comprises at least one compound selected from the group consisting of Chemical Compounds 100–137, 200–222, and 400–413 as shown below:

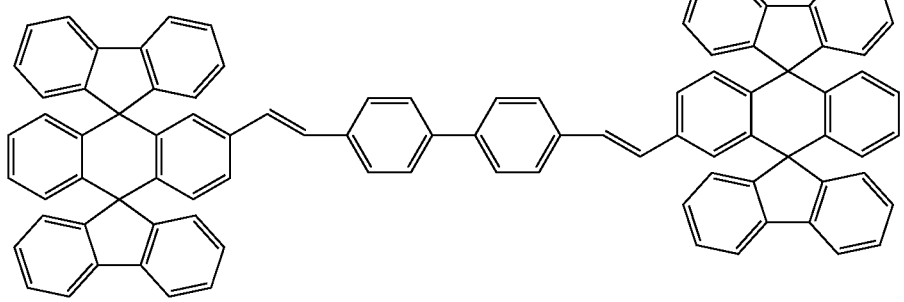

Chemical Compound 100

-continued
Chemical Compound 101
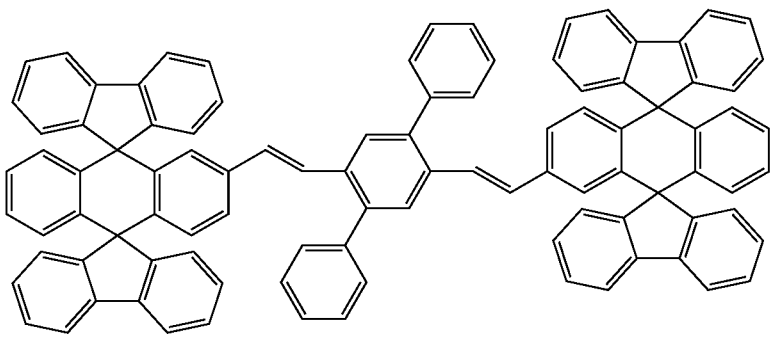
Chemical Compound 102
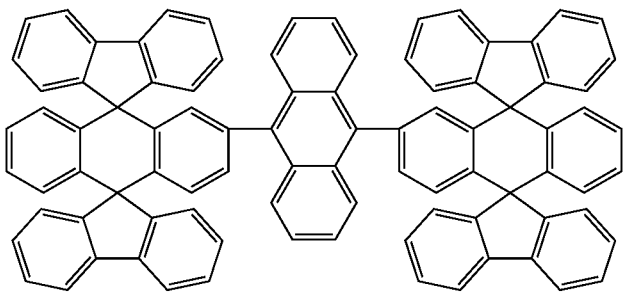
Chemical Compound 103
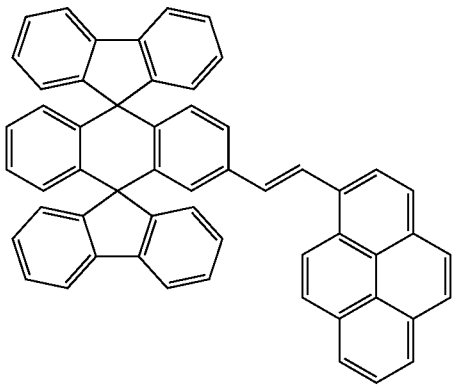
Chemical Compound 104
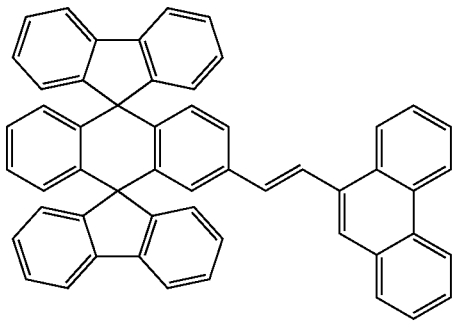
Chemical Compound 105
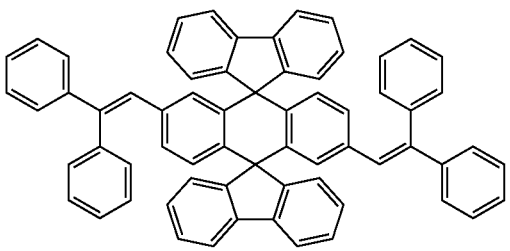
Chemical Compound 106
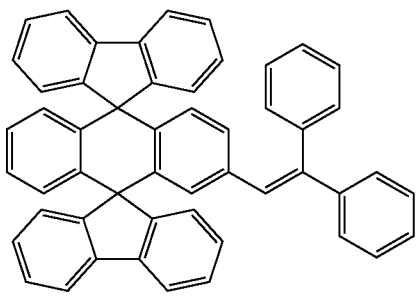

-continued
Chemical Compound 107
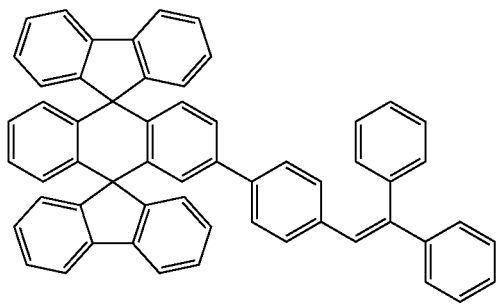
Chemical Compound 108
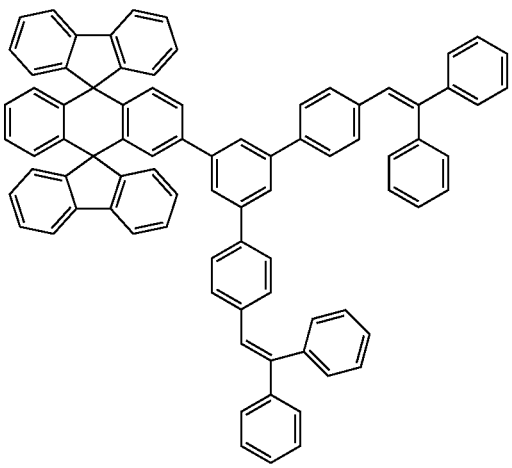
Chemical Compound 109
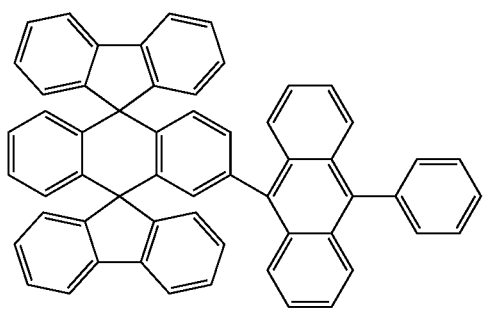
Chemical Compound 110
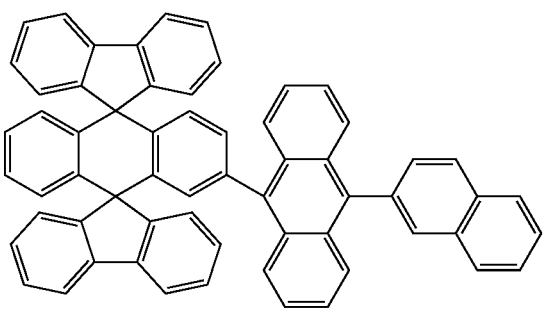
Chemical Compound 111
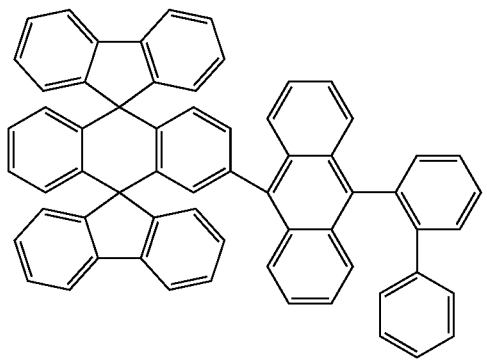
Chemical Compound 112
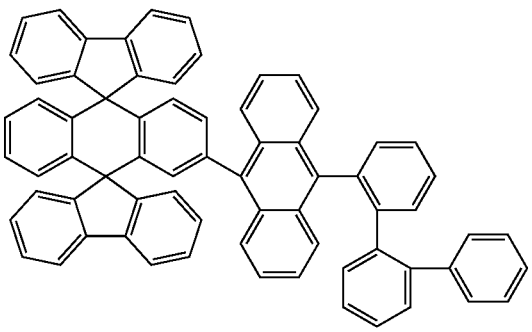
Chemical Compound 113
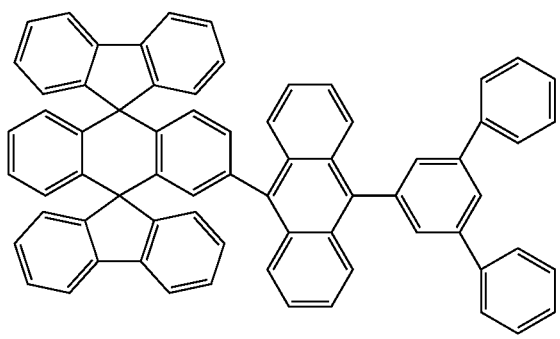

-continued
Chemical Compound 114
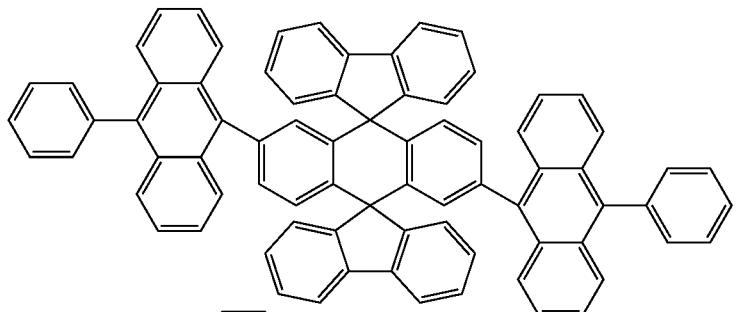
Chemical Compound 115
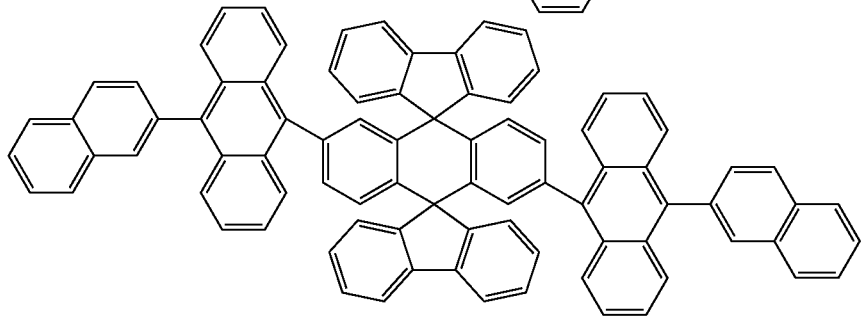
Chemical Compound 116
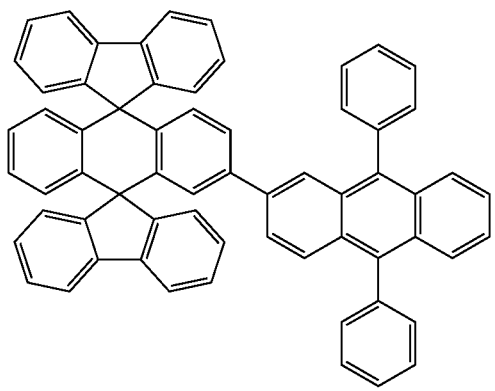
Chemical Compound 117
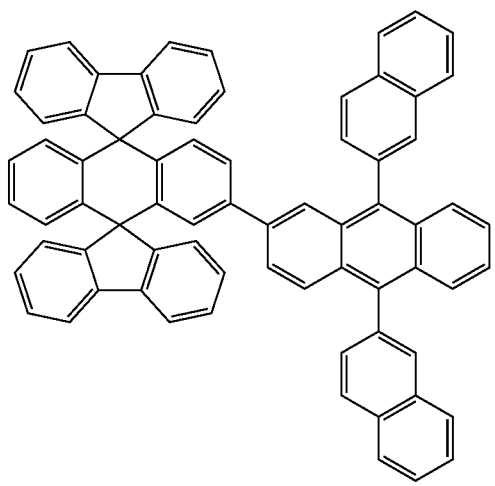
Chemical Compound 118
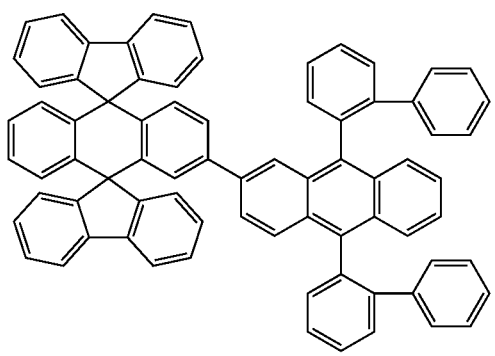
Chemical Compound 119
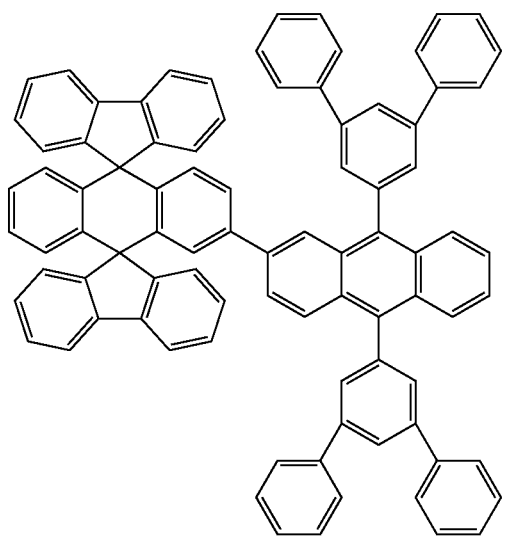

-continued
Chemical Compound 120
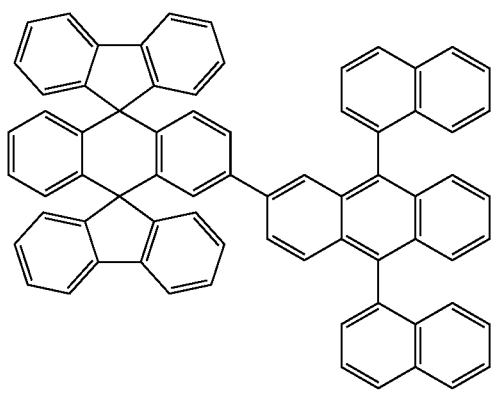
Chemical Compound 121
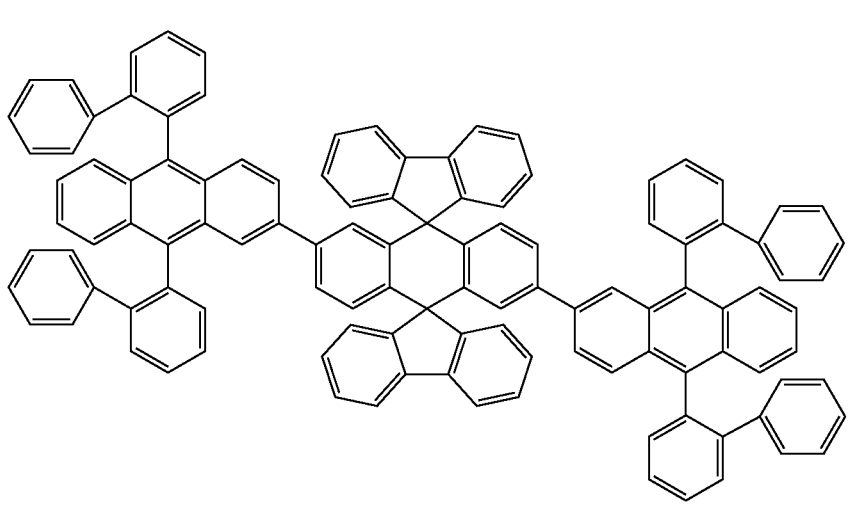
Chemical Compound 122
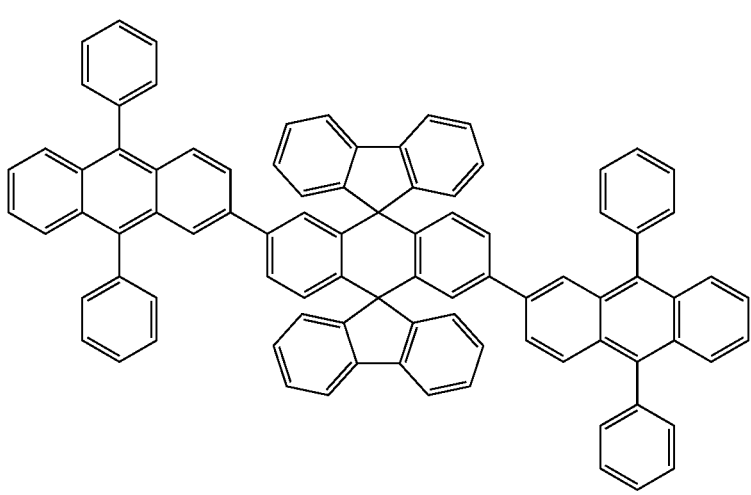

-continued
Chemical Compound 123
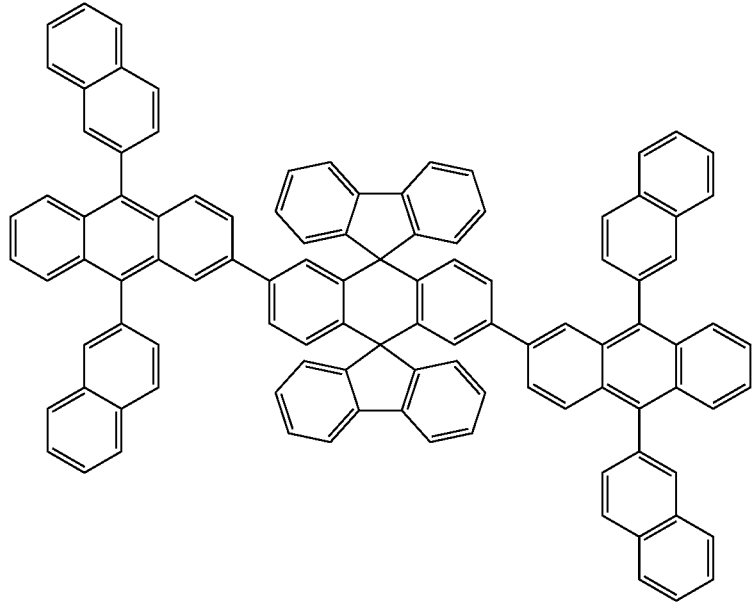
Chemical Compound 124
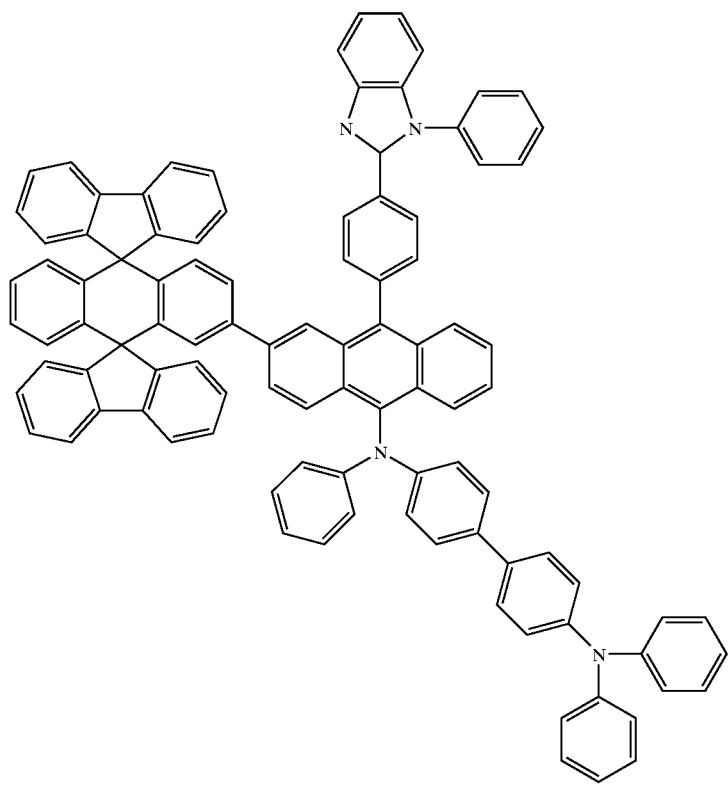

Chemical Compound 125
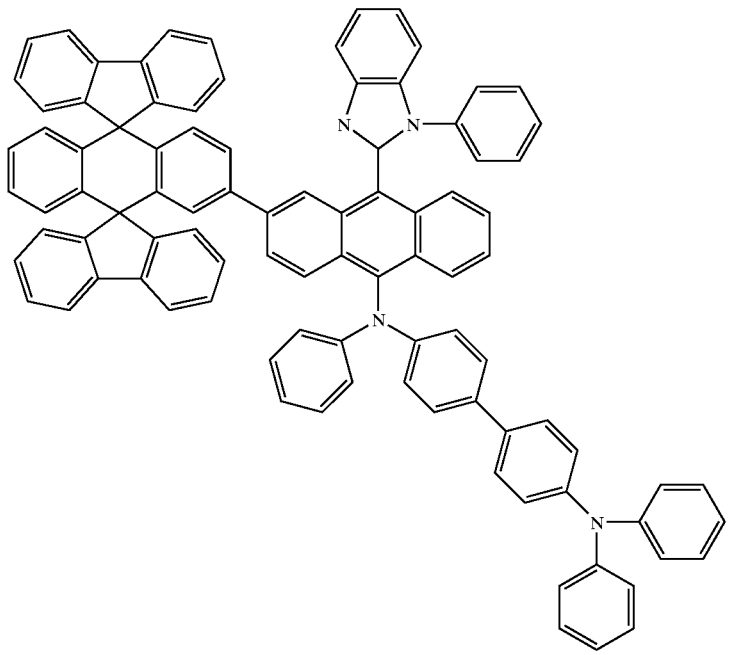
Chemical Compound 126
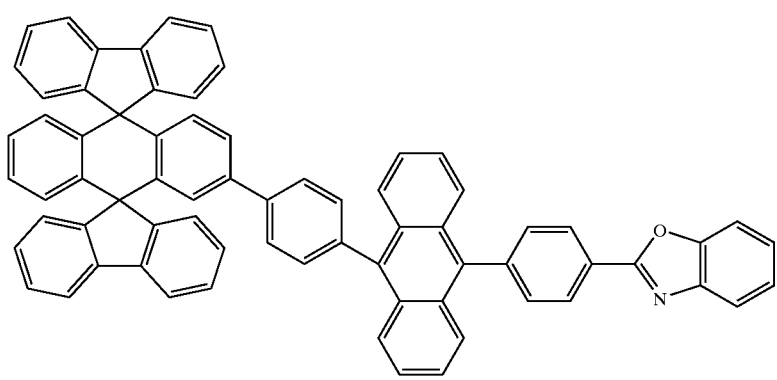

-continued
Chemical Compound 127
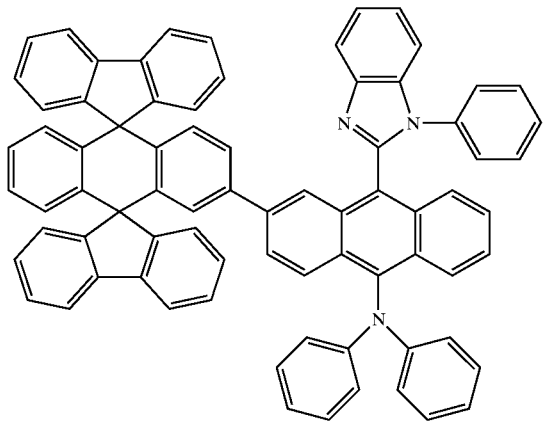
Chemical Compound 128
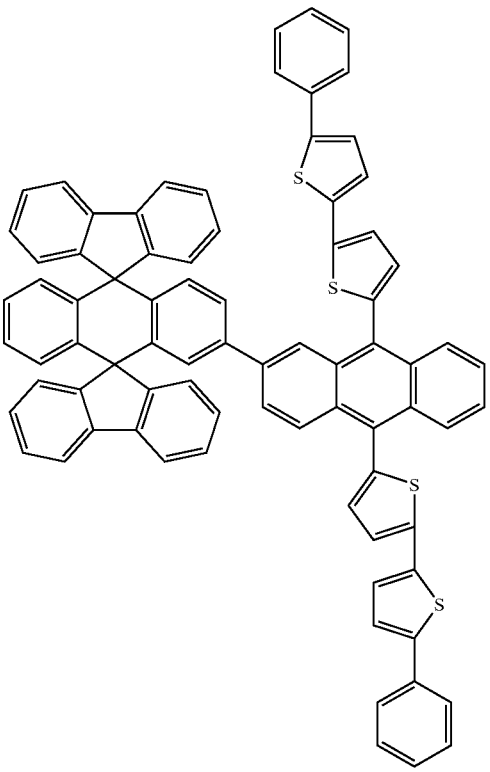
Chemical Compound 129
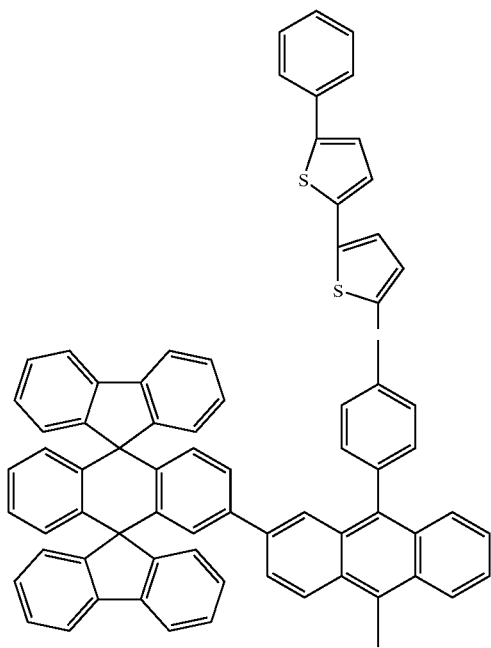

-continued
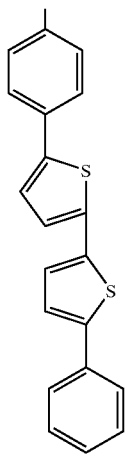
Chemical Compound 130
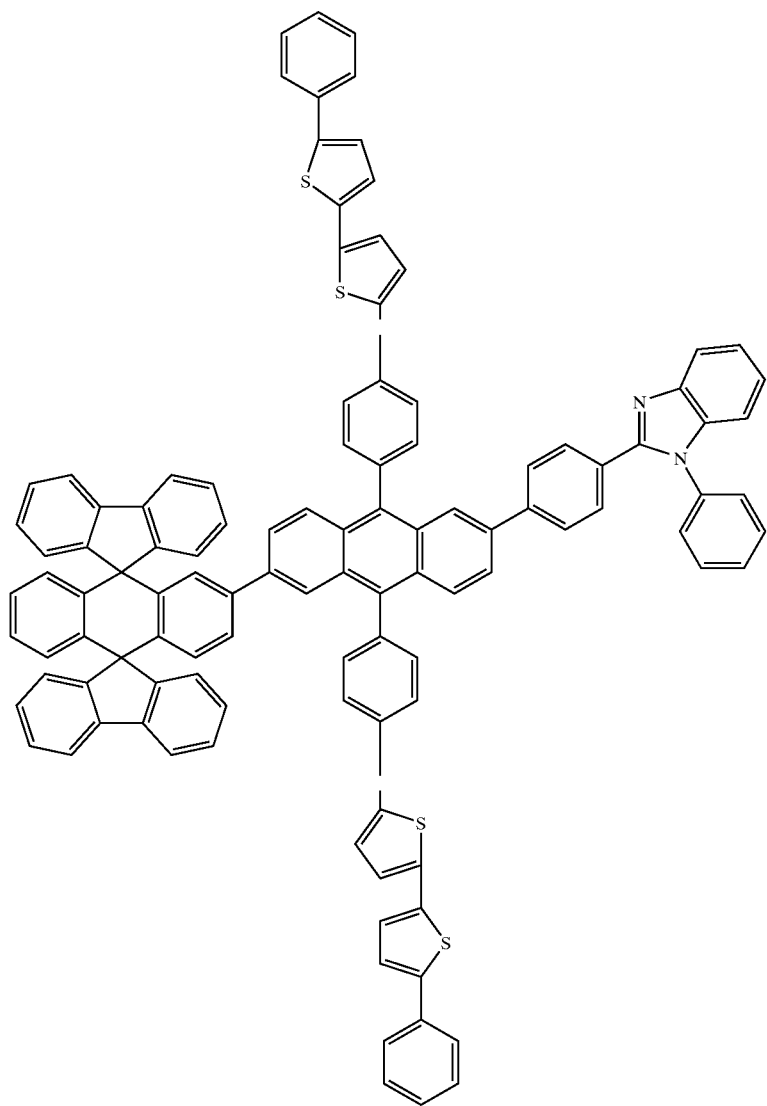

Chemical Compound 131
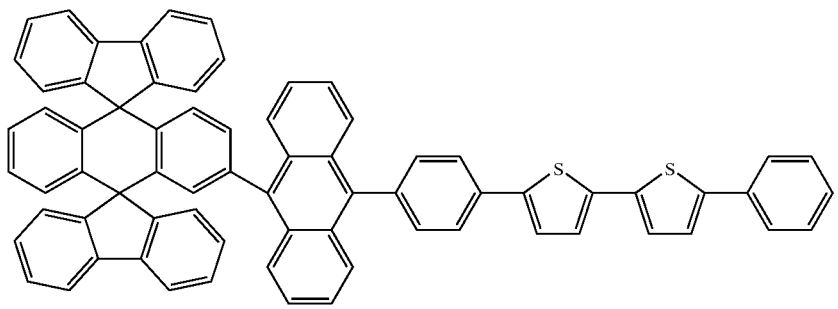
Chemical Compound 132
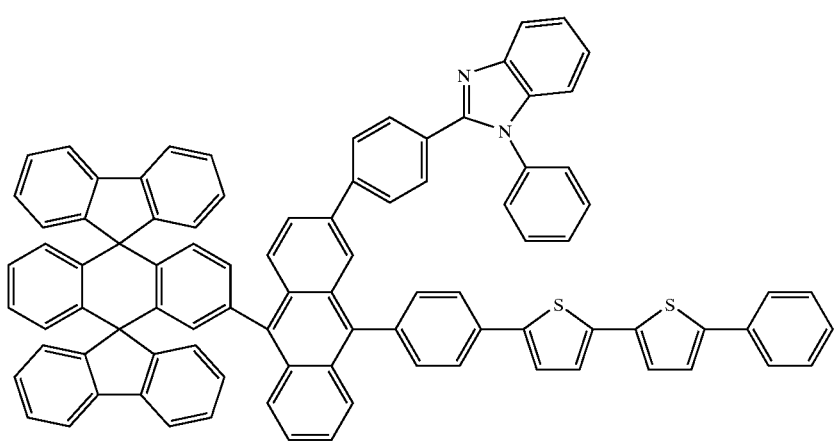
Chemical Compound 133
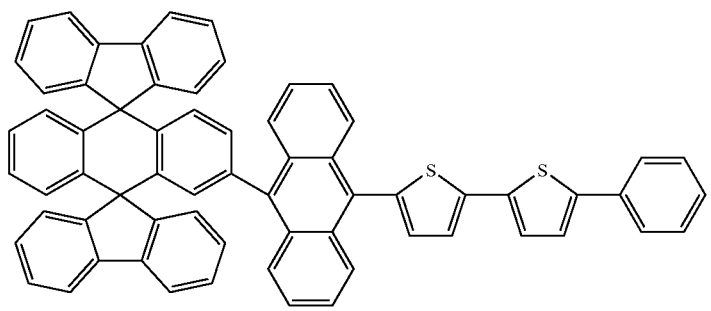
Chemical Compound 134
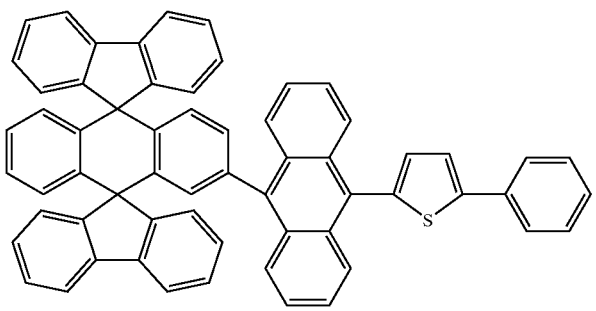

Chemical Compound 135
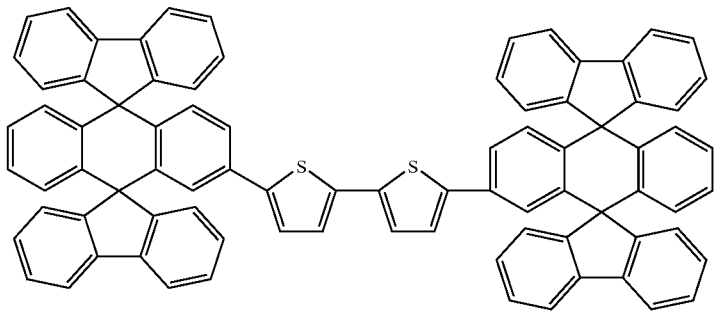
Chemical Compound 136
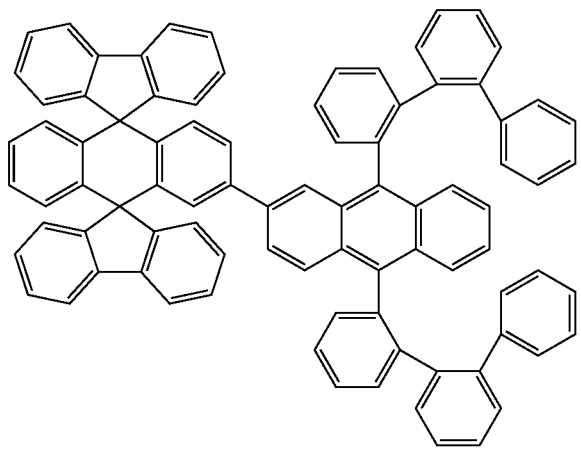
Chemical Compound 137
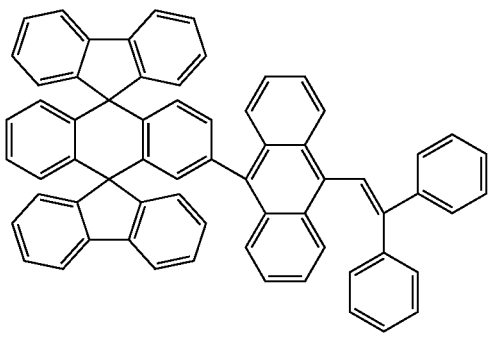
Chemical Compound 200
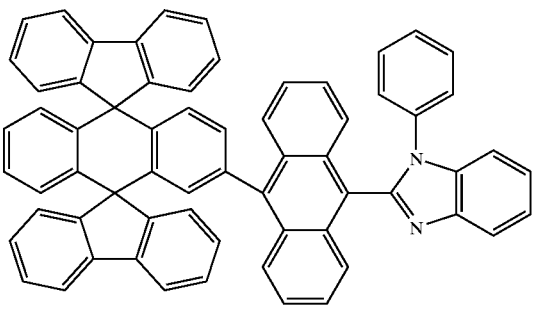
Chemical Compound 201
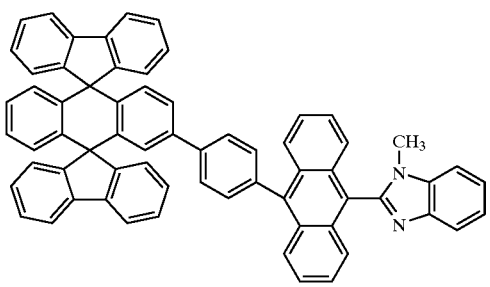
Chemical Compound 202
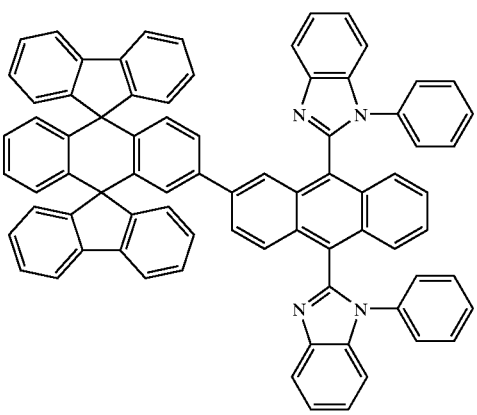

-continued
Chemical Compound 203
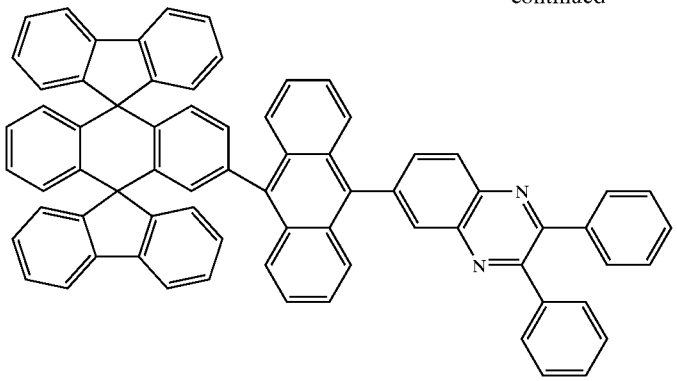
Chemical Compound 204
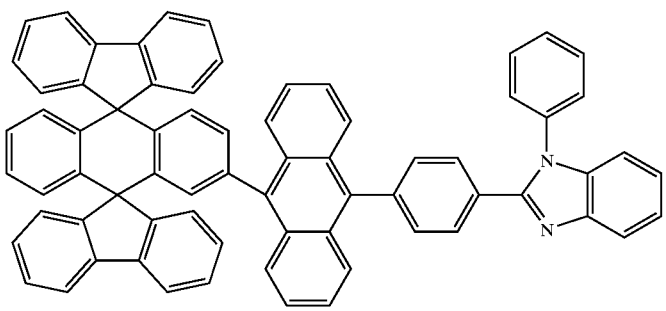
Chemical Compound 205
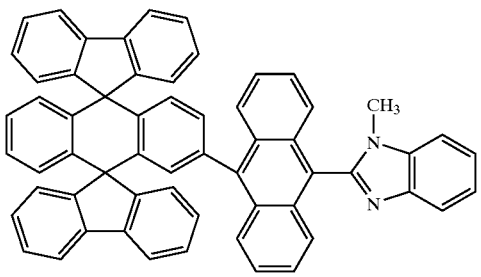
Chemical Compound 206
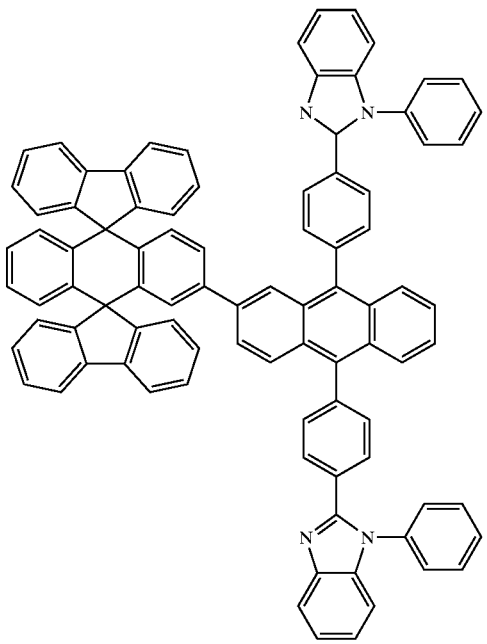
Chemical Compound 207
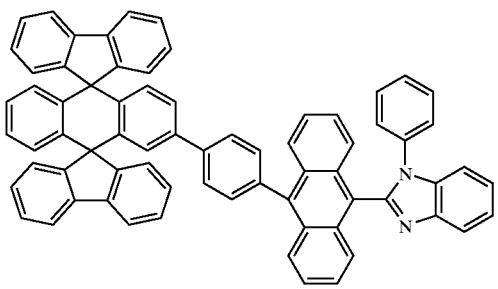
Chemical Compound 208
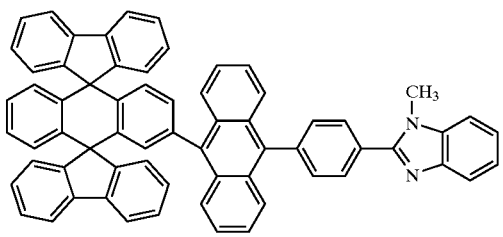

-continued
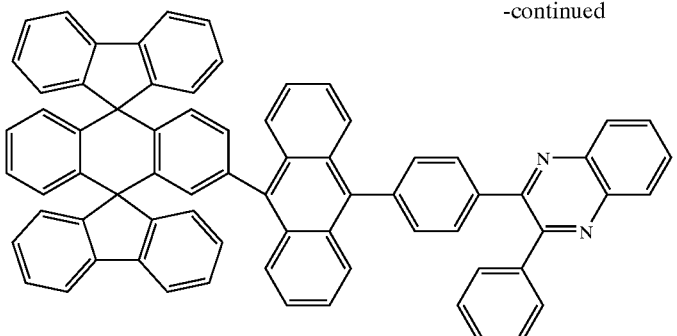
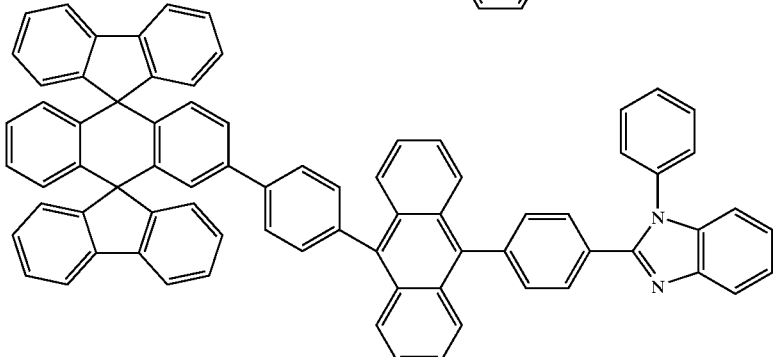
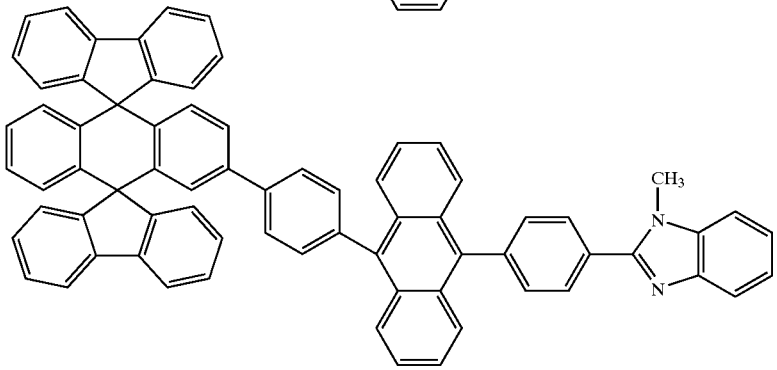
Chemical Compound 209
Chemical Compound 210
Chemical Compound 211
Chemical Compound 212
Chemical Compound 213
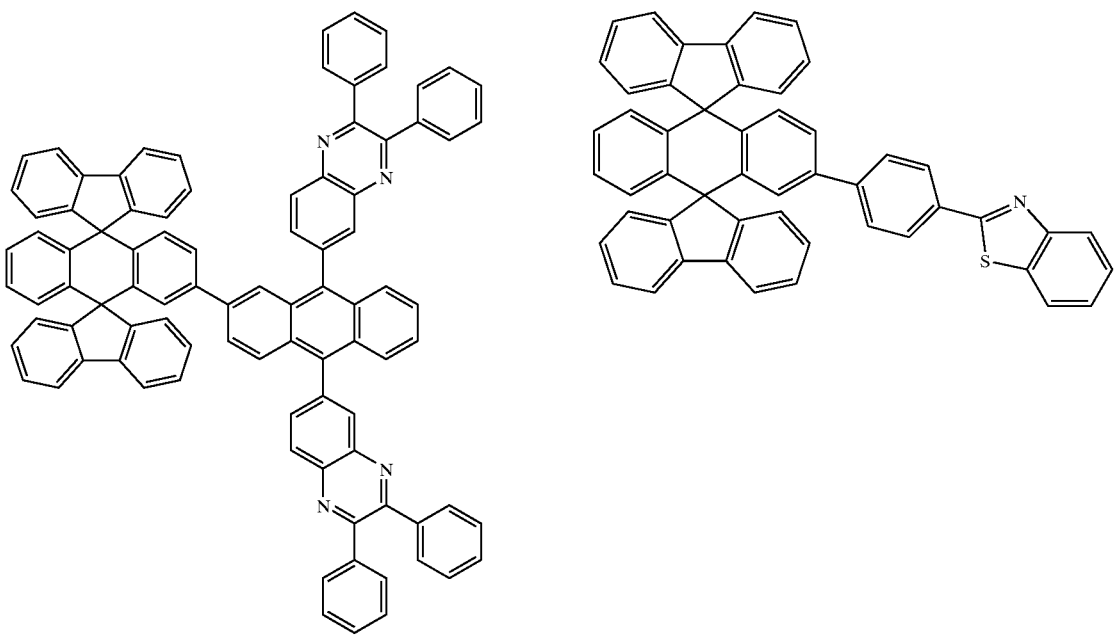

-continued
Chemical Compound 214
Chemical Compound 215
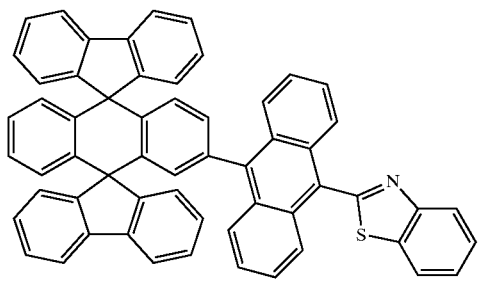
Chemical Compound 216
Chemical Compound 217
Chemical Compound 218
Chemical Compound 219

-continued
Chemical Compound 220
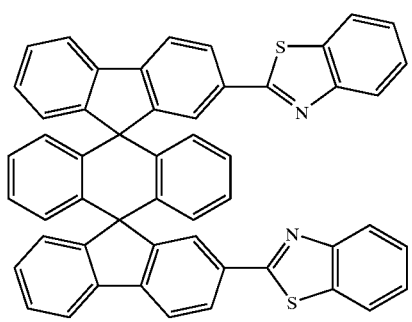
Chemical Compound 221
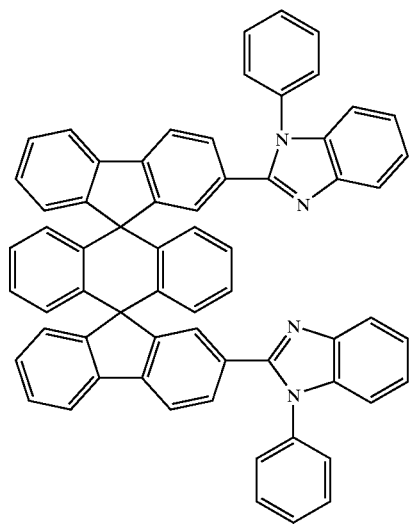
Chemical Compound 222
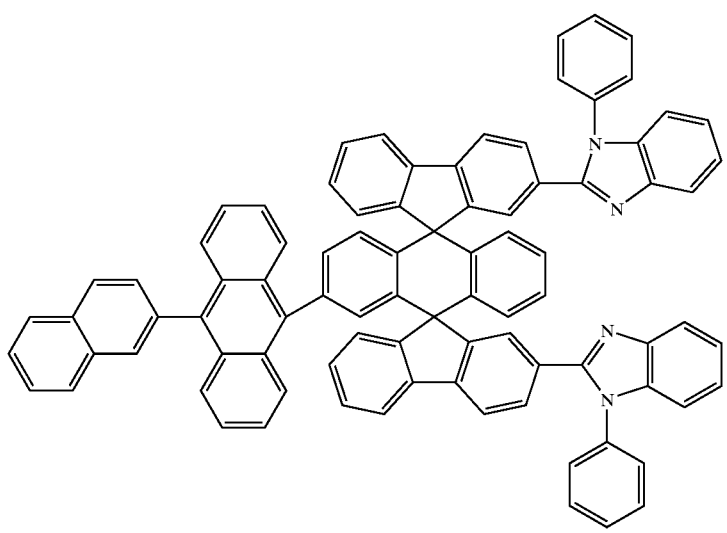
Chemical Compound 400
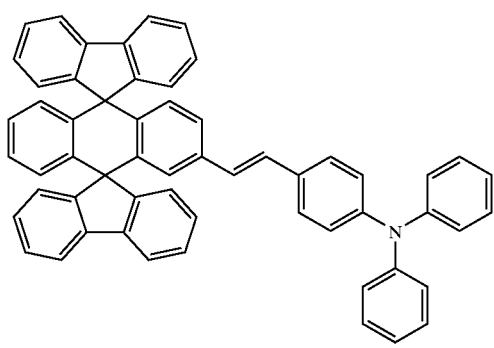
Chemical Compound 401
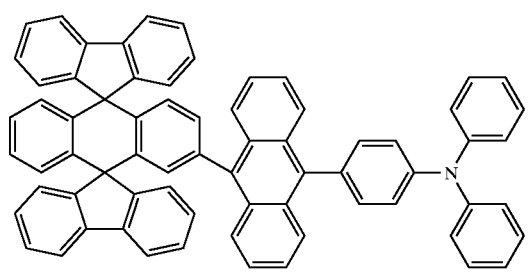

-continued
Chemical Compound 402
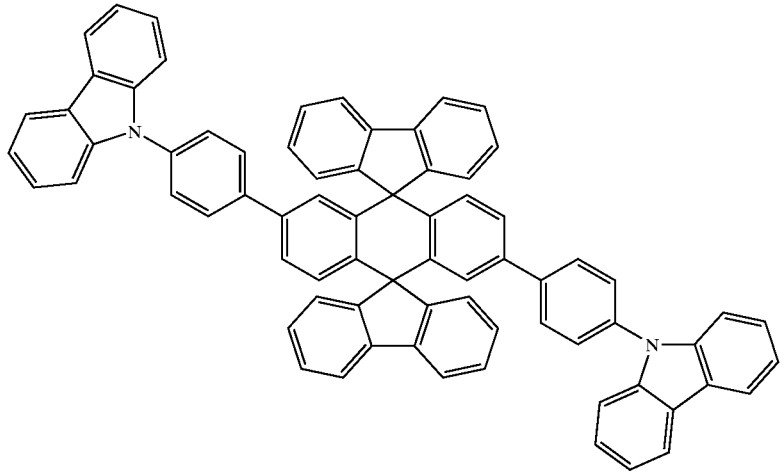
Chemical Compound 403
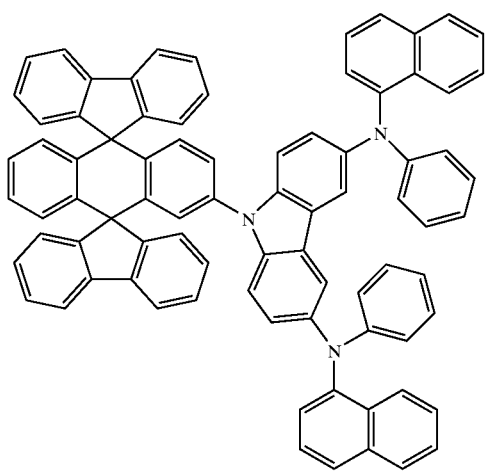
Chemical Compound 404
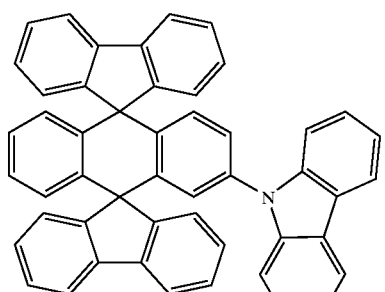
Chemical Compound 405
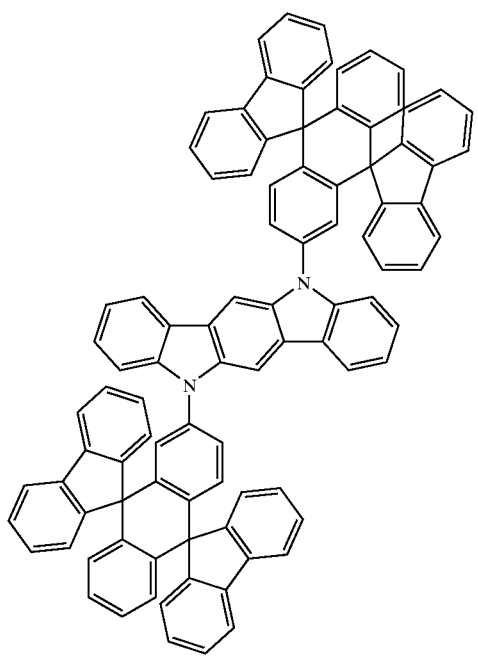
Chemical Compound 406
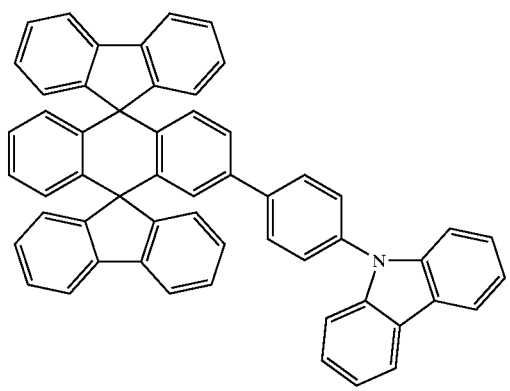

-continued
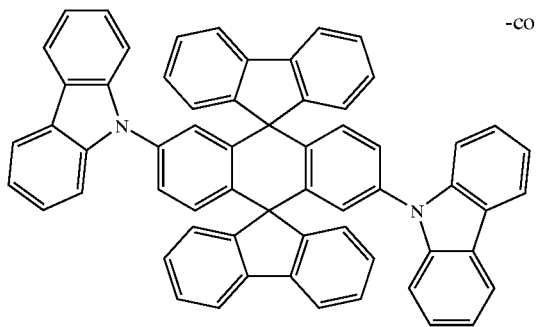
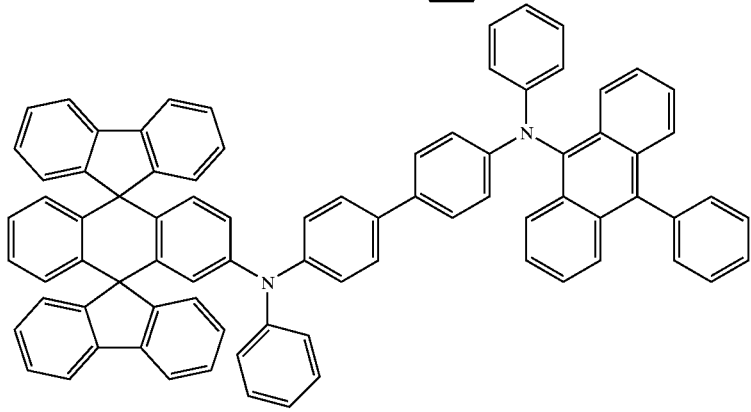
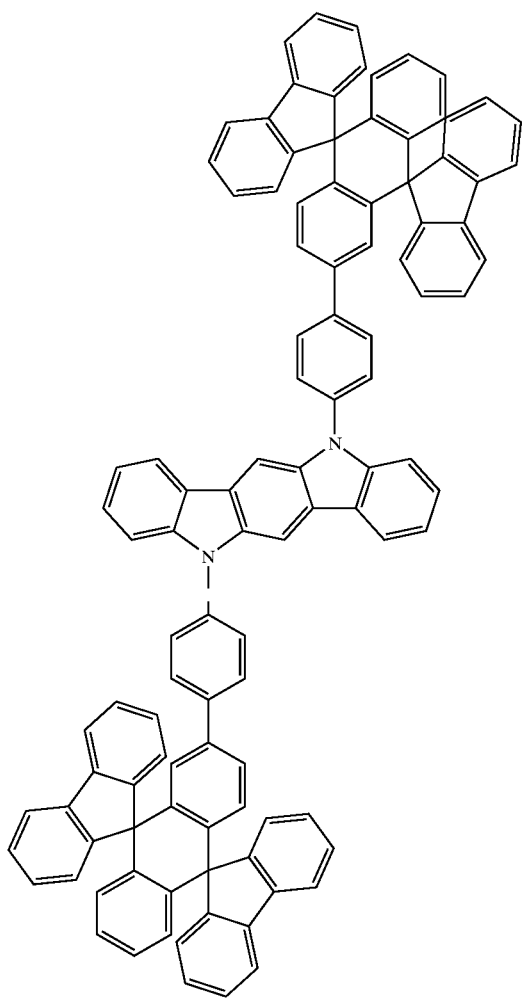
Chemical Compound 407
Chemical Compound 408
Chemical Compound 409

-continued

Chemical Compound 410

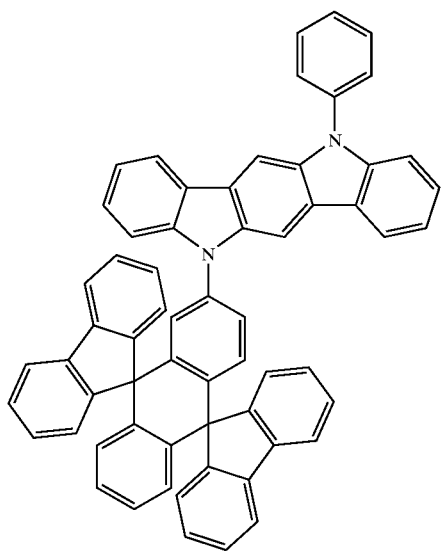

Chemical Compound 411

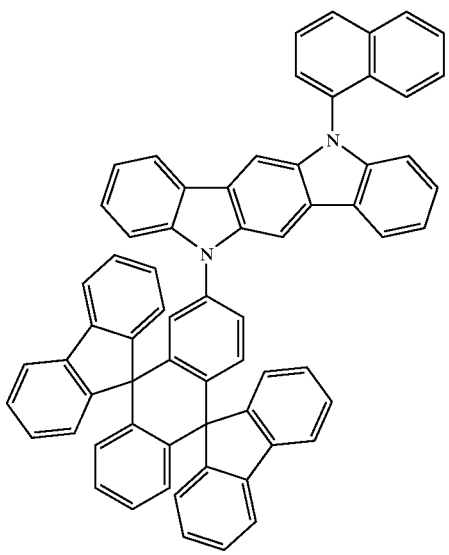

Chemical Compound 412

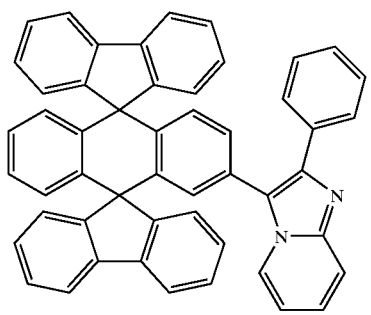

Chemical Compound 413

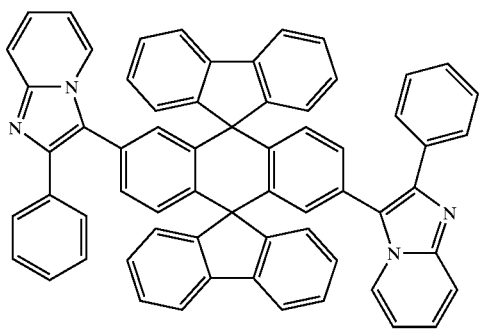

8. The organic EL device of claim 7, wherein the light-emitting layer further comprises a non-double-spiro light-emitting compound.

9. The organic EL device of claim 8, wherein the non-double-spiro light-emitting compound has a band gap smaller than a band gap of the double-spiro compound.

10. The organic EL device of claim 8, wherein the non-double-spiro light-emitting compound has a band gap greater than a band gap of the double-spiro compound.

11. The organic EL device of claim 8, wherein the non-double-spiro light-emitting compound is either fluorescent or phosphorescent compound.

12. The organic EL device of claim 1, wherein the at least one layer further comprises at least one of an electron-injecting and an electron-transporting layer.

13. The organic EL device of claim 12, wherein the at least one of the electron-injecting and electron-transporting layers comprises at least one compound selected from the group consisting of Chemical Compounds 200–222 as shown below:

Chemical Compound 200

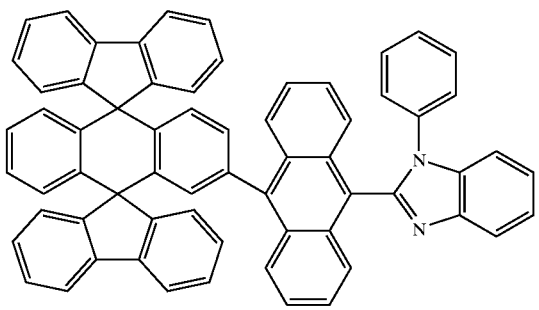

-continued
Chemical Compound 201
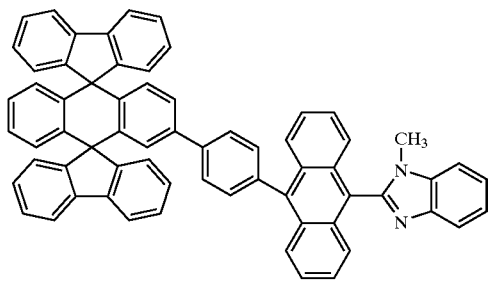
Chemical Compound 202
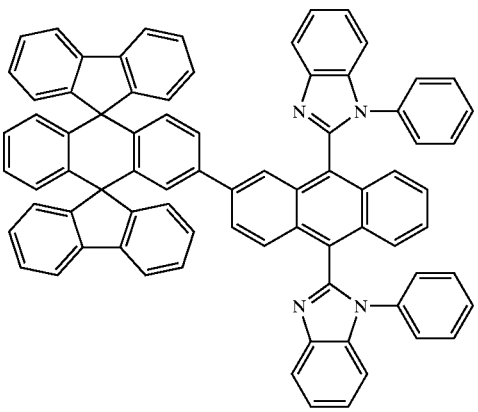
Chemical Compound 203
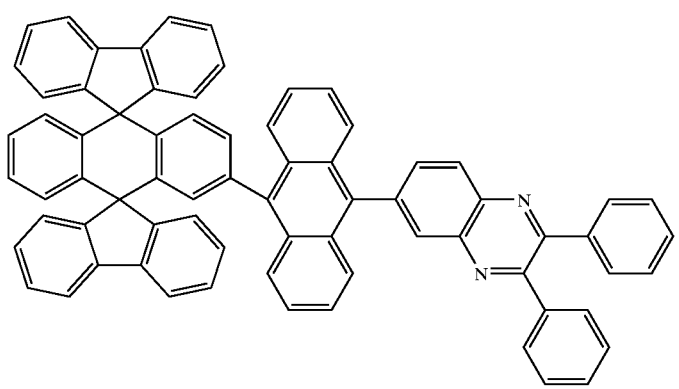
Chemical Compound 204
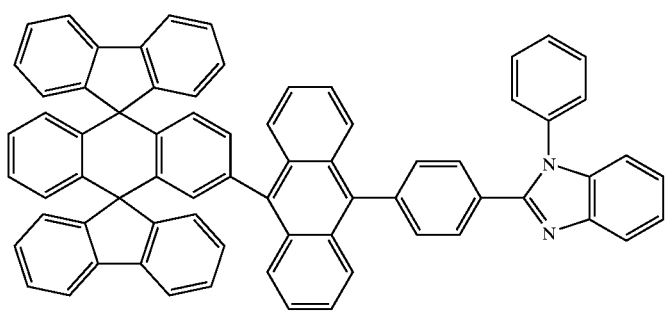

-continued
Chemical Compound 205
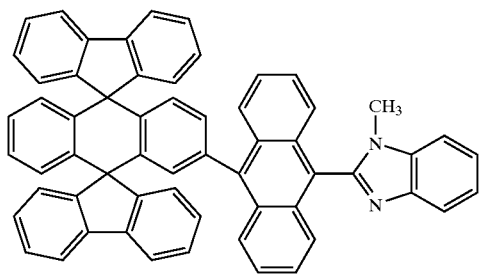
Chemical Compound 206
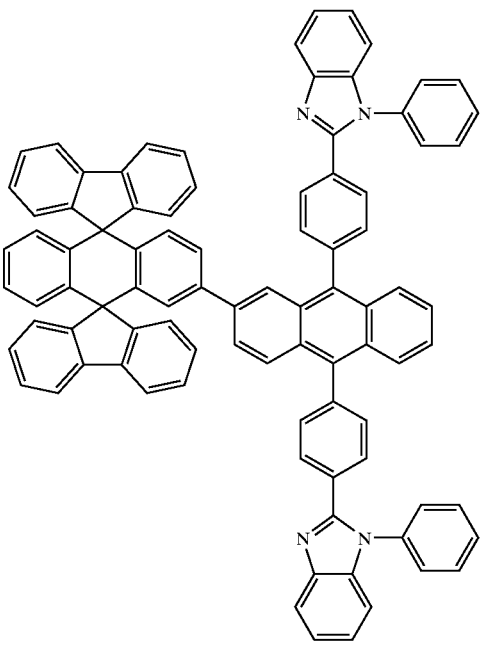
Chemical Compound 207
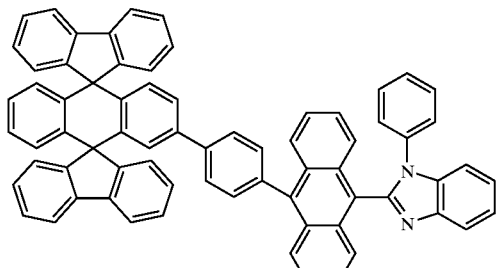
Chemical Compound 208
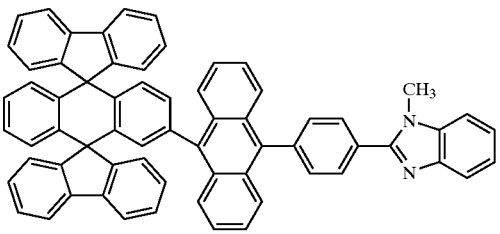
Chemical Compound 209
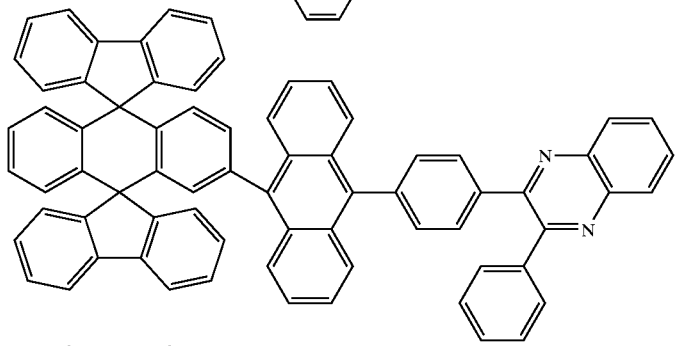
Chemical Compound 210
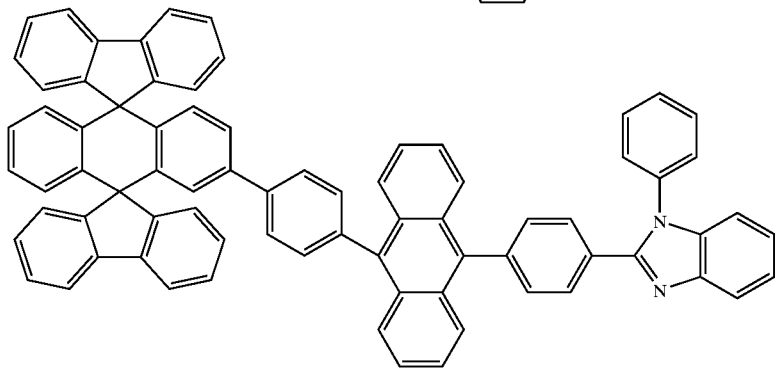

Chemical Compound 211
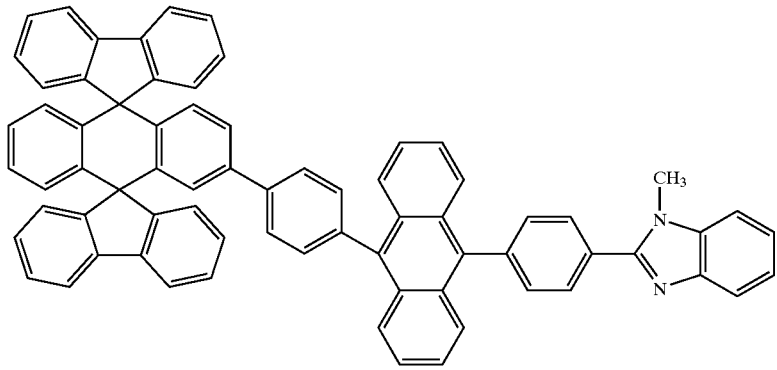
Chemical Compound 212
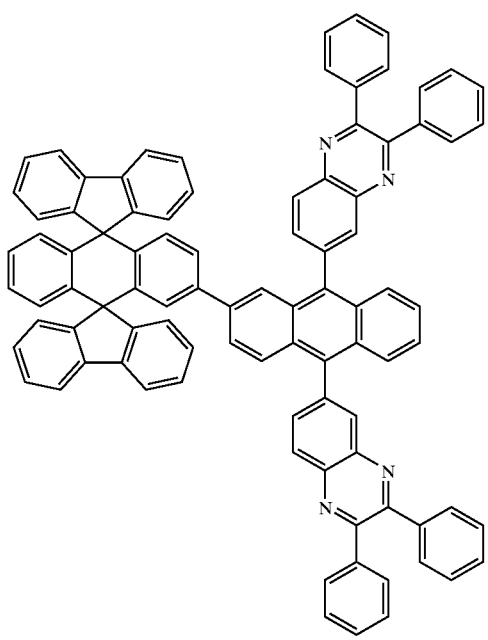
Chemical Compound 213
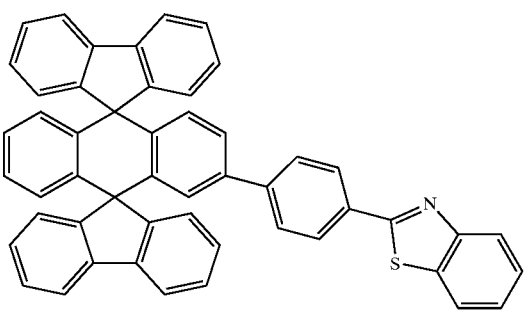
Chemical Compound 214
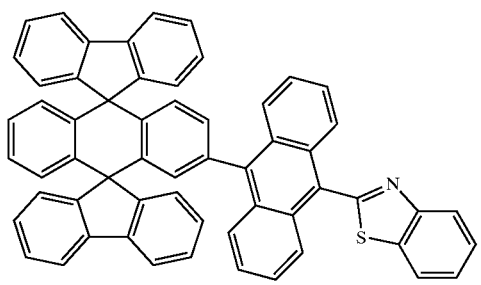
Chemical Compound 215
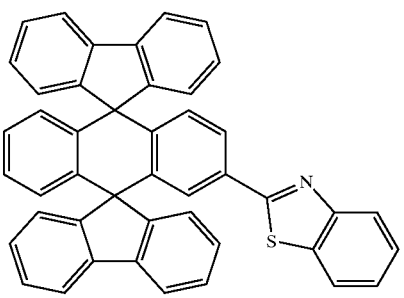

Chemical Compound 216
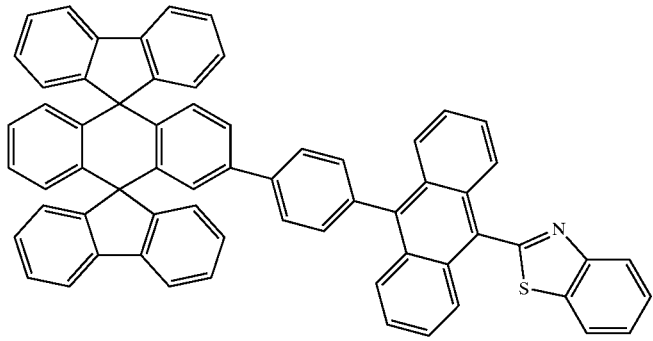
Chemical Compound 217
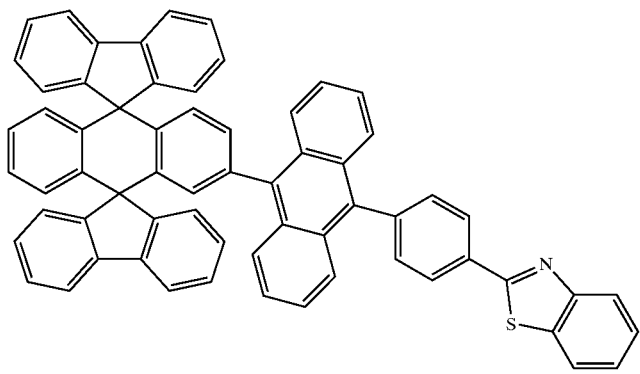
Chemical Compound 218
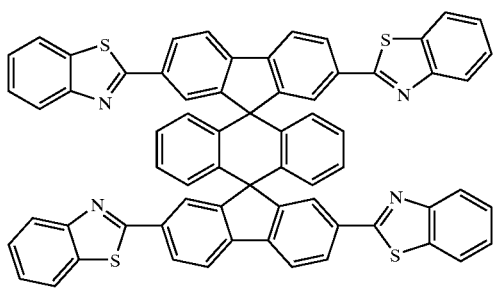
Chemical Compound 219
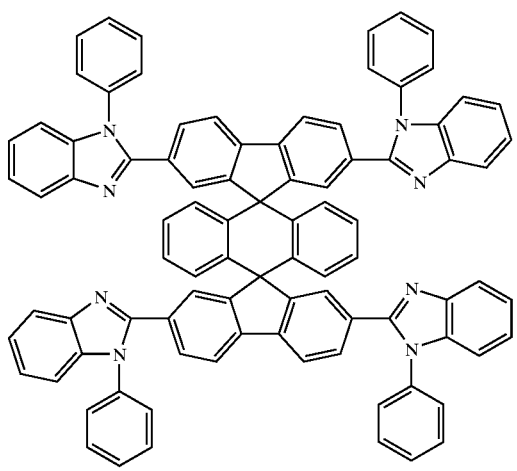

-continued

Chemical Compound 220

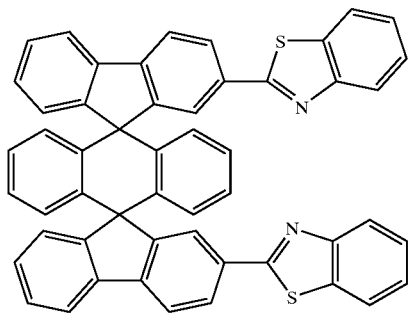

Chemical Compound 221

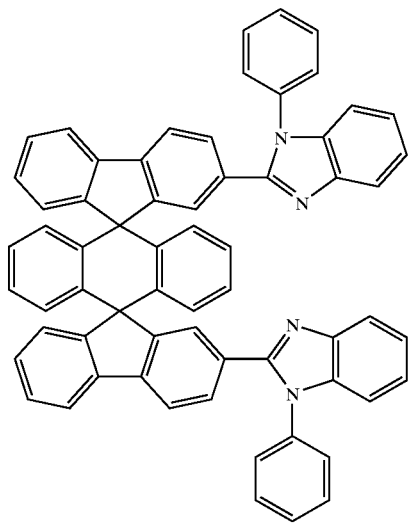

Chemical Compound 222

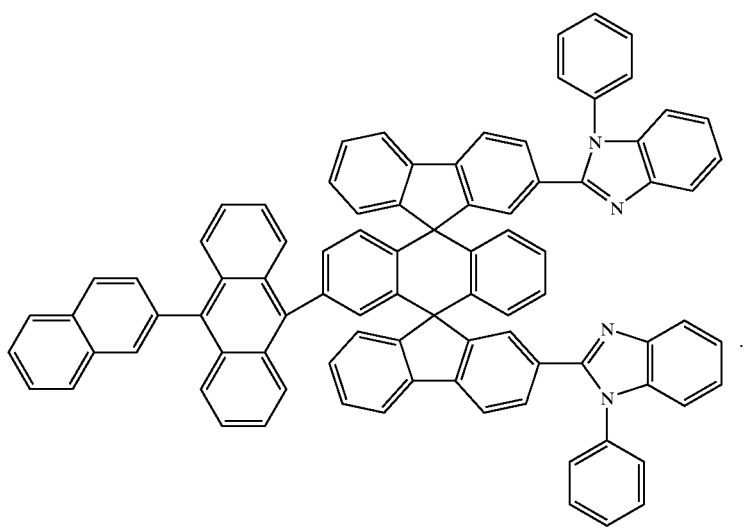

14. The organic EL device of claim 1, wherein the at least one layer further comprises at least one of a hole-injecting layer and a hole-transporting layer.

15. The organic EL device of claim 14, wherein the at least one of the hole-injecting and hole-transporting layers comprises at least one compound selected from the group consisting of Chemical Compounds 300–308 and 400–413 as shown below:

Chemical Compound 300

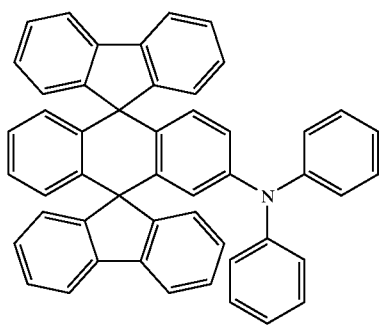

Chemical Compound 301

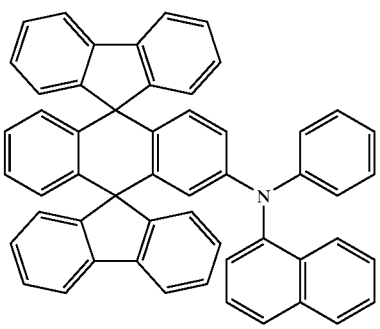

-continued
Chemical Compound 302
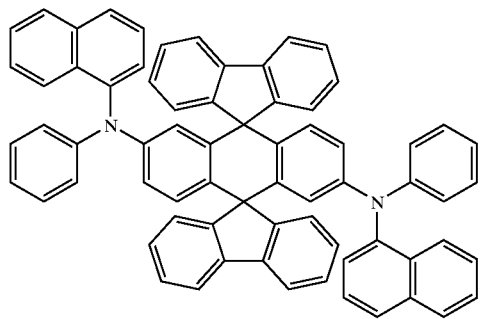
Chemical Compound 303
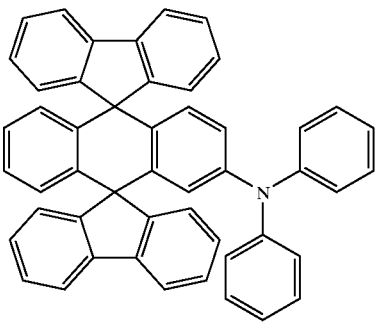
Chemical Compound 304
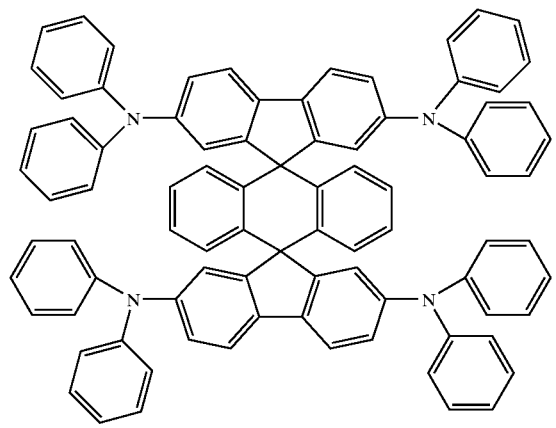
Chemical Compound 305
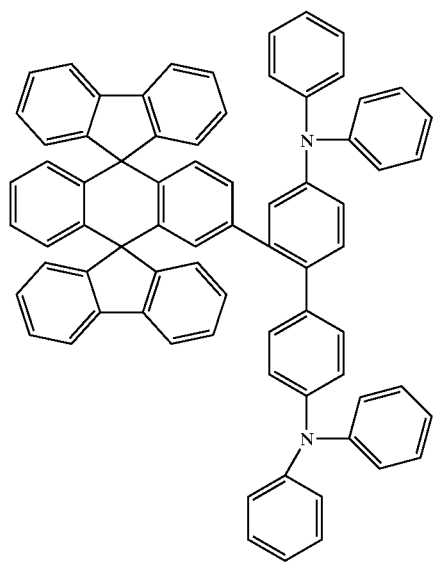
Chemical Compound 306
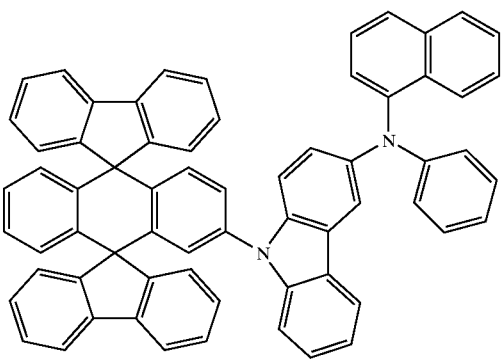

-continued
Chemical Compound 307
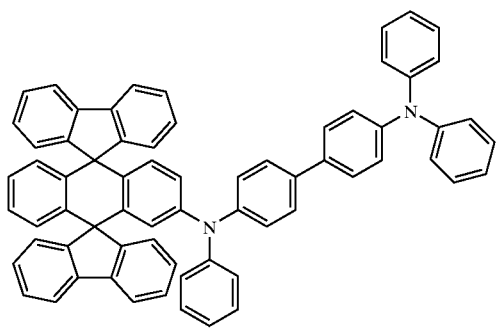
Chemical Compound 308
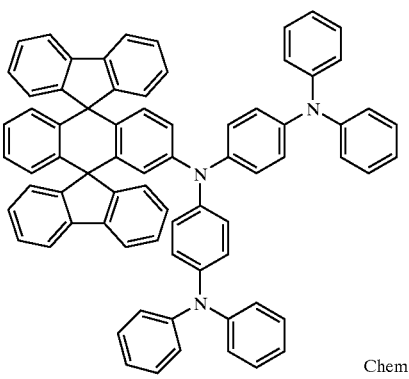
Chemical Compound 400
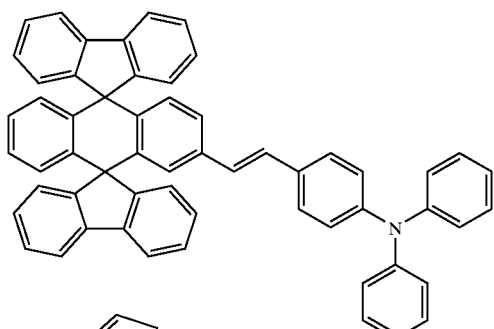
Chemical Compound 401
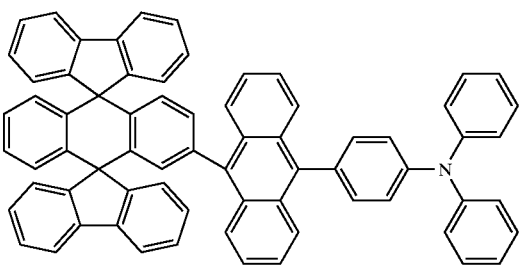
Chemical Compound 402
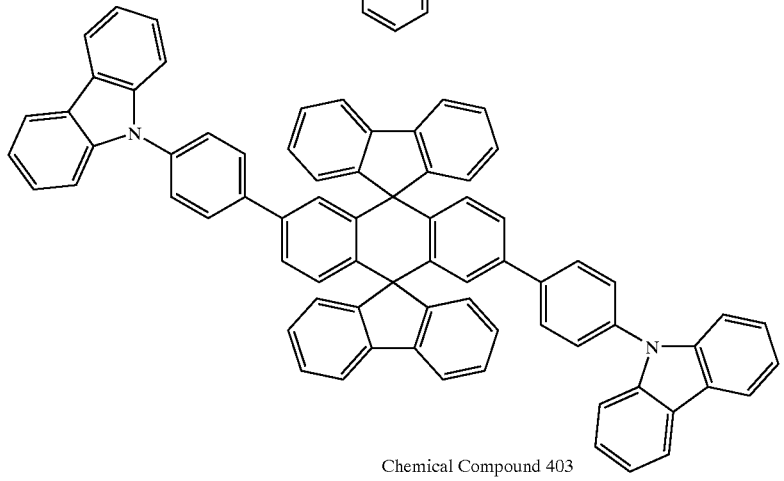
Chemical Compound 403
Chemical Compound 404
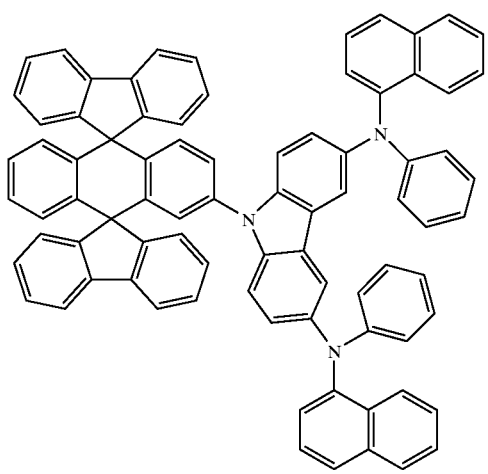

-continued
Chemical Compound 405
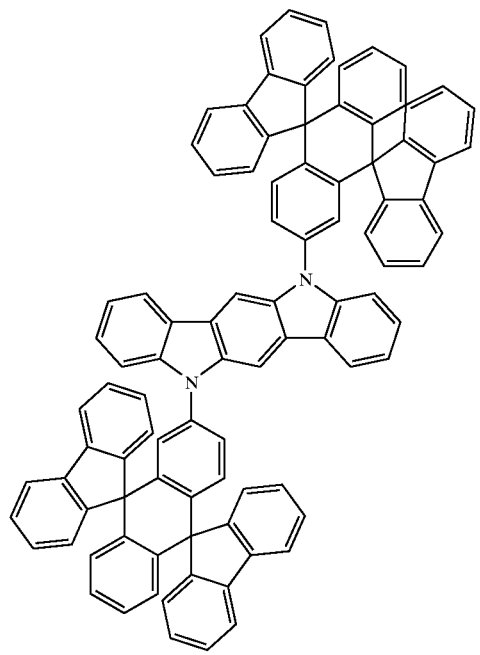
Chemical Compound 406
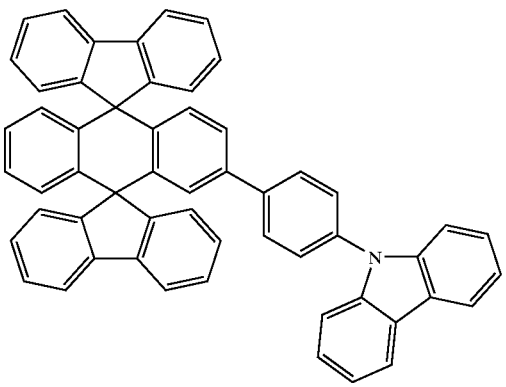
Chemical Compound 407
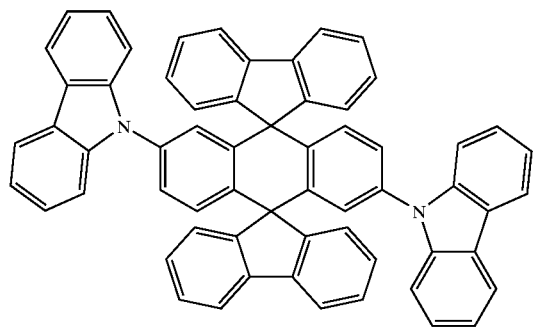
Chemical Compound 408
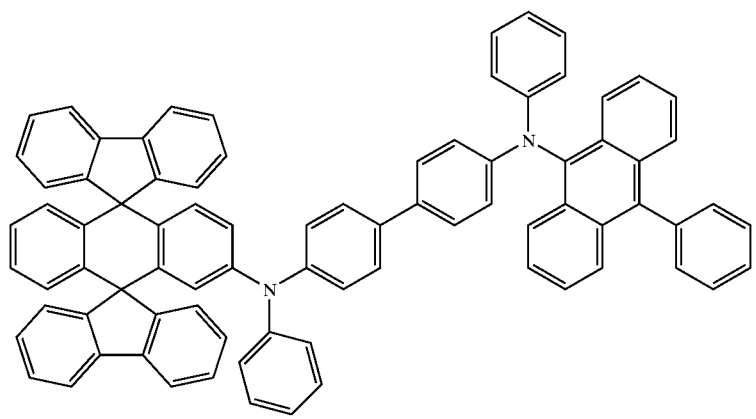

-continued
Chemical Compound 409
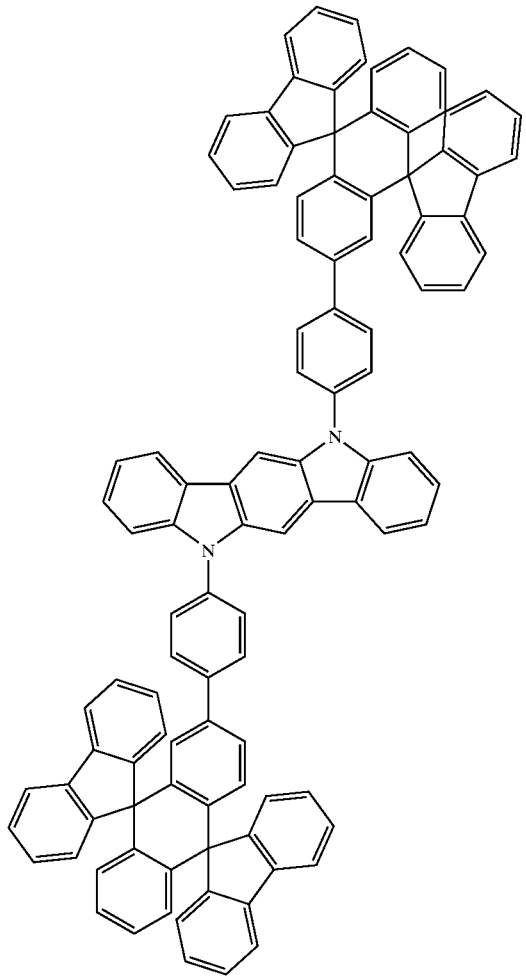
Chemical Compound 410
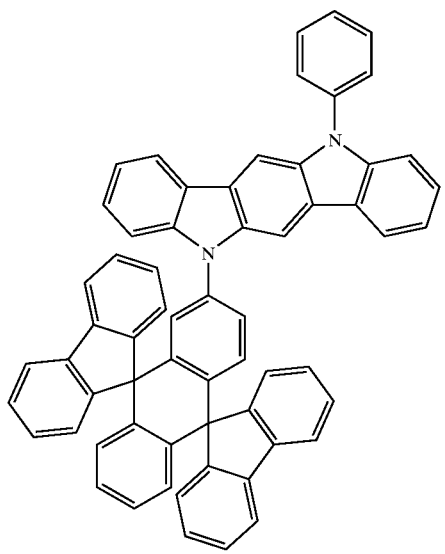
Chemical Compound 411
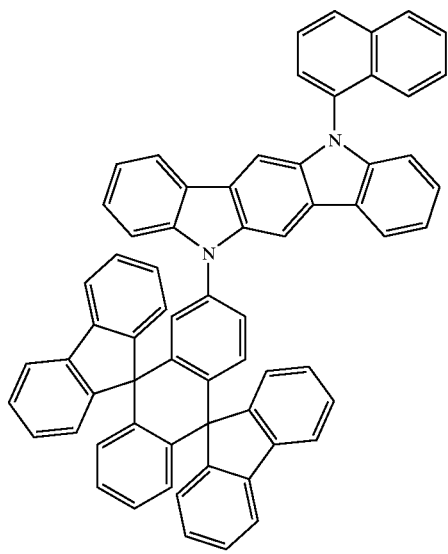

-continued

Chemical Compound 412

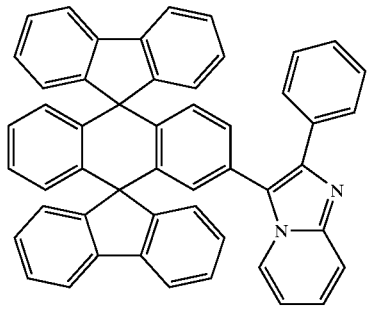

Chemical Compound 413

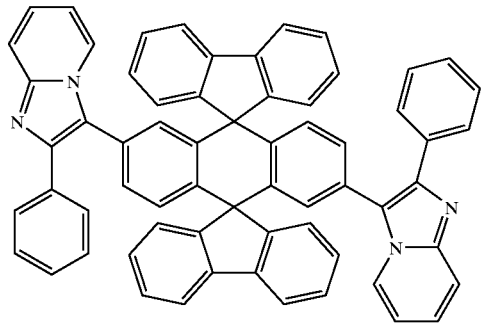

16. An electronic device comprising a display, wherein the display comprises the organic EL device of claim 1.

17. A method of generating visible light from an organic EL device of claim 1, comprising:
applying electric power between the anode and cathode of the organic EL device of claim 1;
the cathode injecting electrons toward the light-emitting layer;
the anode injecting holes toward the light-emitting layer; and
allowing recombination of at least part of the injected electrons and holes in the light-emitting layer, thereby generating visible light from the light-emitting layer.

18. The method of claim 17, wherein the light-emitting layer comprises the double-spiro compound having a light-emitting property.

19. The method of claim 18, wherein the light-emitting layer further comprises a non-double-spiro light-emitting compound.

20. The method of claim 17, wherein the at least one layer comprises the double-spiro compound having one or more properties selected from the group consisting of visible light emission, electron transportation, electron injection, hole transportation, and hole injection.

21. A method of manufacturing the organic EL device of claim 1, the method comprising:

forming a first conductive layer;
depositing a material comprising the double-spiro compound of the Chemical Formula I on a first conductive layer so as to form at least one layer comprising the light-emitting layer; and
forming a second conductive layer on the material, wherein either of the first and second conductive layers corresponds to the anode or cathode.

22. The method of claim 21, wherein the formation of the light-emitting layer comprises depositing the double-spiro compound having a light-emitting property.

23. The method of claim 22, wherein the formation of the light-emitting layer comprises co-depositing a non-double-spiro light-emitting compound.

24. The method of claim 21, wherein the formation of the at least one layer comprises forming layers having one or more functions selected from the group consisting of visible light emission, electron transportation, electron injection, hole transportation, and hole injection.

25. The method of claim 24, wherein the formation of the layers having one or more functions comprises depositing a double-spiro compound.

26. The method of claim 24, wherein the formation of the layers having one or more functions comprises depositing a non-double-spiro compound.

* * * * *